United States Patent
Lam et al.

(10) Patent No.: US 10,793,824 B2
(45) Date of Patent: Oct. 6, 2020

(54) SALT FORMULATIONS FOR THE FERMENTATION OF MARINE MICROORGANISMS

(71) Applicant: Celgene International II Sárl, Couvet (CH)

(72) Inventors: Kin Sing Lam, San Diego, CA (US); Ginger Tsueng, San Diego, CA (US)

(73) Assignee: Celgene International II Sárl, Couvet (CH)

(\*) Notice: Subject to any disclaimer, the term of this patent is extended or adjusted under 35 U.S.C. 154(b) by 59 days.

(21) Appl. No.: 16/000,358

(22) Filed: Jun. 5, 2018

(65) Prior Publication Data

US 2018/0282686 A1    Oct. 4, 2018

Related U.S. Application Data

(62) Division of application No. 14/624,183, filed on Feb. 17, 2015, now Pat. No. 10,011,814, which is a division of application No. 11/860,491, filed on Sep. 24, 2007, now Pat. No. 8,986,971.

(60) Provisional application No. 60/952,349, filed on Jul. 27, 2007, provisional application No. 60/952,368, filed on Jul. 27, 2007, provisional application No. 60/949,147, filed on Jul. 11, 2007, provisional application No. 60/846,774, filed on Sep. 22, 2006.

(51) Int. Cl.
*C12N 1/20* (2006.01)
*C12P 17/18* (2006.01)

(52) U.S. Cl.
CPC .............. *C12N 1/20* (2013.01); *C12P 17/188* (2013.01); *C12N 2500/05* (2013.01); *C12N 2500/12* (2013.01); *C12N 2500/14* (2013.01); *C12N 2500/16* (2013.01); *C12N 2500/20* (2013.01); *C12N 2500/38* (2013.01); *Y10S 435/822* (2013.01)

(58) Field of Classification Search
CPC .. C12N 1/20; C12N 2500/05; C12N 2500/12; C12N 2500/14; C12N 2500/16; C12N 2500/20; C12N 2500/38; C12P 17/188; Y10S 435/822; A23V 2002/00; A23V 2250/1868; A23V 2250/187; A23K 20/158; A23K 40/30; A23K 50/30; A23K 50/75; A23L 33/115; A23L 33/12; A61K 31/202; A61K 36/02; A61K 38/08; A61K 38/10; A61K 38/16; A61K 41/0009; A61K 41/0057; A61K 41/0071; A61K 47/10; A61K 47/26; A61K 47/34; A61K 47/64; A61K 47/6911; A61K 8/64; A61K 9/0019; A61K 9/0063; A61K 9/06; A61K 8/21; A61K 8/24; A61K 8/44; A61K 8/466; A61K 8/4943; A61K 8/4913; A61Q 11/00; A01N 37/46; C07K 14/001;
C07K 7/06; C07K 7/08; G01N 33/569; Y02A 50/47; Y02A 50/473; B01J 2219/00006; C04B 14/26; C04B 28/02; C04B 28/10; Y02P 40/18
See application file for complete search history.

(56) References Cited

U.S. PATENT DOCUMENTS

| | | | |
|---|---|---|---|
| 5,292,892 A | 3/1994 | Takahashi et al. | |
| 5,399,711 A | 3/1995 | Takahashi et al. | |
| 5,405,762 A | 4/1995 | Takahashi et al. | |
| 6,065,245 A | 5/2000 | Seawright | |
| 6,410,281 B1 | 6/2002 | Barclay | |
| 6,451,567 B1 | 9/2002 | Barclay | |
| 7,144,723 B2 | 12/2006 | Fenical et al. | |
| 7,176,232 B2 | 2/2007 | Fenical et al. | |
| 7,179,834 B2 | 2/2007 | Fenical et al. | |
| 7,276,530 B2 | 10/2007 | Potts et al. | |
| 7,572,606 B1 | 8/2009 | Lam et al. | |
| 7,575,912 B2 | 8/2009 | Hughes et al. | |
| 8,076,118 B2 | 12/2011 | Morris et al. | |
| 8,986,971 B2 * | 3/2015 | Lam ......................... | C12N 1/20 435/252.1 |
| 10,011,814 B2 * | 7/2018 | Lam ......................... | C12N 1/20 |
| 2005/0076850 A1 | 4/2005 | Morris et al. | |
| 2006/0264495 A1 | 11/2006 | Palladino et al. | |
| 2007/0004676 A1 | 1/2007 | Palladino et al. | |
| 2015/0159130 A1 | 6/2015 | Lam et al. | |

FOREIGN PATENT DOCUMENTS

| | | |
|---|---|---|
| WO | WO 2005/002572 A2 | 1/2005 |
| WO | WO 2006/060809 A2 | 6/2006 |
| WO | WO 2006/118973 A2 | 11/2006 |
| WO | WO 2007/120801 A2 | 10/2007 |

(Continued)

OTHER PUBLICATIONS

Amberlite XAD 16 Product Data Sheet; Available from Rohm & Haas Corporation; Doc. No. PDS 0170 A—Oct. 3—Apr.

(Continued)

*Primary Examiner* — Deborah K Ware
(74) *Attorney, Agent, or Firm* — Cooley LLP

(57) ABSTRACT

Growth medium are disclosed for use in fermenting a marine microorganism. The medium comprise Potassium, Calcium, Strontium, Borate and Fluoride at specific concentrations. Alternatively, the growth medium comprises cobalt at specified concentrations or comprises vitamin $B_{12}$ at specified concentrations. Methods of producing certain desired compound by fermentation of a marine microorganism are also disclosed.

11 Claims, No Drawings

(56) References Cited

FOREIGN PATENT DOCUMENTS

WO    WO 2007/130404 A1    11/2007

OTHER PUBLICATIONS

Diaion Manual of Ion Exchange Resins and Synthetic Adsorbent, Part 2, Table of Contents; (Mitsubishi Chemical Corporation Separation Materials Department 1995) 1961.
Diaion Manual of Ion Exchange Resins and Synthetic Adsorbent, Part 1 pp. 157-171 & pp. 203-219 & Table of Contents; (Mitsubishi Chemical Corporation Separation Materials Department 1995) 1961.
Lam, K.S. et al., Effect of Neutral Resins on the Production of Dynemicins by Micromonospora Chersina, Journal of Industrial Microbiology (1995) 15, 453-456.
Notice of Allowability from U.S. Pat. No. 7,144,723 (U.S. Appl. No. 09/991,518).
Office Action from U.S. Pat. No. 7,144,723 (U.S. Appl. No. 09/991,518) dated Feb. 24, 2004 and response as filed.
Office Action from U.S. Pat. No. 7,144,723 (U.S. Appl. No. 09/991,518) dated Aug. 20, 2004 and response as filed.
Office Action from U.S. Pat. No. 7,144,723 (U.S. Appl. No. 09/991,518) dated Jun. 15, 2004 and response as filed.
Office Action from U.S. Pat. No. 7,144,723 (U.S. Appl. No. 09/991,518) dated Jun. 3, 2003 and response as filed.
Office Action from U.S. Pat. No. 7,144,723 (U.S. Appl. No. 09/991,518) dated Sep. 15, 2003 and response as filed.
Office Action from U.S. Pat. No. 7,144,723 (U.S. Appl. No. 09/991,518) dated Feb. 15, 2005 and response as filed.
Office Action from U.S. Pat. No. 7,144,723 (U.S. Appl. No. 09/991,518) dated Jun. 27, 2005 and response as filed.
Office Action from U.S. Pat. No. 7,144,723 (U.S. Appl. No. 09/991,518) dated Nov. 5, 2005 and response as filed.
Request for Certificate of Correction as filed in U.S. Pat. No. 7,144,723 (U.S. Appl. No. 09/991,518).
Response to Notice of Allowance as filed on Jul. 6, 2006 in U.S. Pat. No. 7,144,723 (U.S. Appl. No. 09/991,518).
Selecting the Right Amberlite XAD Adsorbent and linked chart; Available at http://www.advanced biosciences.com/xad_selection.htm; http://www.advancedbiosciences.com/xad_chart.htm; printed on Feb. 26, 2008.
Material Safety Data Sheet, "Instant Ocean Sea Salt," 2013, 4 pages.
Wikipedia—Rhodococcus rhodochrous, 2016, 1 page.

\* cited by examiner

SALT FORMULATIONS FOR THE FERMENTATION OF MARINE MICROORGANISMS

RELATED APPLICATIONS

The application is a divisional of U.S. application Ser. No. 14/624,183, filed Feb. 17, 2015, patented as U.S. Pat. No. 10,011,814 on Jul. 3, 2018, which is a divisional of U.S. application Ser. No. 11/860,491, filed Sep. 24, 2007 and patented as U.S. Pat. No. 8,986,971 on Mar. 24, 2015, which claims priority to U.S. Provisional Application No. 60/846,774, filed Sep. 22, 2006, and U.S. Provisional Application No. 60/949,147, filed Jul. 11, 2007, and U.S. Provisional Application Nos. 60/952,349 and 60/952,368, both filed Jul. 27, 2007. Each of these applications is incorporated herein, in its entirety, by reference.

BACKGROUND OF THE INVENTION

Field of the Invention

The present invention relates to methods of culturing microorganisms, in particular to systems, formulations and methods for the production of marine-derived microorganisms and compounds that they produce.

Description of the Related Art

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Similarly, infectious diseases caused, for example, by bacteria, fungi and protozoa are becoming increasingly difficult to treat and cure. For example, more and more bacteria, fungi and protozoa are developing resistance to current antibiotics and chemotherapeutic agents. Examples of such microbes include *Bacillus, Leishmania, Plasmodium* and *Trypansoma*.

Furthermore, a growing number of diseases and medical conditions are classified as inflammatory diseases. Such diseases include conditions such as asthma to cardiovascular diseases. These diseases continue to affect larger and larger numbers of people worldwide despite new therapies and medical advances.

Therefore, a need exists for additional chemotherapeutics, anti-microbial agents, and anti-inflammatory agents to treat cancer, inflammatory diseases and infectious disease. A continuing effort is being made by individual investigators, academia and companies to identify new, potentially useful chemotherapeutic and anti-microbial agents.

Marine-derived natural products are a rich source of potential new anti-cancer agents and anti-microbial agents. The oceans are massively complex and house a diverse assemblage of microbes that occur in environments of extreme variations in pressure, salinity, and temperature. Marine microorganisms have therefore developed unique metabolic and physiological capabilities that not only ensure survival in extreme and varied habitats, but also offer the potential to produce metabolites that would not be observed from terrestrial microorganisms (Okami, Y. 1993 *J Mar Biotechnol* 1:59). Representative structural classes of such metabolites include terpenes, peptides, polyketides, and compounds with mixed biosynthetic origins. Many of these molecules have demonstrable anti-tumor, anti-bacterial, anti-fungal, anti-inflammatory or immunosuppressive activities (Bull, A. T. et al. 2000 *Microbial Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Moore, B. S. 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating invaluable therapeutic agents. Further, the isolation of novel anti-cancer and anti-microbial agents that represent alternative mechanistic classes to those currently on the market will help to address resistance concerns, including any mechanism-based resistance that may have been engineered into pathogens for bioterrorism purposes.

SUMMARY OF THE INVENTION

In one embodiment, the invention relates to a growth medium for use in fermenting a marine microorganism, the medium comprising (a) Potassium ion at a concentration between 5 mMole/L and 13 mMole/L; (b) Calcium species at a concentration between 1.8 mMole/L and 6.3 mMole/L; (c) Strontium ion at a concentration between 0.03 mMole/L and 0.32 mMole/L; (d) Borate species at a concentration between 0.16 mMole/L and 0.81 mMole/L; and (e) Fluoride ion at a concentration between 0.02 mMole/L and 0.11 mMole/L.

In another embodiment, the invention relates to a growth medium for use in fermenting a marine microorganism, the medium comprising cobalt ion at a concentration between 0.2 μMole/L and 1.9 μMole/L. In another embodiment, this medium comprises vitamin $B_{12}$ at a concentration between 0.05 mg/L and 5 mg/L.

In another embodiment, the invention relates to a salt formulation for use in fermenting a marine microorganism, the formulation comprising: NaCl in the salt formulation at a mass percent between 96% and 80%; KCl in the salt formulation at a mass percent between 5% and 1.50%; $CaCl_2$ in the salt formulation at a mass percent between 3% and 1%; $SrCl_2$ in the salt formulation at a mass percent between 0.10% and 0.025%; $H_3BO_3$ in the salt formulation at a mass percent between 0.20% and 0.04%; and NaF in the salt formulation at a mass percent between 0.05% and 0.005%.

In another embodiment, the invention relates to a salt formulation for use in fermenting a marine microorganism, the formulation comprising: $Na_2SO_4$ at a mass percent between 95% and 90%; KCl at a mass percent between 8% and 6%; $CaCl_2$ at a mass percent between 5% and 3%; $SrCl_2$ at a mass percent between 0.15% and 0.05%; $H_3BO_3$ at a mass percent between 0.30% and 0.10%; and NaF at a mass percent between 0.03% and 0.01%.

In another embodiment, the invention relates to a salt formulation for use in fermenting a marine microorganism, the formulation comprising: KCl at a mass percent between 70% and 50%; $CaCl_2$ at a mass percent between 45% and 30%; $SrCl_2$ at a mass percent between 3% and 1%; $H_3BO_3$ at a mass percent between 3% and 1%; and NaF at a mass percent between 0.3% and 0.1%.

In another embodiment, the invention relates to a method of fermenting a marine microorganism, the method comprising:
(a) preparing a salt solution comprising:
(i) KCl concentration between 400 mg/L and 1 g/L;
(ii) $CaCl_2$ concentration between 200 mg/L and 700 mg/L;
(iii) $SrCl_2$ concentration between 5 mg/L and 50 mg/L;
(iv) $H_3BO_3$ concentration between 10 mg/L and 50 mg/L; and
(v) NaF concentration between 1 mg/L and 5 mg/L.
(b) adding a carbon source;
(c) adding a nitrogen source;
(d) adding a member of the group consisting of NaCl at a concentration between 5 g/L and 30 g/L, $Na_2SO_4$ at a concentration between 10 g/L and 40 g/L, and KCl at a concentration between 25 g/L and 35 g/L; and
(e) adding the microorganism.

In another embodiment, the invention relates to a method of producing a desired compound by fermentation of a marine microorganism, the method comprising adding $CoCl_2$ to a medium for growing the microorganism, wherein the amount of $CoCl_2$ added is sufficient to increase the amount of the desired compound produced and reduce the amount of an undesired compound produced relative to the amounts produced in the absence of $CoCl_2$.

In another embodiment, the invention relates to a method of producing salinosporamide A, comprising the steps of preparing a microbial growth media; inoculating said media with a strain of microorganism capable of producing salinosporamide A; adding a resin to the media before 96 hours after inoculation of the medium. In another embodiment of the resin is added before 24 hours after inoculation of the medium.

In another embodiment, the invention relates to a method of producing a proteasome inhibitor comprising culturing *Salinospora tropica* in the presence of Amberlite XAD-7 resin.

In another embodiment, the invention relates to a method of producing a compound of Formula A, wherein R1 is selected from the group consisting of hydrogen and hydroxide, R2 is selected from the group consisting of 2-chloroethyl, 2-hromoethyl, ethyl, methyl, and propyl, and R3 is selected from the group consisting of methyl and ethyl, comprising the steps of growing a culture of *S. tropica* in the presence of XAD-7 resin.

Formula A

In another embodiment, the invention relates to a method of producing a compound of Formula B, wherein R1 is selected from the group consisting of hydrogen and hydroxide, R2 is selected from the group consisting of 2-chloroethyl, 2-bromoethyl, ethyl, methyl, and propyl, and R3 is selected from the group consisting of methyl and ethyl, comprising the steps of growing a culture of *S. tropica* in the presence of XAD-7 resin.

Formula B

In another embodiment, the invention relates to a method of producing a compound of Formula C, wherein R2 is selected from the group consisting of 2-chloroethyl and methyl, comprising the steps of growing a culture of *S. tropica* in the presence of XAD-7 resin.

Formula C

DETAILED DESCRIPTION OF THE PREFERRED EMBODIMENT

The production of marine derived natural products can be carried out by cultivating the microorganism that produces the compound in a suitable nutrient medium, in either aerobic or anaerobic conditions, until a substantial amount of desired compound is detected in the media. The compound can then be harvested from the media with a suitable solvent, concentrating the desired compound.

Various separation techniques, well known in the art, can be used to isolate the desired compound, separating it from other metabolites also present in the cultivation medium. Separation of the desired compound from other co-harvested metabolites leads to a decrease in the net yield of the desired compound. The reduction of other metabolites produced by the microorganism would result in a higher net yield of the desired compound due to decreased loss during the separation process. Reduction of other metabolites produced by the microorganism may also result in increased production of the desired metabolite.

It has been discovered that varying the concentrations of particular salts in the growth media of microorganisms may reduce the production of analog metabolites and increase the production of the desired compound. Accordingly, some embodiments include salt formulations that are optimized to increase production of a desired compound and decrease production of undesired metabolites. Furthermore, commercially available sea salt formulations have component variability that is unsuitable for meeting the quality control requirements of pharmaceutical manufacture. Accordingly, some embodiments include salt formulations optimized for the production pharmaceutical agents from marine fermentation.

Growth of marine-derived microorganisms is achieved by the use of appropriate medium. Broadly, medium suitable to cultivate the microorganisms includes a carbon source, a nitrogen source, and nutrient inorganic salts. In some cases, a seed culture is first grown in a seed medium followed by inoculation into a production medium. Broadly, the sources of carbon in the seed and production mediums may include glucose, fructose, mannose, maltose, galactose, mannitol, and/or glycerol, other sugars and/or sugar alcohols, starches and/or other carbohydrates, or carbohydrate derivatives such as dextran, cerelose, as well as complex nutrients such as oat flour, corn meal, millet, corn, and the like. The exact quantity of the carbon source that is utilized in the medium will depend in part, upon the other ingredients in the medium, but an amount of carbohydrate between 0.5 to 25 percent by weight of the medium can be satisfactorily used, for example. These carbon sources can be used individually or several such carbon sources can be combined in the same medium, for example.

The sources of nitrogen include amino acids such as glycine, arginine, threonine, methionine and the like, ammonium salt, as well as complex sources such as yeast extracts, corn steep liquors, distiller solubles, soybean meal, cottonseed meal, fish meal, peptone, and the like. The various sources of nitrogen can be used alone or in combination in amounts ranging from 0.5 to 25 percent by weight of the medium, for example.

Among the nutrient inorganic salts, which can be incorporated in the culture media, are the customary salts capable of yielding sodium, potassium, magnesium, calcium, phosphate, sulfate, chloride, carbonate, and like ions. Also included may be trace metals such as cobalt, manganese, iron, molybdenum, zinc, cadmium, and the like. Some of these salts may be part of a vegetative or fermentation media, for example, a commercially available vegetative or fermentation media. Other salts may be provided in a prepared salt formulation, Commercially available sea salt formulations may include INSTANT OCEAN®, Aquarium Systems, Inc., Wicklife Ohio. However, in some embodiments, a salt formulation is provided that is optimized for the production of a pharmaceutical agent.

In one embodiment, a salt formulation is provided comprising NaCl, $MgSO_4$, KBr, KCl, $CaCO_3$, $CaCl_2$, $SrCl_2$, $H_3BO_3$, and NaF salts. In one embodiment, this salt formulation is optimized for use in a seed medium. In one embodiment, the salt formulation is provided as a mixture of solid salts. In one such embodiment the percent mass of NaCl in the solid salt is between 99% and 1%. In another embodiment the percent mass of NaCl in the solid salt is between 95% and 10%. In another embodiment the percent mass of NaCl in the solid salt is between 90% and 30%. In another embodiment the percent mass of NaCl in the solid salt is between 88% and 60%. In another embodiment the percent mass of NaCl in the solid salt is between 85% and 75%. In the preferred embodiment the percent mass of NaCl in the solid salt is about 80%. In one embodiment the percent mass of $MgSO_4.7H_2O$ in the solid salt is between 90% and 0.1%. In another embodiment the percent mass of $MgSO_4.7H_2O$ in the solid salt is between 70% and 1%. In another embodiment the percent mass of $MgSO_4.7H_2O$ in the solid salt is between 40% and 5%. In another embodiment the percent mass of $MgSO_4.7H_2O$ in the solid salt is between 20% and 10%. In the preferred percent mass of $MgSO_4.7H_2O$ in the solid salt is about 14%. In one embodiment the percent mass of KBr in the solid salt is between 10% and 0.01%. In another embodiment the percent mass of KBr in the solid salt is between 5% and 0.05%. In another embodiment the percent mass of KBr in the solid salt is between 3% and 0.10%. In another embodiment the percent mass of KBr in the solid salt is between 1% and 0.20%. In the preferred embodiment the percent mass of KBr in the solid salt is 0.30%. In one embodiment the percent mass of KCl in the solid salt is between 90% and 0.10%. In another embodiment the percent mass of KCl in the solid salt is between 40% and 0.50%. In another embodiment the percent mass of KCl in the solid salt is between 20% and 1%. In another embodiment the percent mass of KCl in the solid salt is between 5% and 1.50%. In the preferred embodiment the percent mass of KCl in the solid salt is about 2.5. In one embodiment the percent mass of $CaCO_3$ in the solid salt is between 70% and 0.10%. In another embodiment the percent mass of $CaCO_3$ in the solid salt is between 40% and 0.25%. In another embodiment the percent mass of $CaCO_3$ in the solid salt is between 20% and 0.50%. In another embodiment the percent mass of $CaCO_3$ in the solid salt is between 5% and 1%. In the preferred embodiment the percent mass of $CaCO_3$ in the solid salt is about 1.5%. In one embodiment the percent mass of $CaCl_2$ in the solid salt is between 70% and 0.10%. In another embodiment the percent mass of $CaCl_2$ in the solid salt is between 40% and 0.25%. In another embodiment the percent mass of $CaCl_2$ in the solid salt is between 20% and 0.50%. In another embodiment the percent mass of $CaCl_2$ in the solid salt is between 5% and 1%. In the preferred embodiment the percent mass of $CaCl_2$ in the solid salt is about 1.5%. In one embodiment the percent mass of $SrCl_2$ in the solid salt is between 20% and 0.001%. In another embodiment the percent mass of $SrCl_2$ in the solid salt is between 5% and 0.005%. In another embodiment the percent mass of $SrCl_2$ in the solid salt is between 1% and 0.01%. In another embodiment the percent mass of $SrCl_2$ in the solid salt is between 0.10% and 0.025%. In the preferred embodiment the percent mass of $SrCl_2$ in the solid salt is about 0.05%. In one embodiment the percent mass of $H_3BO_3$ in the solid salt is between 20% and 0.001%. In another embodiment the percent mass of $H_3BO_3$ in the solid salt is between 5% and 0.005%. In another embodiment the percent mass of $H_3BO_3$ in the solid salt is between 1% and 0.01%. In another embodiment the percent mass of $H_3BO_3$ in the solid salt is between 0.10% and 0.04%. In the preferred embodiment the percent mass of $H_3BO_3$ in the solid salt is about 0.07%. In one embodiment the percent mass of NaF in the solid salt is between 10% and 0.0001%. In another embodiment the percent mass of NaF in the solid salt is between 2% and 0.001%, In another embodiment the percent mass of NaF in the solid salt is between 0.5% and 0.003%. In another embodiment the percent mass of NaF in the solid salt is between 0.05% and 0.005%. In the preferred embodiment the percent mass of NaF in the solid salt is about 0.01%. In one embodiment NaF in the solid salt is replaced by KF in the solid salt between 10% and 0.0001%. In another embodiment the percent mass of KF in the solid salt is between 2% and 0.001%. In another embodiment the percent mass of KF in the solid salt is between 0.5% and 0.003%. In another embodiment the percent mass of KF in the solid salt is between 0.05% and 0.005%. In the preferred embodiment the percent mass of KF in the solid salt is about 0.01%.

In another embodiment, the salt formulation is provided as a solution in water. In one such embodiment the NaCl concentration is between 100 mg/L and 200 g/L. In another embodiment the NaCl concentration is between 1 g/L and 50 g/L. In another embodiment the NaCl concentration is between 10 g/L and 40 g/L. In another embodiment the NaCl concentration is between 20 g/L, and 30 g/L. In the preferred embodiment the NaCl concentration is about 25 g/L. In one embodiment the $MgSO_4.7H_2O$ concentration is between 10 mg/L and 100 g/L. In another embodiment the $MgSO_4.7H_2O$ concentration is between 500 and 20 g/L. In another embodiment the $MgSO_4.7H_2O$ concentration is between 1 g/L and 10 g/L. In another embodiment the $MgSO_4.7H_2O$ concentration is between 2 g/L and 6 g/L. In the preferred embodiment the $MgSO_4.7H_2O$ concentration is about 4 g/L. In one embodiment the KBr concentration is between 1 mg/L and 2 g/L. In another embodiment the KBr concentration is between 5 mg/L and 400 mg/L. In another embodiment the KBr concentration is between 20 mg/L and 200 mg/L. In another embodiment the KBr concentration is between 70 mg/L and 100 mg/L. In the preferred embodiment the KBr concentration is about 85 mg/L. In one embodiment the KCl concentration is between 10 mg/L and 100 g/L. In another embodiment the KCl concentration is between 50 mg/L and 20 g/L. In another embodiment the KCl concentration is between 200 mg/L and 5 g/L. In another embodiment the KCl concentration is between 400 mg/L and 1 g/L. In another embodiment the KCl concentration is between 650 mg/L and 750 g/L. In the preferred embodiment the KCl concentration is about 700 mg/L. In one embodiment the $CaCO_3$ concentration is between 1 mg/L and 10 g/L. In another embodiment the $CaCO_3$ concentration is between 10 mg/L and 5 g/L. In another embodiment the $CaCO_3$ concentration is between 100 mg/L and 1 g/L. In another embodiment the $CaCO_3$ concentration is between 200 mg/L and 700 mg/L. In another embodiment the $CaCO_3$ concentration is between 400 mg/L and 500 mg/L. In the preferred embodiment the $CaCO_3$ concentration is about 450 mg/L. In one embodiment the $CaCl_2$ concentration is between 1 mg/L and 10 g/L. In another embodiment the $CaCl_2$ concentration is between 10 mg/L and 5 g/L. In another embodiment the $CaCl_2$ concentration is between 100 mg/L and 1 g/L. In another embodiment the $CaCl_2$ concentration is between 200 tng/L and 700 mg/L. In another embodiment the $CaCl_2$ concentration is between 40 mg/L and 500 mg/L. In the preferred embodiment the $CaCl_2$ concentration is about 450 mg/L. In one embodiment the $SrCl_2$ concentration is between 0.1 mg/L and 1.0 g/L. In another embodiment the $SrCl_2$ concentration is between 0.5 mg/L and 1 g/L. In another embodiment the $SrCl_2$ concentration is between 1 mg/L and 500 mg/L. In another embodiment the $SrCl_2$ concentration is between 5 mg/L and 50 mg/L. In another embodiment the $SrCl_2$ concentration is between 10 mg/L and 20 mg/L. In the preferred embodiment the $SrCl_2$ concentration is about 15 mg/L. In one embodiment the $H_3BO_3$ concentration is between 0.1 mg/L and 10 g/L. In another embodiment the $H_3BO_3$ concentration is between 0.5 mg/L and 2 g/L. In another embodiment the $H_3BO_3$ concentration is between 2 mg/L and 500 mg/L. In another embodiment the $H_3BO_3$ concentration is between 10 mg/L and 50 mg/L. In another embodiment the $H_3BO_3$ concentration is between 15 mg/L and 25 mg/L. In the preferred embodiment the $H_3BO_3$ concentration is about 20 mg/L. In one embodiment the NaF concentration is between 0.05 mg/L and 500 mg/L. In another embodiment the NaF concentration is between 0.25 mg/L, and 100 mg/L in another embodiment the NaF concentration is between 0.50 mg/L, and 50 mg/L. In another embodiment the NaF concentration is between 1 mg/L, and 5 mg/L. In the preferred embodiment the NaF concentration is about 3 mg/L. In one embodiment the NaF is replaced by KF using concentration between 0.05 mg/L and 500 mg/L. In another embodiment the KF concentration is between 0.25 mg/L and 100 mg/L. In another embodiment the KF concentration is between 0.50 mg/L and 50 mg/L. In another embodiment the KF concentration is between 1 mg/L and 5 mg/L. In the preferred embodiment the KF concentration is about 3 mg/L.

In another embodiment, a salt formulation is provided comprising NaCl, KCl, $CaCl_2$, $SrCl_2$, $H_3BO_3$, and NaF salts. In one embodiment, this salt formulation is optimized for use in a production medium. In one embodiment, the salt formulation is provided as a mixture of solid salts. In one such embodiment the percent mass of NaCl in the solid salt is between 99.9% and 1%. In another embodiment the percent mass of NaCl in the solid salt is between 99% and 10%. In another embodiment the percent mass of NaCl in the solid salt is between 97% and 50%. In another embodiment the percent mass of NaCl in the solid salt is between 96% and 80%. In another embodiment the percent mass of NaCl in the solid salt is between 96% and 90%. In the preferred embodiment the percent mass of NaCl in the solid salt is about 95%. In one embodiment the percent mass of KCl in the solid salt is between 90% and 0.10%. In another embodiment the percent mass of KCl in the solid salt is between 40% and 0.50%. In another embodiment the percent mass of KCl in the solid salt is between 20% and 1%. In another embodiment the percent mass of KCl in the solid salt is between 5% and 1.50%. In the preferred embodiment the percent mass of KCl in the solid salt is about 2.5%. In one embodiment the percent mass of $CaCl_2$ in the solid salt is between 70% and 0.10%. In another embodiment the percent mass of $CaCl_2$ in the solid salt is between 40% and 0.25%. In another embodiment the percent mass of $CaCl_2$ in the solid salt is between 10% and 0.50%. In another embodiment the percent mass of $CaCl_2$ in the solid salt is between 3% and 1%. In the preferred embodiment the percent mass of $CaCl_2$ in the solid salt is 1.7%. In one embodiment the percent mass of $SrCl_2$ in the solid salt is between 20% and 0.001%. In another embodiment the percent mass of $SrCl_2$ in the solid salt is between 5% and 0.005%. In another embodiment the percent mass of $SrCl_2$ in the solid salt is between 1% and 0.01%. In another embodiment the percent mass of $SrCl_2$ in the solid salt is between 0.1.0% and 0.025%. In the preferred embodiment the percent mass of $SrCl_2$ in the solid salt is about 0.06%. In one embodiment the percent mass of $H_3BO_3$ in the solid salt is between 20% and 0.001%. In another embodiment the percent mass of $H_3BO_3$ in the solid salt is between 5% and 0.005%. In another embodiment the percent mass of $H_3BO_3$ in the solid salt is between 1% and 0.01%. In another embodiment the percent mass of $H_3BO_3$ in the solid salt is between 0.20% and 0.04%. In the preferred embodiment the percent mass of $H_3BO_3$ in the solid salt is about 0.09%. In one embodiment the percent mass of NaF in the solid salt is between 10% and 0.0001%. In another embodiment the percent mass of NaF in the solid salt is between 2% and 0.001%. In another embodiment the percent mass of NaF in the solid salt is between 0.5% and 0.003%. In another embodiment the percent mass of NaF in the solid salt is between 0.1% and 0.005%. In the preferred embodiment the percent mass of NaF in the solid salt is about 0.01%. In one embodiment the percent mass of NaF in the solid salt is replaced by KF between 10% and 0.0001%. In another embodiment the percent mass of KF in the solid salt is between 2% and 0.001%. In another embodiment the percent mass of KF in the solid salt is between 0.5% and 0.003%. In another embodiment the percent mass of KF in the solid salt is between 0.1% and 0.005%. In the preferred embodiment the percent mass of KF in the solid salt is about 0.01%.

In another embodiment, the salt formulation is provided as a solution in water. In one such embodiment the NaCl concentration is between 100 mg/L and 200 g/L. In another embodiment the NaCl concentration is between 1 g/L and 50 g/L. In another embodiment the NaCl concentration is between 10 g/L and 40 g/L. In another embodiment the NaCl concentration is between 20 g/L and 30 g/L. In the preferred embodiment the NaCl concentration is about 25 g/L. In one embodiment the KCl concentration is between 10 mg/L and 100 g/L. In another embodiment the KCl concentration is between 50 mg/L and 20 g/L. In another embodiment the KCl concentration is between 200 mg/L and 5 g/L. In another embodiment the KCl concentration is between 400 mg/L and 1 g/L. In another embodiment the KCl concentration is between 600 mg/L and 800 mg/L. In the preferred embodiment the KCl concentration is about 700 mg/L. In one embodiment the $CaCl_2$ concentration is between 1 mg/L and 10 g/L. In another embodiment the $CaCl_2$ concentration is between 10 mg/L and 5 g/L. In another embodiment the $CaCl_2$ concentration is between 100 mg/L and 1 g/L. In another embodiment the $CaCl_2$ concentration is between 200 mg/L and 700 mg/L. In another embodiment the $CaCl_2$ concentration is between 400 mg/L and 500 mg/L. In the preferred embodiment the $CaCl_2$ concentration is about 450 mg/L. In one embodiment the $SrCl_2$ concentration is between 0.1 mg/L and 10 g/L. In another embodiment the $SrCl_2$ concentration is between 0.5 mg/L and 1 g/L. In another embodiment the $SrCl_2$ concentration is between 1 mg/L and 500 mg/L. In another embodiment the $SrCl_2$ concentration is between 5 mg/L, and 50 mg/L. In another embodiment the $SrCl_2$ concentration is between 10 mg/L and 20 mg/L. In the preferred embodiment the $SrCl_2$ concentration is about 15 mg/L. In one embodiment the $H_3BO_3$ concentration is between 0.1 mg/L and 10 g/L. In another embodiment the $H_3BO_3$ concentration is between 0.5 mg/L and 2 g/L. In another embodiment the $H_3BO_3$ concentration is between 2 mg/L and 500 mg/L. In another embodiment the $H_3BO_3$ concentration is between 10 mg/L and 50 mg/L. In another embodiment the $H_3BO_3$ concentration is between 15 mg/L and 25 mg/L. In the preferred embodiment the $H_3BO_3$ concentration is about 20 mg/L. In one embodiment the NaF concentration is between 0.05 mg/L and 500 mg/L. In another embodiment the NaF concentration is between 0.25 mg/L and 100 mg/L. In another embodiment the NaF concentration is between 0.50 mg/L, and 50 mg/L. In another embodiment the NaF concentration is between 1 mg/L and 5 mg/L. In the preferred embodiment the NaF concentration is about 3 mg/L. In one embodiment the NaF concentration is replaced by KF and is between 0.05 mg/L and 500 mg/L. In another embodiment the KF concentration is between 0.25 mg/L and 100 mg/L. In another embodiment the KF concentration is between 0.50 mg/L and 50 mg/L. In another embodiment the KF concentration is between 1 mg/L and 5 mg/L. In the preferred embodiment the KF concentration is about 3 mg/L.

In some alternative embodiments of the above salt formulations, no NaCl is added. Excluding NaCl results in a formulation that is less corrosive to fermentation vessels. In one embodiment $Na_2SO_4$ is added at a concentration between 100 mg/L, and 200 g/L to replace NaCl. In another embodiment $Na_2SO_4$ is added at a concentration between 1 g/L, and 50 g/L to replace NaCl. In one embodiment $Na_2SO_4$ is added at a concentration between 5 g/L and 30 g/L to replace NaCl. In one embodiment $Na_2SO_4$ is added at a concentration between 10 g/L and 20 g/L to replace NaCl. In the preferred embodiment where $Na_2SO_4$ is added to replace NaCl, the $Na_2SO_4$ concentration is about 20 g/L.

In another embodiment of the above salt formulations for seed or production media, the sodium ion level is reduced. Embodiments may use, for example, potassium salts or potassium salts and sulfate salts along with other nutrient and environmental salts. In one embodiment, KCl is between 1 mg/L and 100 g/L. In another embodiment, the KCl is between 100 mg/L and 60 g/L. In another embodiment, the KCl is between 2 g/L and 45 g/L. In another embodiment $MgSO_4$ is present in the medium. In one embodiment, the $MgSO_4$ is supplied at least in part through addition of $MgSO_4.7H_2O$. In one embodiment, the $MgSO_4.7H_2O$ is between 1 mg/L and 20 g/L. In another embodiment, the $MgSO_4.7H_2O$ is between 500 mg/L and 15 g/L. In another embodiment, the $MgSO_4.7H_2O$ is between 2 and 8 g/L. In other embodiments, potassium ions and sulfate ions can be supplied by combining any of the above additions.

In another embodiment of the above salt formulations for seed and production media, the chloride ion level is reduced. Embodiments may use, for example, sulfate salts. The sulfate salts may be in the sodium, potassium, magnesium or other appropriate forms. The salts may or may not be hydrated. In various embodiments, $Na_2SO_4$ is between 10 mg/L and 60 g/L or between 500 mg/L and 45 g/L or between 3 g/L and 25 g/L. In other embodiments, $K_2SO_4$ is between 10 mg/L and 100 g/L or between 1 g/L and 75 or between 10 g/L and 60 g/L. In other embodiments, low sodium and low chloride ion levels can be achieved by combining formulations described above. In other embodiments, a low sodium or low chloride or low sodium and chloride formulation can be used for only the seed stage, only the production stage, less than all of the seed stages, or a combination of these alternatives.

Another embodiment includes the addition of a cobalt salt to a salt formulation such as the formulations described above. In some embodiments, cobalt salt may be added to a medium utilizing a commercially available salt formulation (e.g., INSTANT OCEAN®). In one embodiment, the cobalt salt is $CoCl_2$. In one embodiment the CoCl, concentration is between 1 µg/L and 20 mg/L. In another embodiment the $CoCl_2$ concentration is between 5 µg/L and 5 mg/L. In another embodiment the $CoCl_2$ concentration is between 10 µg/L and 1 mg/L. In another embodiment the $CoCl_2$ concentration is between 20 µg/L and 250 µg/L, In the preferred embodiment the $CoCl_2$ concentration is between 50 µg/L and 210 µg/L.

In one embodiment, the invention relates to a method of producing a marine microorganism, comprising the steps of:
preparing a microbial growth medium;
inoculating said medium with a strain of the microorganism;
adding a resin to the medium within 96 hours after inoculation of the medium.

The microorganism is preferably capable of producing Salinosporamide A.

In certain embodiments, the resin is added within 72 hours after inoculation of the medium.

In other embodiments, the resin is added within 48 hours after inoculation of the medium.

In other embodiments, the resin is added within 24 hours of inoculation of the medium.

In other embodiments, the resin is added prior to inoculation of the medium.

In other embodiment, the microorganism is of the genus *Salinispora*.

In certain embodiments, the microorganism is *Salinispora tropica*.

In other embodiments, the microorganism is *Salinispora tropica* NPS021184.

In another embodiment, the resin is an adsorption resin.

In another embodiment, the resin is an uncharged adsorption resin.

In another embodiment, the resin is a hydrophobic adsorption resin.

In another embodiment, the resin is at least partially composed of a material selected from the group consisting of polystyrenedivinylbenzene, aliphatic esters, a formophenolic matrix, a cross-linked styrenic matrix, a brominated cross-linked styrenic matrix, and a methacrylic ester copolymer.

In another embodiment, the resin includes at least one resin selected from the group consisting of Amberlite XAD2, Amberlite XAD4, Amberlite XAD7, Amberlite XAD7HP, Amberlite XAD16, Amberlite XAD761, Amberlite XAD 761, Amberlite XAD1180, Diaion HP2MG, Diaion HP20, Diaion HP21, Sepabeads SP825, Sepabeads SP850, Sepabeads SP70, Sepabeads SP700, and Sepabeads SP207.

In another embodiment, the resin includes at least one resin selected from the group consisting of Amberlite XAD2, Amberlite XAD4, Amberlite XAD7, Amberlite XAD7HP and Amberlite XAD16.

In another embodiment, the ratio of resin to total nitrogen added to the fermenter is 5:1 to 100:1.

In another embodiment, the ratio of resin to total nitrogen added to the fermenter is 10:1 to 60:1.

In another embodiment, the ratio of resin to total nitrogen added to the fermenter is 20:1 to 40:1.

In another embodiment, the ratio of resin to dry cell weight is 15:1 to 120:1.

In another embodiment, the ratio of resin to dry cell weight is 30:1 to 45:1.

Another aspect of the invention relates to a method of producing salinosporamide A, comprising culturing a salinosporamide A producing microorganism in the presence of Amberlite XAD-7 resin.

In one embodiment, the ratio of resin to total nitrogen added to the fermenter is 5:1 to 100:1.

In another embodiment, the ratio of resin to total nitrogen added to the fermenter is 10:1 to 60:1.

In another embodiment, the ratio of resin to total nitrogen added to the fermenter is 20:1 to 40:1.

In another embodiment, the ratio of resin to dry cell weight is 15:1 to 120:1.

In another embodiment, the ratio of resin to dry cell weight is 30:1 to 45:1.

Another aspect of the invention relates to a method of producing a proteasome inhibitor comprising culturing *Salinisporamide tropica* in the presence of Amberlite XAD-7 resin.

In one embodiment, XAD-7 resin is added to the fermentation vessel prior to inoculation of the media.

In another embodiment, XAD-7 resin is added after at least a portion of inoculum is added.

In another embodiment, at least a portion of the XAD-7 resin is added simultaneous to at least a portion of at least one non-water media component.

In another embodiment, a portion of at least one non-water media component is added to the fermentation vessel after at least a portion of the XAD-7 resin.

In another embodiment, XAD-7 resin is added in two or more portions.

In another embodiment, at least a portion of the XAD-7 resin is added substantially separate from non-water media components.

In another embodiment, XAD-7 resin is present at the end of the growth phase.

In another embodiment, XAD-7 resin is present cells are multiplying.

In another embodiment XAD-7 resin is added during the stationary phase.

In another embodiment, XAD-7 resin is present while cells are producing salinosporamide A.

Another aspect of the invention relates to a method of producing a
proteasome inhibitor, comprising the steps of
preparing a microbial growth medium;
inoculating said medium with *Salinispora tropica*;
adding a resin to the medium prior to 96 hours after inoculation of the medium.

In one embodiment, the resin is added prior to the onset of the stationary phase of growth.

Another aspect of the invention relates to a method of producing salinosporamide A, comprising culturing a salinosporamide A producing microorganism in the presence of a resin added prior to the fifth day of the fermentation.

In one embodiment, the salinosporamide producing microorganism is cultured in a fed-batch mode of operation.

Another aspect of the invention relates to a method of producing salinosporamide A, comprising culturing a salinosporamide A producing microorganism in the presence of a resin selected from the group consisting of Amberlite XAD2, Amberlite XAD4, Amberlite XAD7, Amberlite XAD7HP, Amberlite XAD761, Amberlite XAD 761, Amberlite XAD1180, Diaion HP2MG, Diaion HP20, Diaion 21, Sepabeads SP825, Sepabeads SP850, Sepabeads SP70, Sepabeads SP700, and Sepabeads SP207.

In one embodiment, the resin is added at intervals and these intervals may be pre-determined or otherwise based on observable criterion, such as the extent of cell growth.

In another embodiment, media components are added at intervals during the fermentation.

Another aspect of the invention relates to a method of producing a compound of Formula A, wherein R1 is selected from the group consisting of hydrogen and hydroxide, R2 is selected from the group consisting of 2-chloroethyl, 2-bromoethyl, ethyl, methyl, and propyl, and R3 is selected from the group consisting of methyl and ethyl, comprising the steps of growing a culture of *S. tropica* in the presence of XAD-7 resin.

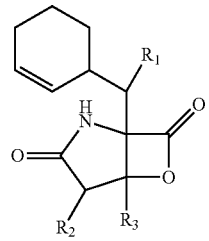

Formula A

Another aspect of the invention relates to a method of producing a compound of Formula B, wherein R1 is selected from the group consisting of hydrogen and hydroxide, R2 is selected from the group consisting of 2-chloroethyl, 2-bromoethyl, ethyl, methyl, and propyl, and R3 is selected from the group consisting of methyl and ethyl, comprising the steps of growing a culture of *S. tropica* in the presence of XAD-7 resin.
Formula B
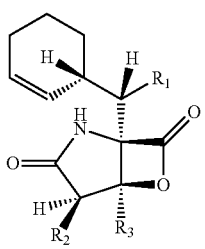

Another aspect of the invention relates to a method of producing a compound of Formula C, wherein R2 is selected from the group consisting of 2-chloroethyl and methyl, comprising the steps of growing a culture of *S. tropica* in the presence of XAD-7 resin.

Formula C

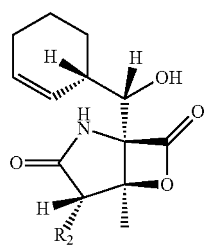

One class of marine-derived natural products are Salinosporamide A and analogs thereof. Salinosporamide A and its analogs have various biological activities. For example, the compounds have chemosensitizing activity, anti-microbial, anti-inflammation, radiosensitizing, and anti-cancer activity. Studies have been conducted that show Salinospormide A and its analogs have proteasome inhibitory activity, effect NF-κB/IκB signaling pathway, and have anti-anthrax activity. Salinosporamide A and several analogs, as well as biological activity of the same, are described in U.S. Provisional Patent Applications No. 60/480,270, filed Jun. 20, 2003; Ser. No. 60/566,952, filed Apr. 30, 2004; Ser. No. 60/627,461, filed Nov. 12, 2004; Ser. No. 60/633,379, filed Dec. 3, 2004; Ser. No. 60/643,922, filed Jan. 13, 2005; Ser. No. 60/658,884, filed Mar. 4, 2005; Ser. No. 60/676,533, filed Apr. 29, 2005; Ser. No. 60/567,336, filed Apr. 30, 2004; Ser. No. 60/580,838, filed Jun. 18, 2004; Ser. No. 60/591,190, filed Jul. 26, 2004; Ser. No. 60/627,462, filed Nov. 12, 2004; Ser. No. 60/644,132, filed Jan. 13, 2005; Ser. No. 60/659,385, filed. Mar. 4, 2005; Ser. No. 60/791,625, filed Apr. 13, 2006; Ser. No. 60/797,553, filed May 3, 2006; and Ser. No. 60/949,147, filed Jul. 11, 2007 (entitled "Use of Polyaciylic Resins in Fermentation of Marine Actinomycetes"); U.S. patent application Ser. No. 10/871,368, filed Jun. 18, 2004; Ser. No. 11/118,260, filed Apr. 29, 2005; Ser. No. 11/412,476, filed Apr. 27, 2006; Ser. No. 11/453,374, filed Jun. 15, 2006; Ser. No. 11/517,899, filed Sep. 8, 2006; and Ser. No. 11/697,689, filed Apr. 6, 2007 (entitled "Total Synthesis of Salinosporamide A and Analogs Thereof"); and International Patent Applications Nos., PCT/US2004/019543, filed Jun. 18, 2004; PCT/US2005/044091, filed Dec. 2, 2005; PCT/US2005/014846, filed Apr. 29, 2005; and PCT/US2006/016104, filed Apr. 27, 2006; each of which is hereby incorporated by reference in its entirety.

Compounds

One aspect of the invention relates to producing various useful chemical compounds which are made by strains of a *S. tropica* microorganism. Below are exemplary compounds:

Formula D

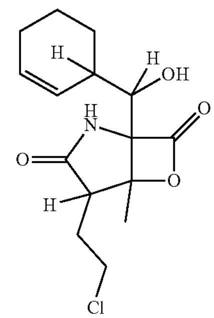

Formula E

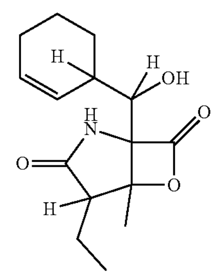

Formula E

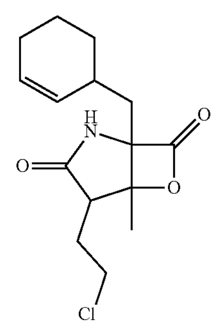

Formula G

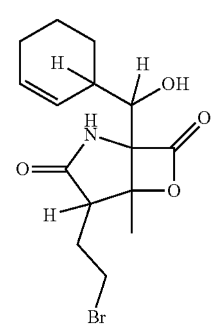

Formula F

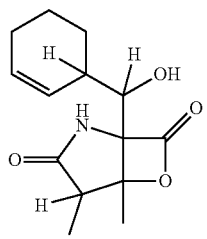

Formula G

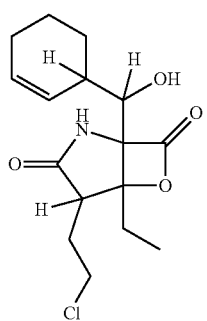

Various embodiments of compounds having the structure disclosed in the above Formulae include optically active compounds. One of these is Salinosporamide A, the structure of which is shown below:

Compound 1

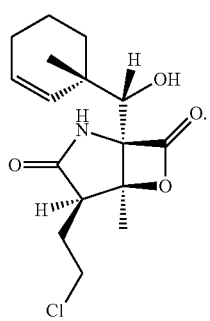

Salinosporamide A

Among its properties is its ability to inhibit the production of proteasomes. Proteasome inhibitors have applicability, among other things, in the treatment of cancers. This activity is more fully described in PCT Application Publication No. WO/2006/118973, filed Apr. 27, 2006, which is incorporated herein by reference in its entirety.

Other exemplary embodiments of useful compounds produced by *S. tropica*, which correspond to the formulae described above are identified below by structure indicating some exemplary stereo-isomers:

Compound 2

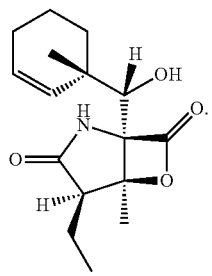

Salinosporamide B.

Compound 3

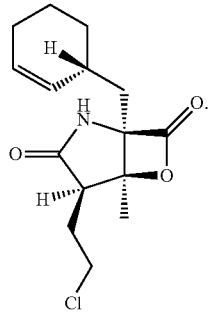

Compound 4

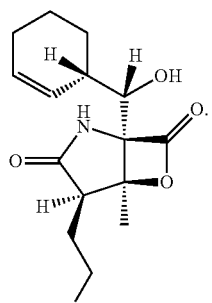

Compound 5

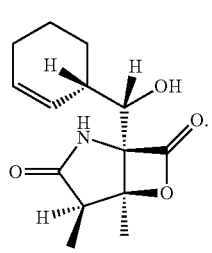

Compound 6

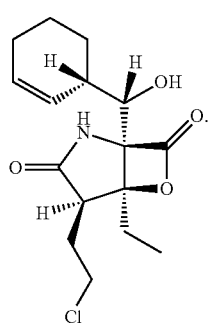

-continued

Compound 7

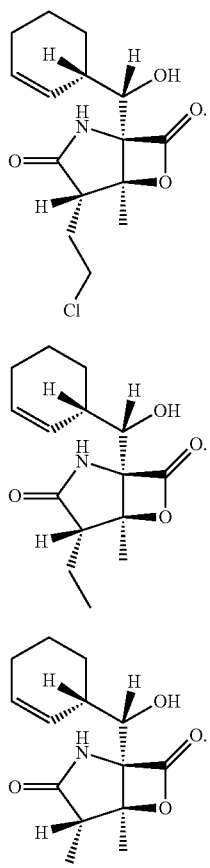

Compound 8

Compound 9

Compounds that correspond to the structures of the above formula can exist as different stereo-isomers and should not be limited to individual forms. For example, Compounds 1 and 7 are two of several stereo isomers of Formula D. Similarly, Compounds 2 and 8 as well as Compounds 5 and 9 are exemplary stereo isomers of the same Formula structures. Additional optical forms of the Formulae are also contemplated.

Among the useful properties of these compounds are also proteasome inhibition and the treatment of various diseases including cancers.

Each of these compounds can be used alone or in combination with one or more other compounds produced by S. tropica, or in combination with other compounds from other sources. Additionally, each of these compounds can be chemically modified to change their properties.

The production of Salinosporamide A and analogs thereof can be carried out by cultivating Salinispora tropica strain NPS021184, ATCC accession number PTA-6685, a natural variant of strain CNB476, in a suitable nutrient medium under conditions described herein, preferably under submerged aerobic conditions, until a substantial amount of compounds are detected in the fermentation; harvesting by extracting the active components from the fermentation broth with a suitable solvent; concentrating the solvent containing the desired components; then subjecting the concentrated material to chromatographic separation to isolate the compounds from other metabolites also present in the cultivation medium.

In the fermentative production of Salinosporamide A by Salinispora tropica NPS021184, two analogs of Salinosporamide A, NPI-0047, also referred to as Salinosporamide B, and NPI-2065, are co-produced in the fermentation. The separation of NPI-0047 from Salinispora A results in loss of the recovery yield of Salinosporamide A. Subsequently, removing NPI-2065 from Salinosporamide A leads to further loss in recovery yield. The structure for each of these compounds is shown below:

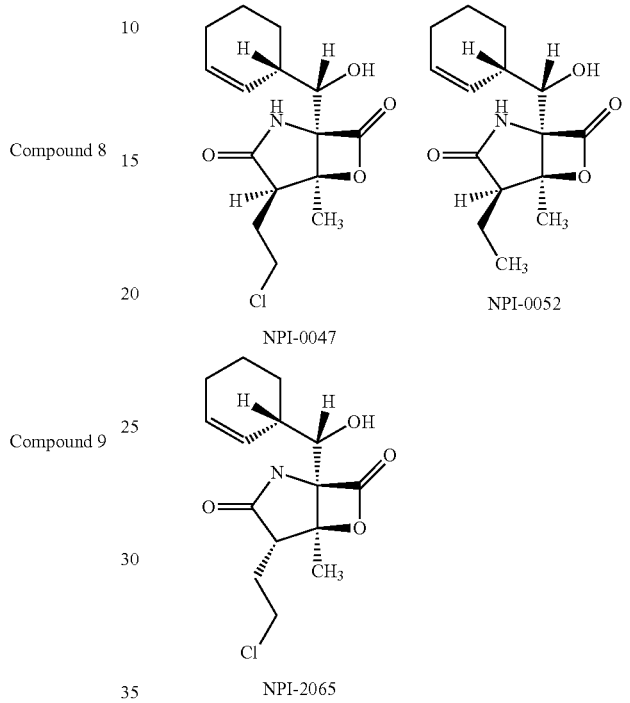

NPI-0047

NPI-0052

NPI-2065

Accordingly, some embodiments include methods for increasing the production of Salinosporamide A while concomitantly reducing production of NPI-0047 and NPI-2065. In one such embodiment, the addition of Cobalt salt in the cultivation of Salinispora tropica NPS021184 has been found to reduce the production of the two Salinosporamide A analogs, NPI-0047 and NPI-2065, and increase the production of the desired compound Salinosporamide A. As previously discussed, decrease in production of the two Salinosporamide A analogs leads to decreased loss of Salinosporamide A during the separation process. This decreased loss combined with the increased production of Salinosporamide A results in a higher total yield of the desired compound Salinosporamide A When the microorganism is cultivated in medium containing Cobalt salt as opposed to medium lacking Cobalt salt.

For the growth of Salinispora tropica NPS021184, seed cultures are prepared by inoculating frozen stocks of Salinispora tropica NPS021184 into seed medium. Any suitable carbon and nitrogen sources in the seed medium may be used. In one embodiment, the seed medium contains glucose at a concentration around 8 and Hy Soy and yeast extract each at a concentration around 6 g/L. Any of the salt formulations described above may be used in the seed formulation. In one embodiment, the salt formulation contains NaCl, $MgSO_4$, KBr, KCl, $CaCO_3$, $CaCl_2$, $SrCl_2$, $H_3BO_3$, and NaF salts as described above. In one embodiment, the salt formulation additionally includes $CoCl_2$.

After an initial incubation in the seed medium, the culture can be inoculated into a second seed medium with the same composition as the original seed medium.

After the second incubation in the seed medium, the culture can be inoculated into a production medium. If production is to be in a fermentor culture, a third seed culture may be inoculated before inoculation into the production media in the fermentor.

Any suitable carbon and nitrogen sources may be used for the production medium. In one embodiment, the production medium contains starch at a concentration around 10 g/L and concentrations of Hy Soy at about 4 g/L and yeast extract at about 4 g/L. In one embodiment, the production medium additionally includes one or more salts (separate from the supplemental salt formulations described herein). In one embodiment, these salts include $CaCO_3$, $Fe_2(SO_4)_3$, and KBr. In one embodiment the $CaCO_3$ concentration is between 2 mg/L and 50 g/L. In another embodiment the $CaCO_3$ concentration is between 100 mg/L and 10 g/L. In the preferred embodiment the $CaCO_3$ concentration is about 1 g/L. In one embodiment the $Fe_2(SO_4)_3$ concentration is between 0.5 mg/L and 10 g/L. In another embodiment the $Fe_2(SO_4)_3$ concentration is between 5 mg/L and 1 g/L. In the preferred embodiment the $Fe_2(SO_4)_3$ concentration is about 40 mg/L. In one embodiment the KBr concentration is between 0.5 mg/L and 10 g/L. In another embodiment the KBr concentration is between 5 mg/L and 1 g/L. In the preferred embodiment the KBr concentration is about 40 mg/L.

In addition, any of the salt supplement formulations described above may be added to the production medium. In one embodiment, the salt formulation contains NaCl, KCl, $CaCl_2$, $SrCl_2$, $H_3BO_3$, and NaF salts as described above. In one embodiment, the salt formulation additionally includes $CoCl_2$. In one embodiment, instead of NaCl, the salt formulation contains $Na_2SO_4$.

After inoculation into the production medium the production cultures may be further incubated and harvested at an appropriate time point. In some embodiments, harvesting occurs at various time points to determine optimal productivity.

Salinosporamide A is a potent proteasome inhibitor, but has only been produced at relatively low yields.

Unexpectedly, the present inventors have found that the presence of particular resins during the fermentation substantially increases the yield of Salinosporamide A.

The present invention is therefore directed to methods of culturing Salinispora tropica and other proteasome inhibitor producing organisms in the presence of these resins.

The descriptions in the examples provided herein describe work done on the shake flask scale. However, the invention itself should not be understood to be so limited. The invention is adaptable to any fermentation scale and should be so understood and includes commercial, pilot, laboratory and other scales as well.

Final isolation and purification of the desired compounds can be accomplished by various methods. For example, the resin can be separated from the culture medium and extracted with solvents such as ethyl acetate or other solvent capable of dissolving desired compounds. Alternatively, the resin with the culture medium can be extracted with solvents, or the culture medium can be extracted with solvents without the resin present, or the resin and medium can be extracted separately or sequentially. In some instances, a first product or set of products may be isolated from the resin while a second product or set of products may be isolated from the medium. Product set one and two may be completely different or they may both contain at least some of the same products.

Further processing of the products collected from the culture medium and/or resin can be performed to increase purity, separate one product from another, or chemically modify the one or more of the compound. Any appropriate processing technique can be used including but not limited to chromatography, crystallization, adsorption, absorption, evaporation, precipitation, distillation, extraction, and electrophoresis.

The fermentation medium described herein is exemplary. Any medium that produces growth of the organism and allows the practice of the invention can be used. Likewise, the fermentation conditions described are exemplary and can be modified without straying from the practice of the invention.

One embodiment of a fermentation medium which can be used to grow the organism includes a carbon source and a nitrogen source. Exemplary carbon sources include starch, maltodextrin, glucose, sucrose, fructose, glycerol, monosaccharides, disaccharides, oligosaccharides, polysaccharides, lactic acid, lactose, maltose and materials that contain any of these or other carbon containing compounds that are digestible by the organism alone or in combination. Exemplary nitrogen sources include, but are not limited to, proteins, amino acids, monosodium glutamate, ammonia, ammonium hydroxide, urea, corn steep liquor, corn steep solids, yeast-derived materials, and soy-derived products. Some nitrogen sources may also serve as a carbon source and some carbon sources may also serve as a nitrogen source.

An embodiment of the medium includes a carbon source, a nitrogen source, and inorganic salts. Some or all of the salts can be included in the water that is used for the fermentation or the carbon or nitrogen source. Examples of salt that is a part of the water would be the salts that become a part of the medium through the use of corn steep liquor or tap water or other non-distilled or non fully deionized water. In another embodiment, salts are added in addition to those supplied by the water, carbon or nitrogen source. These added salts may include some, all, or none of those species supplied by the other sources. In another embodiment, the salt combinations are those that are disclosed in U.S. Provisional Application No. 60/846,774, filed Sep. 22, 2006, the entire disclosure of which is incorporated by reference herein. Another embodiment utilizes the material, INSTANT OCEAN® (Aquarium Systems, Wickliffe, Ohio) as the salt source or one of the salt sources. Other embodiments utilize the salt mixtures of Tables D-1 and D-2 as the salt source or one of the salt sources.

TABLE D-1

| Salt component | per liter of DI $H_2O$ |
|---|---|
| NaCl | 24.04 g |
| KCl | 686.8 mg |
| $CaCl_2 \cdot 2H_2O$ | 429.3 mg |
| $SrCl_2$ | 15.5 mg |
| $H_3BO_3$ | 21.5 mg |
| NaF | 2.6 mg |
| $CoCl_2 \cdot 6H_2O$ | 52 µg |

TABLE D-2

| Salt component | per liter of DI $H_2O$ |
|---|---|
| NaCl | 24.04 g |
| $MgSO_4 \cdot 7H_2O$ | 4.29 g |
| KBr | 85.9 mg |
| KCl | 686.8 mg |

TABLE D-2-continued

| Salt component | per liter of DI H$_2$O |
|---|---|
| CaCO$_3$ | 429.3 mg |
| CaCl$_2$·2H$_2$O | 429.3 mg |
| SrCl$_2$ | 15.5 mg |
| H$_3$BO$_3$ | 21.5 mg |
| NaF | 2.6 mg |
| NiSO$_4$ | 57.7 µg |
| CoCl$_2$·6H$_2$O | 207.9 µg |

Resins

Solid resins may be added to the fermentation. Adding an appropriate resin or combination of resins to the fermentation may increase yield of particular compounds produced by the microorganism. In one embodiment, a solid resin is added to the fermentation prior to inoculating the fermenter with the desired microorganism. In another, the resin is added after inoculating the fermenter with the desired microorganism. In another embodiment, the resin is added to an earlier stage of the fermentation. In other embodiments, resin is present in a fermenter that is operated in a fed-batch or semicontinuous manner. In another embodiment, the resin is added prior to the onset of the stationary phase of the growth cycle of the organism. In another embodiment, the resin is mixed with medium components prior to addition to the fermentation vessel. In another embodiment the resin is added at the same time as at least one medium component. In another embodiment at least one medium component is added after the resin. In another embodiment at least one medium component is added prior to adding the resin. In another embodiment, the resin is added approximately at the point where the stationary phase of growth starts. In another embodiment, the resin is added during the stationary phase of growth.

Generally, resins adsorb chemical species to their surface. The degree of adsorption is governed by a number of factors including, for example, the concentration of the compound, the polarity of the compound, the functional groups present on the compound, the composition of the resin, the chemical environment, temperature, the presence or absence of other compounds that will compete with the targeted compound for adsorption to the resin, and the pore structure of the resin such as pore diameter and pore volume. When used in conjunction with living cells, the resin may adsorb one or more nutrients, thus depriving the cell of a material needed for growth or production of metabolites. The resin may also immobilize extracellular enzymes, suppress or inactivate enzymes and even immobilize the cells.

Exemplary resins are described in Table 2 according to their composition, pore size and porosity. These and other resins have been used in fermentations. For example, Lam, et al. showed an increase in titer of dynemicins from *Micromonospora chersina* with the addition of 1% of Diaion I-iP-20, but completely stopped production of this compound with 4% of this resin. K. S. Lam, et al., *Effect of Neutral Resins on the Production of Dynemicins by Micromonospora chersina*, Journal of Industrial Microbiology (1995) 15, 453-456.

TABLE 2

Resins and physical characteristics

| Resin | Structure | Surface area (m$^2$/g) | Pore radius (Å) | Porosity (mL/g) | Particle size (mm) | Density (g/mL) |
|---|---|---|---|---|---|---|
| XAD-2 | SDVB* | 330 | 45 | 0.65 | 0.25-0.84 | 1.08 |
| XAD-4 | SDVB* | 725 | 20 | 0.98 | 0.25-0.84 | 1.02 |
| XAD-7 | Acrylic | 450 | 45 | 1.14 | 0.25-0.84 | 1.24 |
| XAD-16 | SDVB* | 800 | 50 | 1.82 | 0.25-0.84 | 1.08 |
| IRA-67 | Acrylic-DVB** | | | | 0.3-1.2 | |
| IRC-50 | Acrylic-DVB** | | | | 0.3-1.2 | |
| IRP-64 | Methacrylic-DVB** | | | | 0.04-0.15 | |
| HP-20 | Aromatic | 511 | >200 | 1.18 | >0.25 | 1.01 |
| HP-2MG | Methacrylic | 473 | 200 | 1.15 | >0.25 | 1.09 |
| SP-207 | Modified Aromatic | 627 | 110 | 0.79 | >0.30 | 1.18 |
| SP-850 | Aromatic | 995 | 38 | 1.2 | 1 | >0.25 |

*SDVB = Styrene-divinylbenzene;
**DVB = Divinylbenzene

These resins are made by Rohm & Haas except the "HP" and "SP" resins, which are made by Mitsubishi Chemical Corp.

For the present class of organisms and class of products, it has surprisingly been found that certain resins present during the fermentation result in a substantial increase in the production of useful products. As is demonstrated in the following examples, some aspects of the present invention relate to the type of resin that is used, the time of when the resin is presented to the fermentation, and the amount of resin that is used.

The following non-limiting examples are meant to describe the preferred embodiments of the methods. Variations in the details of the particular methods employed and in the precise chemical compositions obtained will undoubtedly be appreciated by those of skill in the art. Throughout these examples, starch, peptone, and yeast extract were used in various fermentation. The particular products used were starch, USB catalog no. 21695; peptone, USB catalog no. 20048; and yeast extract, USB catalog no. 23547. However, it is envisioned that other carbon and nitrogen sources can be used as well.

EXAMPLE 1

Examination of the Effect of Cobalt in Production Media on the Production of Salinosporamide NPI-0047 and NPI-2065

Seed cultures were prepared by inoculating frozen stock of *Salinispora tropica* NPS021184 into seed medium.

The seed medium consisted of glucose, Hy Soy, and yeast extract at concentrations of 8 g/L, 6 g/L, and 6 g/L, respectively. The seed medium was then supplemented with INSTANT OCEAN® commercial salt formulation at a concentration of 30 g/L. No CoCl$_2$ was added to the seed medium.

The first seed cultures (either 10 mL medium in a 50-mL tube or 100 mL medium in a 500-mL Erlenmeyer flask) were incubated for 3 to 4 days before inoculating into the second seed media with the same composition as the first seed cultures. The second seed cultures (100 mL medium in a 500-mL Erlenmeyer flask) were incubated for two days before inoculating into the production medium (100 mL medium in a 500-mL Erlenmeyer flask).

Per liter of DI $H_2O$, the production medium consisted of: 10 g Starch, 4 g Hy So, 4 g Yeast Extract, 1 g $CaCO_3$, 40 mg $Fe_2(SO_4)_3$, and 100 mg KBr. The production medium was then supplemented with a chemically defined salt formulation, with and without various concentrations of $CoCl_2$. The chemically defined salt formulation included:

| Salt component | per liter of DI $H_2O$ |
| --- | --- |
| NaCl | 24 g |
| KCl | 0.69 g |
| $CaCl_2 \cdot 2H_2O$ | 0.43 g |
| $SrCl_2$ | 15.5 mg |
| $H_3BO_3$ | 21.5 mg |
| NaF | 2.6 mg |

Between 24 and 48 hours of inoculation into the production cultures, sterile XAD-7 resin slurry was added to the production cultures in a final concentration of 20 g/L. The production cultures were then further incubated and harvested at various time points to determine productivity 3.5 mL of the fermentation culture was mixed with equal volume of EtOAc in an extraction tube to extract the various metabolites from the production culture. The mixture was shaken on a shaker for one hr. An aliquot of the extract (1 mL) was removed and dried under a stream of nitrogen. The dried extract was stored at −20° C. freezer before HPLC analysis. The dried extract was resuspended in 320 μL DMSO and injected into HPLC using the 00TF14 method for analysis.

The production of Salinosporamide A, NPI-0047 and NPI-2065 was monitored by Agilent HP1100 HPLC using an ACE C-18 reversed-phase column (4.6×150 mm), and solvent system consisting of water (0.01% TEA) as solvent A and acetonitrile (0.01% TEA) as solvent B. The elution was started at 100% solvent A for 1 min, 100% solvent A to 35% solvent A gradient in 7 min, held at 35% solvent A for 11 min, 35% solvent A to 100% solvent B in 8 min and held at 100% solvent B for 9 min at a flow rate of 1.5 mL/min with the detector wavelength set at 210 nm and column temperature 35° C.

Effect of Cobalt Concentration on the Production of Salinosporamide A, NPI-0047, and NPI-2065 in a Shake Flask Culture $CoCl_2.6H_2O$ was added to the production medium in concentrations ranging from 2.6 μg/L to 10.4 mg/L. No $CoCl_2.6H_2O$ was added to the production medium in control samples. The production of Salinosporamide A, NPI-0047, and NPI-2065 was measured to determine the effect of the presence of cobalt as well as the effect of varying cobalt concentrations in the production media.

Results:

TABLE 1

The Effect of a Wide Range of Cobalt Concentrations in the Production Media on the Production of Salinosporamide A, NPI-0047, and NPI 2065

| | Maximum Titer (mg/L) | | | % Increase (+) or % decrease (−) | | |
| --- | --- | --- | --- | --- | --- | --- |
| $CoCl_2 \cdot 6H_2O$ Concentration | Salinosporamide A | NPI-0047 | NPI-2065 | Salinosporamide A | NPI-0047 | NPI-2065 |
| No addition | 248.0 | 10.6 | 7.7 | — | — | — |
| 104 μg/L | 251.7 | 3.6 | 6.1 | 1.5 | −65.9 | −21.0 |

TABLE 1-continued

The Effect of a Wide Range of Cobalt Concentrations in the Production Media on the Production of Salinosporamide A, NPI-0047, and NPI 2065

| | Maximum Titer (mg/L) | | | % Increase (+) or % decrease (−) | | |
| --- | --- | --- | --- | --- | --- | --- |
| $CoCl_2 \cdot 6H_2O$ Concentration | Salinosporamide A | NPI-0047 | NPI-2065 | Salinosporamide A | NPI-0047 | NPI-2065 |
| 1.04 mg/L | 253.4 | 3.5 | 6.8 | 2.2 | −67.4 | −12.2 |
| 10.4 mg/L | 244.6 | 3.1 | 5.3 | −1.4 | −71.3 | −30.8 |

The production yield of Salinosporamide A only changed negligibly with increasing concentrations of $CoCl_2.6H_2O$, up to 10.4 mg/L, in the production medium. In contrast, the production of NPI-0047 decreased dramatically by 66% when 104 μg/L $CoCl_2.6H_2O$ was added to the production medium. An increase in the concentration of $CoCl_2.6H_2O$ by 100-fold to 10.4 mg/L did not yield any further significant decrease in NPI-0047 production. The production of NPI-2065 was inhibited by 30.8% in the presence of $CoCl_2.6H_2O$ at a concentration of 10.4 mg/L in the production medium as compared to production media lacking $CoCl_2.6H_2O$. The presence of $CoCl_2.6H_2O$ in the production medium also inhibited the production of orange pigment in the fermentation.

Determination of the Optimal Cobalt Concentration in the Production Medium to Inhibit the Production of NPI-0047

The conditions described above were left unchanged except that a $CoCl_26H_2O$ concentrations ranging from 2.6 to 416 μg/L was added to the production media to determine the optimal cobalt concentration in production media to inhibit the production of NPI-0047. No $CoCl_26H_2O$ was added to control samples.

The production of Salinosporamide A, NPI-0047, and NPI-2065 was measured to determine the effect of the presence of cobalt as well as the effect of varying cobalt concentrations in the production media. Of particular interest was the effect of cobalt concentration on the production of NP1-0047.

Results:

TABLE 2

The Effect of Cobalt in the Production Media on the Production of Salinosporamide A, NPI-0047, and NPI-2065

| | Max Titers (mg/L) | | | % Increase (+) or % decrease (−) | | |
| --- | --- | --- | --- | --- | --- | --- |
| $CoCl_2 \cdot 6H_2O$ Concentration | Salinosporamide A | NPI-0047 | NPI-2065 | SALINOSPORAMIDE A | NPI-0047 | NPI-2065 |
| Control (No addition) | 272.3 | 10.2 | 6.6 | — | — | — |
| 2.6 μg/L | 275.3 | 8.3 | 6.1 | +1.1 | −18.6 | −7.6 |
| 5.2 μg/L | 247.9 | 6.0 | 6.5 | −8.9 | −41.2 | −1.5 |
| 6.5 μg/L | 275.7 | 6.3 | 6.2 | +1.2 | −38.2 | −6.1 |
| 13 μg/L | 271.3 | 4.9 | 6.5 | −0.3 | −52.0 | −1.5 |
| 26 μg/L | 261.4 | 3.7 | 6.8 | −4.0 | −63.7 | +3.0 |
| 52 μg/L | 259.9 | 3.1 | 6.3 | −4.5 | −69.6 | −4.6 |
| 104 μg/L | 264.2 | 3.5 | 6.5 | −3.0 | −65.7 | −1.5 |
| 208 μg/L | 272.8 | 3.1 | 6.2 | +0.2 | −69.6 | −6.1 |
| 416 μg/L | 249.1 | 2.7 | 5.6 | −8.5 | −73.5 | −15.2 |

An increasing concentration of cobalt in the production medium correlated with a decreasing production of NPI-0047. The inhibition effect of cobalt on the production of NPI-0047 leveled off at 52 μg/L cobalt concentration. At 52

μg/L cobalt concentration, the production of NPI-0047 was reduced by 69.6%. The production of NPI-2065 was also reduced in cobalt-supplemented conditions with the maximum inhibition effect (15% inhibition) observed at 416 μg/L, the highest concentration cobalt tested. The production of Salinosporamide A was not affected by the presence of cobalt.

EXAMPLE 2

The Effect of Cobalt in Seed Media on the Production of Salinosporamide A, NPI-0047and NPI-2065

Seed cultures were prepared by inoculating frozen stock of *Salinispora tropica* NPS021184 into seed medium.

The seed medium consisted of glucose, Hy Soy, and yeast extract at concentrations of 8 g/L, 6 g/L, and 6 g/L, respectively. The seed medium was then supplemented with a chemically defined salt formulation. The chemically defined salt formulation included:

| Salt component | per liter of DI H$_2$O |
|---|---|
| NaCl | 24 g |
| MgSO$_4$•7H$_2$O | 4.29 g |
| KBr | 85.9 mg |
| KCl | 0.69 g |
| CaCO$_3$ | 0.43 g |
| CaCl$_2$•2H$_2$O | 0.43 g |
| SrCl$_2$ | 15.5 mg |
| H$_3$BO$_3$ | 21.5 mg |
| NaF | 2.6 mg |

The seed medium was also supplemented with CoCl$_2$6H$_2$O at concentrations ranging from 2.6 μg/L to 416 μg/L. No CoCl$_2$6H$_2$O was added to control samples.

The first seed cultures (either 10 mL medium in a 50-mL tube or 100 ml medium in a 500-ml Erlenmeyer flask) were incubated for 3 to 4 days before inoculating into the second seed media with the same composition as the first seed cultures. The second seed cultures (100 mL medium in a 500-mL Erlenmeyer flask) were incubated for two days before inoculating into the production medium (100 mL medium in a 500-mL Erlenmeyer flask).

Per liter of DI H$_2$O, the production medium consisted of: 10 g Starch, 4 g Hy Soy, 4 g Yeast Extract, 1 g CaCO$_3$, 40 mg Fe$_2$(SO$_4$)$_3$, and 100 mg KBr. The production medium was then supplemented with a chemically defined salt formulation. The chemically defined salt formulation consisted of:

| Salt component | per liter of DI H$_2$O |
|---|---|
| NaCl | 24 g |
| KCl | 0.69 g |
| CaCl$_2$•2H$_2$O | 0.43 g |
| SrCl$_2$ | 15.5 mg |
| H$_3$BO$_3$ | 21.5 mg |
| NaF | 2.6 mg |

Between 24 and 48 hours of inoculation into the production cultures, sterile XAD-7 resin slurry was added to the production cultures in a final concentration of 20 g/L. The production cultures were then further incubated and harvested at various time points to determine productivity.

3.5 mL of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. freezer before HPLC analysis. The dried extract was resuspended in 320 μL DMSO and injected into HPLC using the 00TF1.4 method for analysis.

The production of Salinosporamide A, NPI-0047 and NPI-2065 was monitored by Agilent HP1100 HPLC using an ACE C-18 reversed-phase column (4.6×150 mm), and solvent system consisting of water (0.01% TFA) as solvent A and acetonitrile (0.01% TFA) as solvent. B. The elution was started at 100% solvent A for 1 min, 100% solvent A to 35% solvent A gradient in 7 min, held at 35% solvent A for 11 min, 35% solvent A to 100% solvent B in 8 min and held at 100% solvent B for 9 min at a flow rate of 1.5 mL/ruin with the detector wavelength set at 210 nm and column temperature 35° C.

Determination of the Cobalt Concentration in the Seed Medium Required to Optimize Production Salinosporamide A and Inhibition of NPI-0047 and NPI-2065

The seed medium was supplemented with CoCl$_2$.6H$_2$O at concentrations ranging from 2.6 μg/L to 416 μg/L. No CoCl$_2$6H$_2$O was added in control samples. CoCl$_2$.6H$_2$O was added to production cultures at a concentration of 52 μg/L.

The production of Salinosporamide A, NPI-0047, and NPI-2065 was measured to determine the effect of the presence of cobalt as well as the effect of varying cobalt concentrations in the seed media. The optimal cobalt concentration in the seed Medium was determined by analyzing the production of Salinosporamide A, as well as the percent NPI-0047 and NPI-2065 produced relative to the Salinosporamide A produced.

Results

TABLE 3

Determination of the optimal cobalt concentration in the seed medium

| CoCl$_2$•6H$_2$O Concentration (Seed) | Max Avg Titer (mg/L) | | | relative to Sal A (%) | | % increase/decrease | | | relative % change | |
|---|---|---|---|---|---|---|---|---|---|---|
| | Sal A | NPI-0047 | NPI-2065 | NPI-0047 | NPI-2065 | Sal A | NPI-0047 | NPI-2065 | NPI-0047 | NPI-2065 |
| 0 μg/L | 291.8 | 3.3 | 6.5 | 1.1 | 2.2 | 0.0 | 0.0 | 0.0 | 0.0 | 0.0 |
| 2.6 μg/L | 296.8 | 3.5 | 6.6 | 1.2 | 2.2 | 1.7 | 5.9 | 1.7 | 4.2 | 0.0 |
| 5.2 μg/L | 306.0 | 3.4 | 6.8 | 1.1 | 2.2 | 4.7 | 2.0 | 4.2 | −2.7 | −0.5 |
| 13 μg/L | 299.4 | 2.8 | 6.9 | 0.9 | 2.3 | 2.5 | −17.2 | 5.9 | −20.2 | 3.5 |
| 26 μg/L | 366.2 | 3.2 | 8.4 | 0.9 | 2.3 | 20.3 | −2.3 | 23.1 | −28.4 | 3.5 |
| 52 μg/L | 326.6 | 2.7 | 7.9 | 0.8 | 2.4 | 10.7 | −21.6 | 17.7 | −36.1 | 7.9 |
| 104 μg/L | 347.0 | 3.0 | 7.7 | 0.9 | 2.2 | 15.9 | −9.2 | 15.5 | −29.9 | −0.5 |

TABLE 3-continued

Determination of the optimal cobalt concentration in the seed medium

| CoCl$_2$·6H$_2$O Concentration (Seed) | Max Avg Titer (mg/L) | | | | relative to Sal A (%) | | | % increase/decrease | | | relative % change | |
|---|---|---|---|---|---|---|---|---|---|---|---|---|
| | Sal A | NPI-0047 | NPI-2065 | | NPI-0047 | NPI-2065 | | Sal A | NPI-0047 | NPI-2065 | NPI-0047 | NPI-2065 |
| 208 µg/L | 368.5 | 2.9 | 8.1 | | 0.8 | 2.2 | | 20.8 | −11.9 | 19.7 | −41.3 | −1.4 |
| 416 µg/L | 321.2 | 3.0 | 6.9 | | 0.9 | 2.2 | | 9.2 | −10.4 | 6.2 | −21.5 | −3 |

Note:
"Sal A" refers to Salinosporamide A

The optimal concentration of CoCl$_2$.6H$_2$O in the seed medium was determined to be 208 µg/L This was based on the 20.8% improvement in Salinosporamide A production, the 41.3% relative decrease in NPI-0047 production, and the 1.4% relative decrease in NPI-2065 production.

Determination of the Effect of Cobalt Concentration in the Seed Medium on the Production of Salinosporamide A, NP1-0047, and NPI-2065

The seed medium was supplemented with CoCl$_2$.6H$_2$O at a concentration of 208 µg/L. No CoCl$_2$.6H$_2$O was added to the seed medium in control samples. CoCl$_2$.6H$_2$O was added to production medium at a concentration of 52 µg/L. No CoCl$_2$.6H$_2$O was added to the production medium in control samples. The production of Salinosporamide A, NPI-0047, and NPI-2065 was measured to determine the effect of the presence of cobalt in the seed medium and production medium, Results:

TABLE 4

Effect of cobalt concentration in the seed medium on the production of Salinosporamide A, NPI-0047, and NPI-2065

| CoCl$_2$·6H2O in seed medium | CoCl$_2$·6H2O in production medium | Average Max Titer (mg/L) | | | % Increase (+) or % decrease (−) | | |
|---|---|---|---|---|---|---|---|
| | | SALINOSPORAMIDE A | NPI-0047 | NPI-2065 | SALINOSPORAMIDE A | NPI-0047 | NPI-2065 |
| 0 | 0 | 227.6 | 12.7 | 7.8 | — | — | — |
| 0 | 52 µg/L | 250.6 | 3.6 | 4.9 | +10.1 | −71.7 | −37.2 |
| 208 µg/L | 52 µg/L | 304.7 | 2.8 | 4.3 | +33.9 | −78.0 | −44.9 |

(Average of Three Experiments)

Addition of cobalt to both the seed and production media increased the production of Salinosporamide A by 33.9% as compared to seed and production media without cobalt. Additionally, the production of NPI-0047 was reduced by 78.0% and production of NPI-2065 was reduced by 44.9%.

As compared to conditions where cobalt was added only to the production medium, the presence of cobalt in the seed medium and production medium increased the production of Salinosporamide A by 21.6%, reduced the production of NPI-0047 by 22.2% and reduced the production of NPI-2065 by 12.2%. This result demonstrates the benefit of adding cobalt to both seed and production media.

EXAMPLE 3

Effect of Cobalt on the Production of Salinosporamide A, NPI-0047 and NPI-2065 in Fermentor Culture Seed cultures were prepared by inoculating frozen stock of Salinispora tropica NPS021184 into seed medium. For 10 seed medium in a 50-mL culture tube, one frozen stock (~1.5 mL) was used for inoculation. For 100 mL seed medium in a 500-mL Erlenmeyer flask, two frozen stocks (~3 mL total) were used for inoculation, The seed medium consisted of glucose, Hy Soy, and yeast extract at concentrations of 8 g/L, 6 g/L, and 6 g/L, respectively. The seed medium was then further supplemented with either INSTANT OCEAN® (Aquarium Systems, Inc., Wickliffe, Ohio) commercial salt formulation or a chemically defined salt formulation. This chemically defined formulation consisted of:

| Salt component | per liter of DI H$_2$O |
|---|---|
| NaCl | 24 g |
| MgSO$_4$·7H$_2$O | 4.29 g |
| KBr | 85.9 mg |
| KCl | 0.69 g |

-continued

| Salt component | per liter of DI H$_2$O |
|---|---|
| CaCO$_3$ | 0.43 g |
| CaCl$_2$·2H$_2$O | 0.43 g |
| SrCl$_2$ | 15.5 mg |
| H$_3$BO$_3$ | 21.5 mg |
| NaF | 2.6 mg |

The seed medium was also supplemented with CoCl$_2$.6H$_2$O at a concentration of 208 µg/L. No CoCl$_2$.6H$_2$O was added to the seed medium in control samples.

The first seed cultures (either 10 mL medium in a 50-mL tube or 100 mL medium in a 500-mL Erlenmeyer flask) were incubated at 250 rpm and 28° C. for 3 to 4 days before inoculating (5% inoculum) into second seed medium with the same salt composition as used for the first seed cultures. After incubating at 250 rpm and 28° C. for 2 days, the second seed cultures (5% inoculum) were inoculated into an additional third seed culture (400 mL medium in 2.81.

Fernbach flask) with the same medium, salt composition and incubation time as the second seed cultures, before inoculating into production media in the fermentor (26 L medium in a 42 L B. Braun Biostat-C fermentor), Per liter of DI $H_2O$, the production medium consisted of:

| | |
|---|---|
| 10 g | Starch |
| 4 g | Hy Soy |
| 4 g | Yeast Extract |
| 1 g | $CaCO_3$ |
| 40 mg | $Fe_2(SO_4)_3$ |
| 100 mg | KBr |

The production medium was then supplemented with either INSTANT OCEAN® commercial salt formulation or a chemically defined salt formulation based on the salt supplement used in the seed stages. The chemically defined salt formulation consisted of

| Salt component | per liter of DI $H_2O$ |
|---|---|
| NaCl | 24 g |
| KCl | 0.69 g mg |
| $CaCl_2 \cdot 2H_2O$ | 0.43 g mg |
| $SrCl_2$ | 15.5 mg |
| $H_3BO_3$ | 21.5 mg |
| NaF | 2.6 mg |

The production medium for fermentation was also supplemented with $CoCl_2.6H_2O$ at a concentration of 52 µg/L. No $CoCl_2.6H_2O$ was added to the production medium in control samples.

Between 24 and 48 hours of inoculation into the production cultures, sterile XAD-7 resin slurry was added to the production cultures in a final concentration of 20 g/L. The production cultures were then further incubated and harvested at various time points to determine productivity.

3.5 mL of the fermentation culture was mixed with equal volume of EtOAc in an extraction tube to extract the various metabolites from the production culture. The mixture was shaken for 1 hr. An aliquot of the extract (1 mL) was removed and dried under a stream of nitrogen. The dried extract was stored at −20° C. freezer before HPLC analysis. The dried extract was resuspended in 320 µL DMSO and injected into HPLC using the 00TF14 method for analysis.

The production of Salinosporamide A, NPI-0047 and NPI-2065 was monitored by Agilent HP1100 HPLC using an ACE C-18 reversed-phase column (4.6×150 mm), and solvent system consisting of water (0.01% TFA) as solvent A and acetonitrile (0.01% TFA) as solvent B. The elution was started at 100% solvent A for 1 min, 100% solvent A to 35% solvent A gradient in 7 min, held at 35% solvent A for 11 min, 35% solvent A to 100% solvent B in 8 min and held at 100% solvent B for 9 min at a flow rate of 1.5 mL/min with the detector wavelength set at 210 nm and column temperature 35° C.

Effect of Cobalt on the Production of Salinosporamide A, NPI-0047, and NPI-2065 Incubated in Seen Medium Supplemented with INSTANT OCEAN® Commercial Salt Formulation and Fermented in Production Medium also Supplemented with INSTANT OCEAN® Commercial Salt Formulation.

The seed medium was supplemented with INSTANT OCEAN® salt formulation at a concentration of 30 g/L. No $CoCl_2.6H_2O$ was added to the seed medium. The production medium was supplemented with INSTANT OCEAN® salt formulation at a concentration of 30 g/L. No $CoCl_2.6H_2O$ was added to the production medium.

The production of Salinosporamide A, NPI-0047, and NPI-2065 was measured. The results are presented below in Table 5.

TABLE 5

Production of Salinosporamide A, NPI-0047, and NPI-2065 incubated in seed medium and fermented in production medium each supplemented with INSTANT OCEAN® commercial salt formulation in the absence of cobalt

| Batch # | SALINOSPORAMIDE A (mg/L) | NPI-0047 (mg/L) | NPI-2065 (mg/L) | % NPI-0047 as SALINOSPORAMIDE A | % NPI-2065 as SALINOSPORAMIDE A |
|---|---|---|---|---|---|
| C27 | 260 | 9.8 | 9.6 | 3.8 | 3.7 |
| C29 | 250 | 13.8 | 11.0 | 5.5 | 4.4 |
| C30 | 260 | 8.3 | 9.1 | 3.2 | 3.5 |
| Average | 257 | 30.6 | 9.9 | 4.1 | 3.9 |

To test the effect of cobalt, seed medium was supplemented with INSTANT OCEAN® salt formulation at a concentration of 30 g/L. $CoCl_2.6H_2O$ was added to the seed medium at a concentration of 208 µg/L. The production medium was supplemented with INSTANT OCEAN® salt formulation at a concentration of 30 g/L. $CoCl_2.6H_2O$ was added to the production medium at a concentration of 52 µg/L. The production of Salinosporamide A, NPI-0047, and NPI-2065 was measured to determine the effect of cobalt added to the seed medium and production medium. The results are presented below in Table 6.

TABLE 6

Production of Salinosporamide A, NPI-0047, and NPI-2065 incubated in seed medium and fermented in production medium each supplemented with INSTANT OCEAN ® commercial salt formulation in the presence of cobalt

| Batch # | SALINOSPORAMIDE A (mg/L) | NPI-0047 (mg/L) | NPI-2065 (mg/L) | RATIO OF SALINOSPORAMIDE A TO NPI-0047, % | RATIO OF SALINOSPORAMIDE A TO NPI-2065, % |
|---|---|---|---|---|---|
| C49 | 340 | 6.5 | 9.2 | 1.9 | 2.7 |
| C50 | 295 | 5.0 | 7.7 | 1.7 | 2.6 |
| C53 | 265 | 5.0 | 5.8 | 1.9 | 2.2 |
| Average | 300 | 5.5 | 7.6 | 1.8 | 2.5 |

Results:

With the addition of cobalt in both the seed and production media using INSTANT OCEAN® salt formulation, on average the production of Salinosporamide A increased by 14.3%, the production of NPI-0047 decreased by 48.1%, and production of NPI-2065 decreased by 23.2%.

Effect of Salt Formulations on the Production of Salinosporamide A, NPI-0047, and NPI-2065.

The seed medium was supplemented with the chemically defined salt formulation. The seed medium was also supplemented with $CoCl_2.6H_2O$ at a concentration of 208 µg/L.

The production medium was supplemented with the chemically defined salt formulation. The production medium was supplemented with $CoCl_2.6H_2O$ at a concentration of 52 µg/L.

The production of Salinosporamide A, NPI-0047, and NPI-2065 was measured to compare production by cultures grown in chemically defined salt supplemented seed medium and chemically defined salt supplemented production medium with production by cultures grown in seed and production media supplemented with INSTANT OCEAN® commercial salt formulation presented in tables 5 and 6 above.

TABLE 7

Production of Salinosporamide A, NPI-0047, and NPI-2065 produced by cultures grown in chemically defined salt supplemented seed medium and chemically defined salt supplemented production medium in the presence of cobalt.

| Batch # | SALINOSPORAMIDE A (mg/L) | NPI-0047 (mg/L) | NPI-2065 (mg/L) | RATIO OF SALINOSPORAMIDE A TO NPI-0047, % | RATIO OF SALINOSPORAMIDE A TO NPI-2065, % |
|---|---|---|---|---|---|
| C39 | 280 | 3.4 | 7.0 | 1.2 | 2.5 |
| C42 | 267 | 2.4 | 6.9 | 0.9 | 2.6 |
| Average | 274 | 2.9 | 7.0 | 1.1 | 2.6 |

Results

TABLE 8

Comparison of Production of Salinosporamide A, NPI-0047, and NPI-2065 in seed and production media supplemented with or without cobalt in a 42 L fermentor

| Media | SAL A (mg/L) | NPI-0047 (mg/L) | NPI-2065 (mg/L) | RATIO OF SAL A TO NPI-0047, % | RATIO OF SAL A TO NPI-2065, % |
|---|---|---|---|---|---|
| Seed: Instant Ocean no cobalt Production: Instant Ocean no cobalt | 257 | 10.6 | 9.9 | 4.1 | 3.9 |
| Seed: Instant Ocean + 208 µg/L $CoCl_2 \cdot 6H_2O$ Production: Instant Ocean + 52 µg/L $CoCl_2 \cdot 6H_2O$ | 300 | 5.5 | 7.6 | 1.8 | 2.5 |
| Seed: Chemically Defined Salt + 208 µg/L $CoCl_2 \cdot 6H_2O$ Production: Chemically Defined Salt + 52 µg/L $CoCl_2 \cdot 6H_2O$ | 274 | 2.9 | 7.0 | 1.1 | 2.6 |

SAL A is Salinosporamide A

By replacing the INSTANT OCEAN® commercial salt formulation with a chemically defined salt formulation in the seed medium and a chemically defined salt formulation with cobalt chloride in the production medium, the production of NPI-0047 was reduced by 47.3% and the production of NPI-2065 was reduced by 7.9%. The production of Salinosporamide A decreased by 8.7%.

Example 4

The Effect of Non-Saline, "Low Chloride", Salt Formulation on the Production of Salinosporamide A, NPI-0047, and NPI-2065

Seed cultures were prepared by inoculating frozen stock of *Salinispora tropica* NPS021184 into seed medium.

The seed medium consisted of glucose, Hy Soy, and yeast extract at concentrations of 8 g/L, 6 g/L, and 6 g/L, respectively. The seed medium was then supplemented with a chemically defined salt formulation. The chemically formulation consisted of:

| Salt component | per liter of DI $H_2O$ |
| --- | --- |
| NaCl | 24 g |
| $MgSO_4 \cdot 7H_2O$ | 4.29 g |
| KBr | 85.9 mg |
| KCl | 0.69 g |
| $CaCO_3$ | 0.43 g |
| $CaCl_2 \cdot 2H_2O$ | 0.43 g |
| $SrCl_2$ | 15.5 mg |
| $H_3BO_3$ | 21.5 mg |
| NaF | 2.6 mg |

The seed medium was supplemented with $CoCl_2 \cdot 6H_2O$ at a concentration of 208 µg/L. No $CoCl_2 \cdot 6H_2O$ was added to the seed medium in control samples.

The first seed cultures (either 10 mL medium in a 50-mL tube or 100 mL medium in a 500-mL Erlenmeyer flask) were incubated for 3 to 4 days before inoculating into the second seed media with the same composition as the first seed cultures. The second seed cultures (100 mL medium in a 500-mL Erlenmeyer flask) were incubated for two days before inoculating into production medium (100 mL medium in a 500-mL Erlenmeyer flask).

Per liter of DI $H_2O$, the production medium consisted of: 1.0 g Starch, 4 g Hy Soy, 4 g Yeast Extract, 1 g $CaCO_3$, 40 mg $Fe_2(SO_4)_3$, and 100 mg KBr. The production medium was then either supplemented with INSTANT OCEAN® commercial salt formulation or supplemented with a chemically defined salt formulation. This chemically defined salt formulation consisted of:

| Salt component | per liter of DI $H_2O$ |
| --- | --- |
| KCl | 0.69 g |
| $CaCl_2 \cdot 2H_2O$ | 0.43 g |
| $SrCl_2$ | 15.5 mg |
| $H_3BO_3$ | 21.5 mg |
| NaF | 2.6 mg |

The production medium with the chemically defined salt formulation was then supplemented with either NaCl at a concentration of 24 g/L or $Na_2SO_4$ at a concentration of 15 g/L. Production medium containing the chemically defined salt formulation and NaCl was either supplemented with $CoCl_2 6H_2O$ at a concentration of 52 µg/L or not at all. Production medium containing the chemically defined salt formulation and $Na_2SO_4$ was supplemented at a concentration of 52 µg/L.

Between 24 and 48 hours after inoculation, sterile XAD-7 resin slurry was added to the production cultures in a final concentration of 20 g/L. The production cultures were then further incubated and harvested at various time points to determine productivity.

3.5 mL of the fermentation culture was mixed with equal volume of EtOAc in an extraction tube to extract the various metabolites from the production culture. The mixture was shaken for 1 hr. An aliquot of the extract (1 mL) was removed and dried under a stream of nitrogen. The dried extract was stored at −20° C. freezer before HPLC analysis. The dried extract was resuspended in 320 µL DMSO and injected into HPLC using the TFS7 method for analysis.

The production of Salinosporamide A, NPI-0047 and NPI-2065 was monitored by Agilent HP1100 HPLC using an ACE C-18 reversed-phase column (4.6×150 mm), and isocratic solvent system consisting of 67% water (0.01% TFA) and 33% acetonitrile (0.01% TEA). The flow rate was 1.5 mL/min for 15 min with the detector wavelength set at 210 nm and column temperature 35° C.

Results:

TABLE 9

Production of Salinosporamide A, NPI-0047, and NPI-2065 in production media with various salt compositions

| Media | Sal A (mg/L) | NPI-0047 (mg/L) | NPI-2065 (mg/L) |
| --- | --- | --- | --- |
| INSTANT OCEAN ® | 228 | 12.7 | 7.8 |
| Chemically Defined Salt Formulation + NaCl | 248 | 10.6 | 7.7 |
| Chemically Defined Salt Formulation + NaCl + 52 µg/L $CoCl_2 \cdot 6H_2O$ | 279* | 3.2* | 5.2* |
| Chemically Defined Salt Formulation + $Na_2SO_4$ + 52 µg/L $CoCl_2 \cdot 6H_2O$ (Medium Lo.Maz) | 217 | 7.3 | 3.4 |

*Average of two experiments

Particular ions present in the low chloride, $Na_2SO_4$ based. Medium Lo.Maz were analyzed by ICP-MS analysis and are listed in the table below:

TABLE 10

ICP-MS Analysis of Ions of Interest in Lo. Maz Medium, mM

| Medium | [Na] | [Cl] | [K] | [Mg] | [Co] | [S] |
| --- | --- | --- | --- | --- | --- | --- |
| Lo.Maz | 222 | 17 | 16 | 0.49 | $3.1 \times 10^{-4}$ | 124 |

The chemically defined salt formulation with $Na_2SO_4$ significantly reduced chloride content (17 mM) and reduced sodium content (222 mM). This low chloride, non-saline salt formulation is significantly less corrosive to fermentor than the regular saline salt formulation. As evidenced by Table 9, the production of Salinosporamide A, NPI-0047, and NPI-2065 was only minimally reduced as compared to the chemically defined salt formulation with NaCl.

EXAMPLE 5

Growth of *Salinispora tropica* NPS021184 and Production of Salinosporamide A in a Non-Saline, Low Sodium, Production Medium Containing Trace Amount of Sodium Ion (Calculated Value: 10.7 mM; ICP-MS Analysis: 16 mM)

Seed cultures were prepared by inoculating a frozen stock of *Salinispora tropica* NPS021184 into seed medium.

The seed medium consisted of the following per liter of DI water: 10 g Starch, 4 g Hy Soy, 4 g Yeast Extract, 1 g $CaCO_3$, and 40 mg $Fe_2(SO_4)_3$. The seed medium was then supplemented with the chemically defined salt formulation shown below. This supplemented medium is referred to as Lo.BNA.

| Salt component | Per liter of DI $H_2O$ |
|---|---|
| $Na_2SO_4$ | 15 g |
| $MgSO_4 \cdot 7H_2O$ | 4.29 g |
| KBr | 85.9 mg |
| KCl | 0.69 g |
| $CaCl_2 \cdot 2H_2O$ | 0.43 g |
| $SrCl_2$ | 15 5 mg |
| $H_3BO_3$ | 21.5 mg |
| NaF | 2.6 mg |
| $CoCl_2 \cdot 6H_2O$ | 208 µg |

The first seed culture (10 mL medium) in a 50-not culture tube was incubated for 72 hours before inoculating 5 mL of the first seed culture into the second seed medium with the same composition as the first seed medium. The second seed culture (100 mL medium in a 500-mL Erlenmeyer flask) was incubated for 48 hours before inoculating 5 mL of the second seed culture into the production medium (100 mL in a 500-mL Erlenmeyer flask) supplemented with trace amount of sodium ion (0.06 mM from NaF).

Per liter of DI $H_2O$, the production medium consisted of: 10 g Starch, 4 g Hy Soy, 4 g Yeast Extract, 1 g $CaCO_3$, 40 mg$Fe_2(SO_4)_3$, and 100 mg KBr. The production medium was then supplemented with the chemically defined salt formulation shown below. This supplemented media is referred to as SHY.KcMC.

| Salt component | Per liter of DI $H_2O$ |
|---|---|
| KCl | 30 g |
| $CaCl_2 \cdot 2H_2O$ | 0.43 g |
| $SrCl_2$ | 15 5 mg |
| $H_3BO_3$ | 21.5 mg |
| NaF | 2.6 mg |
| $CoCl_2 \cdot 6H_2O$ | 52 µg |

The production medium was supplemented with 0.06 mM sodium ion derived from NaF (2.6 mg/L). The major source of the sodium ion in the production culture was derived from the 5% seed inoculum (5 mL seed culture into 100 mL production medium), which contained 211 mM sodium ion from 15 g/L, sodium sulfate. Therefore, the 5% seed inoculum supplied 10.6 mM sodium ion to the production culture. The calculated amount of sodium ion present in the production medium was 10.7 mM (0.06 mM+10.6 mM). The amount of particular ions in the seed medium, production medium and production after inoculation of 5% of seed medium by ICP-MS analysis are listed in the following table.

TABLE 11

ICP-MS analysis of key ion concentration in seed medium Lo.BNA, Production medium SHY.KcMC and Medium SHY.KcMC with 5% Lo.BNA

|  | [Na] | [Cl] | [K] | [Mg] | [Co] | [S] | [Ca] | [Fe] |
|---|---|---|---|---|---|---|---|---|
| Seed medium (Lo.BNA) | 215 | 17 | 13 | 19 | $1.2 \times 10^{-3}$ | 143 | 3.8 | 0.17 |
| Production medium (SHY.KcMC) | 11 | 477 | 468 | 0.75 | $3.7 \times 10^{-4}$ | 1.7 | 4.1 | 0.12 |
| Production medium after inoculation of 5% seed medium | 16 | 453 | 411 | 1.6 | $3.9 \times 10^{-4}$ | 8.8 | 3.8 | 0.12 |

About 24 hour after inoculation, sterile XAD-7 resin slurry was added to the production cultures in a final concentration of 20 g/L. The production culture was then further incubated and harvested at various time points to determine productivity.

3.5 mL of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. freezer before HPLC analysis. The dried extract was resuspended in 320 µL DMSO and injected into HPLC using the TFS7 method for analysis.

The production of Salinosporamide A, NPI-0047 and NPI-2065 was monitored by Agilent HP1100 HPLC using an ACE C-18 reversed-phase column (4.6×150 mm), and an isocratic solvent system consisting of 67% water (0.01% TFA) and 33% acetonitrile (0.01% TEA). The flow rate was 1.5 mL/min for 15 min with the detector wavelength set at 21.0 nm and column temperature 35° C.

TABLE 12

Production of Salinosporamide A, NPI-0047 and NPI-2065 by *Salinispora tropica* NPS021184 grown in production medium containing ~10.7 mM sodium ion (calculated value) and 16 mM sodium ion determined by ICP-MS analysis.

|  | Titer (mg/L) | | |
|---|---|---|---|
| Culture Age (days) | Salinosporamide A | NPI-0047 | NPI-2065 |
| 3 | 109 | 0.7 | 0.9 |
| 4 | 187 | 1.1 | 2.5 |
| 5 | 226 | 0.3 | 3.5 |
| 6 | 239 | 0.5 | 4.0 |

While the amount of sodium ion known to be present the production medium SHY.KcMC is 0.06 mM based on the addition of 2.6 mg/L NaF, ICP-MS analysis showed that the actual sodium ion content in production medium SHY- .KcMC is 11 mM. The additional sodium present in the production medium SI-IY.KcMC is derived from the other medium components such as Hy Soy and yeast extract (see Table 20 of Example 9). By the same token, the calculated amount of sodium present in the production medium after the inoculation of seed medium containing high sodium content is 10.7 mM while the actual sodium content determined by ICP-MS analysis is 16 mM.

*Salinispora tropica* NPS21184 can be grown in production medium containing low sodium ion concentration at 16 mM, about 3% of the sodium concentration present in sea water (487 mM sodium, see Table 20 of Example 9). In this low sodium production medium, *Salinispora tropica* NPS21184 produced 239 mg/L of Salinosporamide A.

EXAMPLE 6

Growth of *Salinispora tropica* NPS021184 and Production of Salinosporamide A in Non-Saline, Low Sodium, Seed and Production Media Containing Trace Amount of Sodium Ion (Calculated Value: 0.06 mM; ICP-MS Analysis: 11 mM)

The first seed culture was prepared by inoculating two frozen stocks of *Salinispora tropica* NPS021184 into first seed medium containing INSTANT OCEAN® commercial salt formulation to obtain good cell growth. The first seed culture was centrifuged and washed with Wash Media to remove the sodium ion present in the first seed culture before inoculating into the first of two additional seed stages. The medium used for these last two seed stages contained only trace amounts of sodium ion (calculated value of sodium based on the added NaF: 0.06 mM; estimated to be around 5.7 mL based on analysis of a similar medium, A1.Ks4C, in Example 7). The third seed culture was then inoculated into the production medium SHY.KcMC containing only trace amounts of sodium ion (calculated value of sodium derived from the added NaF: 0.06 mM; ICP-MS analysis: 11 mM). This process significantly reduced the carryover of sodium ion from the seed cultures to the production culture.

The first seed medium consisted of glucose, Hy Soy, and yeast extract at concentrations of 8 g/L, 6 g/L, and 6 g/L, respectively. The seed medium was then supplemented with 30 g/L INSTANT OCEAN® commercial salt formulation The first seed culture (100 ml medium containing ~424 mM sodium ion from Instant Ocean by ICP-MS analysis, Table 20 in Example 9) in a 500-mL Erlenmeyer flask was incubated at 28° C. and 250 rpm for 72 hours. 10 mL of the first seed culture was transferred to a sterile 15-mL centrifuge tube and centrifuged at 3,000 rpm for 15 min. The packed cell volume observed was 3%, The supernatant was decanted and 10 mL of Wash Medium (10 g/L starch, 2 g/L peptone, 4 g/L yeast extract, and 30 g/L, KCl) was added to the centrifuge tube. The centrifuge tube was mixed and then centrifuged at 3000 rpm for 15 min. The supernatant was decanted and the cells were centrifuged, suspended in Wash Media, and centrifuged again as described above. After the final washing, 10 mL of the second seed medium (containing 0.06 mM sodium ion from NaF) was added to the centrifuge tube. The second seed medium consisted of 10 g/L starch (USB, catalog #21695), 2 g/L peptone (USB, catalog #20048), 4 g/L yeast extract (USB, catalog #23547) and the chemically defined salt formulation shown below. This medium was called A1.Kc4C

| Salt component | Per liter of DI H$_2$O |
| --- | --- |
| KCl | 30 g |
| MgSO$_4$•7H$_2$O | 4.29 g |
| KBr | 85.9 mg |
| CaCO$_3$ | 0.43 g |
| CaCl$_2$•2H$_2$O | 0.43 g |
| SrCl$_2$ | 15 5 mg |
| H$_3$BO$_3$ | 21.5 mg |
| NaF | 2.6 mg |
| CoCl$_2$•6H$_2$O | 208 µg |

The sodium content in the second seed medium should be around 5.7 mM based on the ICP-MS analysis of a similar medium, A1.Ks4C (Example 7, 30 g/L KCl instead of 30 g/L K$_2$SO$_4$), and the sodium content present in A1 media (5.2 mM sodium, Table 20 of Example 9). The centrifuge tube was gently vortexed to mix the cell suspension and 5 mL of the washed cells was inoculated to the second seed culture containing 100 ml medium having the same composition as the second seed medium in a 500-mL Erlenmeyer flask. The sodium concentration in the washed cell inoculum had been reduced down to a calculated value of 03.07 m.M based on 424 mM sodium from the INSTANT OCEAN® supplement and 3% packed cell volume. This value is similar to the second seed medium sodium concentration (0.06 mM from 2.6 mg/L NaF). The second seed culture was incubated for 2 days before inoculating 5 mL of the second seed culture into the third seed culture containing the same medium and supplements as the second seed culture. The third seed culture was incubated for 3 days before inoculating 5 ml of the third seed culture into the production medium (100 ml in a 500-ml Erlenmeyer flask) with the same composition of the production medium, SHY.KcMC, in Example 5.

Per liter of DI H$_2$O, the production medium consisted of 10 g Starch, 4 g Hy Soy, 4 g Yeast Extract, 1 g CaCO$_3$, 40 mg Fe$_2$(SO$_4$)$_3$, 100 mg KBr and the salt supplement shown below. This production medium was then supplemented with a chemically defined salt formulation and then is referred to as SHY.KcMC. The chemically defined salt formulation consisted of:

| Salt component | Per liter of DI H$_2$O |
| --- | --- |
| KCl | 30 g |
| CaCl$_2$•2H$_2$O | 0.43 g |
| SrCl$_2$ | 15.5 mg |
| H$_3$BO$_3$ | 21.5 mg |
| NaF | 2.6 mg |
| CoCl$_2$•6H$_2$O | 52 µg |

About 24 hour after inoculation, sterile XAD-7 resin slurry was added to the production cultures in a final concentration of 20 g/L. The production culture was then further incubated and sampled at various times to determine productivity.

3.5 mL of the fermentation culture was mixed with equal volume of EtOAc in an extraction tube to extract the various metabolites from the production culture. The mixture was shaken on a shaker for 1 hr. An aliquot of the extract (1 mL) was removed and dried under a stream of nitrogen. The dried extract was stored at −20° C. freezer before HPLC analysis. The dried extract was resuspended in 320 µL DMSO and injected into HPLC using the TFS7 method for analysis.

The production of Salinosporamide A, NPI-0047 and NPI-2065 was monitored by an Agilent HP1100 HPLC using an ACE C-18 reversed-phase column (4.6×150 mm), and an isocratic solvent system consisting of 67% water (0.01% TFA) and 33% acetonitrile (0.01% TFA). The flow rate was 1.5 mL/min for 15 mm with the detector wavelength set at 210 nm and column temperature 35° C.

TABLE 13

Production of Salinosporamide A, NPI-0047 and NPI-2065 by *Salinispora tropica* NPS021184 grown in production medium containing 0.06 mM sodium ion based on NaF added to the medium and 11 mM sodium ion based on ICP-MS analysis.

| Culture Age (days) | Titers (mg/L) | | |
|---|---|---|---|
| | Salinosporamide A | NPI-0047 | NPI-2065 |
| 3 | 45 | 0 | 0.7 |
| 4 | 100 | 0 | 1.0 |
| 5 | 170 | 0.5 | 1.8 |
| 6 | 176 | 0.6 | 2.1 |

*Salinispora tropica* NPS211.84 can be grown in production medium containing low sodium ion concentration (~11 mM), which is about 2% of the sodium content in sea water (487 mM sodium, see Table 20 of Example 9). In this low sodium production medium, *Salinispora tropica* NPS21184 produced 176 mg/L of Salinosporamide A. Since *Salinispora tropica* NPS21184 can be grown in the A1-based seed medium with sodium content estimated at 5.7 mM based on elemental analysis of similar media, this demonstrated that *Salinispora tropica* NPS21184 can be grown in medium with sodium content as low as 1% of seawater.

EXAMPLE 7

Growth of *Salinispora tropica* NPS021184 in Agar Media Containing (a) Low Sodium and (b) Low Sodium and Low Chloride The first seed culture was prepared by inoculating two frozen stocks of *Salinispora tropica* NPS021184 into first seed medium consisted of glucose, Hy Soy, and yeast extract at concentrations of 8 g/L, 6 g/L, and 6 g/L, respectively. The seed medium was then supplemented with 30 g/L INSTANT OCEAN® commercial salt formulation.

The first seed culture (100 mL medium containing 424 mM sodium ion from INSTANT OCEAN®) in a 500-mL Erlenmeyer flask was incubated at 28° C. and 250 rpm for 72 hours. 1.5 mL of the first seed culture each was transferred to two sterile 15-mL centrifuge tubes and centrifuged at 3,000 rpm for 15 min. The supernatant from each tube was decanted. 10 mL of wash Medium A was added to one tube while 10 mL of Wash Medium B was added to the other tube. Both wash media consisted of starch, peptone, and yeast extract at concentrations of 10 g/L, 2 g/L, and 4 g/L, respectively. Wash Medium A also included 30 g/L KCl while Wash Medium B included 48 g/L $K_2SO_4$. The centrifuge tubes were mixed and then centrifuged at 3000 rpm for 15 min. The supernatant was decanted and the cells were resuspended in the same Wash Media and centrifuged again as previously described. At the final washing, a pipette was used to remove most of the supernatant and to allow enough medium to yield a 2 ml cell suspension in the tube. These cell suspensions were used as the inoculum for the agar cultures. Four agar media were used, Agar Media. A, A-1, B and B-1, and all consisted of starch, peptone, yeast extract, and agar (Diko, catalog #214530) at concentrations of 10 g/L, 2 g/L, 4 g/L and 17 g/L, respectively as well as a salt supplement. Agar Medium A was supplemented with the following chemically defined salt formulation. This supplemented medium is referred to as A1.Kc4C

| Agar Medium A - Salt Supplement | |
|---|---|
| Salt component | Per liter of DI $H_2O$ |
| KCl | 30 g |
| $MgSO_4 \cdot 7H_2O$ | 4.29 g |
| KBr | 85.9 mg |
| $CaCO_3$ | 0.43 g |
| $CaCl_2 \cdot 2H_2O$ | 429.3 mg |
| $SrCl_2$ | 15.5 mg |
| $H_3BO_3$ | 21.5 mg |
| NaF | 2.6 mg |
| $CoCl_2 \cdot 6H_2O$ | 208 µg |

In order to test the significance of ion supplements other than potassium, Agar Medium A-1 was supplemented only with 30 g/L KCl. That is, to examine if simple replacement of NaCl by KCl in the agar medium can support the growth of *Salinispora tropica* NPS21184.

Agar Medium B was supplemented with the following chemically defined salt formulation. This supplemented medium is referred to as A1.Ks4C

| Agar Medium B - Salt Supplement | |
|---|---|
| Salt component | Per liter of DI $H_2O$ |
| $K_2SO_4$ | 48 g |
| $MgSO_4 \cdot 7H_2O$ | 4.29 g |
| KBr | 85.9 mg |
| $CaCO_3$ | 0.43 g |
| $CaCl_2 \cdot 2H_2O$ | 429.3 mg |
| $SrCl_2$ | 15.5 mg |
| $H_3BO_3$ | 21.5 mg |
| NaF | 2.6 mg |
| $CoCl_2 \cdot 6H_2O$ | 208 µg |

In order to test the significance of ion supplements other than potassium, Agar Medium B-1 was supplemented only with 48 g/L $K_2SO_4$. That is, to examine if simple replacement of NaCl by $K_2SO_4$ in the agar medium can support the growth of *Salinispora tropica* NPS21184. Particular ion concentrations of Agar Medium B with the complete salt supplements (Medium A1.Ks4C) were determined by ICP-MS.

TABLE 14A

ICP-MS analysis of Particular ion concentrations (mM) in Medium A1.Ks4C, a low sodium and low chloride medium

| [Na] | [Cl] | [K] | [Mg] | [Co] | [S] | [Ca] | [Fe] |
|---|---|---|---|---|---|---|---|
| 5.7 | 14 | 649 | 23 | $1.2 \times 10^{-3}$ | 421 | 4.0 | 0.011 |

The sodium and chloride concentration in A1.KsMC are very low at 5.7 mM and 14 mM, respectively, based on ICP-MS analysis. The ion concentration of A1.KcMC medium was not determined by ICP-MS. However, the sodium content in A1.KcMC should be similar to the sodium content in A1.KsMC, 5.7 mM, because the two media have the same composition except A1.KcMC has 30 g/L KCl where A1.KsMC has 48 g/L $K_2SO_4$.

Sterile inoculation loops were used to transfer cells from Wash Medium A to agar plates containing 20 mL of Agar Medium A (calculated sodium content: 0.06 mM; calculated chloride content: 415 mM) or 20 mL of Agar Medium A-1

(calculated sodium content: 0.06 mM; calculated chloride content: 403 mM). Sterile inoculation loops were used to transfer cells from Wash Medium B to agar plates containing 20 mL of Agar Medium B (calculated sodium content: 0.06 mM; calculated chloride content: 12 mM; ICP-MS analysis: sodium content: 5.7 mM; chloride content: 14 mM) or 20 mL of Agar Medium B-1 (calculated sodium content: 0.06 mM; calculated chloride content: ~0). After inoculation, the edges of the agar plates were wrapped with parafilm to avoid evaporation. The agar plates were incubated at 28° C. for 2 to 4 weeks to observe good growth. No growth was observed on Agar Medium A-1 and Agar Medium B-1 after 4 weeks of incubation. Good growth was observed on Agar Medium A and Agar Medium B after two weeks of incubation. After two weeks of incubation, the growth from Agar Medium A and Agar Medium. B were transferred to a fresh plates of Agar Medium A and Agar Medium B, respectively. The re-streaked agar plates were again incubated at 28° C. to observe growth. Good growth on these re-streaked agar plates were observed in about two to three weeks of incubation and summarized in the table below.

TABLE 14

Observation of growth of Salinispora tropica NPS021184 grown on agar medium A1.Kc4C and A1.Ks4C (second streak)

| Agar Medium | Week 1 | Week 2 | Week 3 | Week 4 |
|---|---|---|---|---|
| A1.Kc4C | ++ | ++ | +++ | +++ |
| A1.Ks4C | −/+ | + | ++ | +++ |

Key:
− no growth;
−/+ poor growth;
+ fair growth;
++ growth;
+++ very good growth

EXAMPLE 8

Growth of Salinispora tropica NPS021184 and Production of NPI-0052 in Media Containing Trace Amounts of Sodium Ion (Calculated Value Based on 2.6 mg/L NaF: 0.06 mM; ICP-MS Analysis: 9.3 to 11 mM)

Seed cultures were prepared by inoculating a frozen stock of Salinispora tropica NPS021184 into seed medium.

The seed medium consisted of the following per liter of DI water: 10 g Starch, 4 g Hy Soy, 4 g Yeast Extract, 1 g $CaCO_3$, and 40 mg $Fe_2(SO_4)_3$. The seed medium was then supplemented with a chemically defined salt formulation containing trace amount of sodium (0.06 mM) from NaF. This supplemented medium is referred to as SHY.KCD. The composition of this chemically defined salt formulation is shown in the table below

| Salt component | Per liter of DI $H_2O$ |
|---|---|
| KCl | 30 g |
| $MgSO_4 \cdot 7H_2O$ | 4.29 g |
| $CaCl_2 \cdot 2H_2O$ | 0.43 g |
| $SrCl_2$ | 15 5 mg |
| $H_3BO_3$ | 21.5 mg |
| NaF | 2.6 mg |
| $CoCl_2 \cdot 6H_2O$ | 208 μg |

The first seed culture (10 mL medium) in a 50-mL culture tube was incubated for 72 hours before inoculating 5 mL of the first seed culture into the second seed medium with the same composition as the first seed medium including supplemental salts. The second seed culture (100 mL medium in a 500-mL Erlenmeyer flask) was incubated for 48 hours before inoculating 5 mL of the second seed culture into the production medium (100 mL in a 500-mL Erlenmeyer flask) supplemented with trace amount of sodium ion (0.06 mM from NaF).

Per liter of DI H2O, the production medium consisted of: 10 g Starch, 4 g Hy Soy, 4 g Yeast Extract, 1 g $CaCO_3$, 40 mg $Fe_2(SO_4)_3$, 100 mg KBr. The production medium was then supplemented with a chemically defined salt formulation. This supplemented medium is referred to as SHY-.KcMC. The chemically defined salt formulation consisted of:

| Salt component | Per liter of DI $H_2O$ |
|---|---|
| KCl | 30 g |
| $CaCl_2 \cdot 2H_2O$ | 0.43 g |
| $SrCl_2$ | 15 5 mg |
| $H_3BO_3$ | 21.5 mg |
| NaF | 2.6 mg |
| $CoCl_2 \cdot 6H_2O$ | 52 μg |

Because seed medium and production medium were supplemented with 0.06 mM sodium ion derived from NaF (2.6 mg/L). The calculated amount of sodium ion present in the production medium was 0.06 mM. The amount of key ions in the production medium by ICP-MS analysis is listed in the following table.

TABLE 15

Determination of the amount of Particular ions (mM) in Media SHY.KCD and SHY.KcMC by ICP-MS analysis

| Medium | [Na] | [Cl] | [K] | [Mg] | [Co] | [S] | [Ca] | [Fe] |
|---|---|---|---|---|---|---|---|---|
| SHY.KCD | 9.3 | 463 | 498 | 20 | $1 \times 10^{-3}$ | 22 | 3.6 | 0.12 |
| SHY.KcMC | 11 | 477 | 468 | 0.75 | $3.7 \times 10^{-4}$ | 1.7 | 4.1 | 0.12 |

After about 24 hour incubation into the production culture, sterile XAD-7 resin slurry was added to the production cultures in a final concentration of 20 g/L. The production culture was then further incubated and harvested at various time points to determine productivity.

3.5 mL of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. freezer before HPLC analysis. The dried extract was resuspended in 320 μL DMSO and injected into HPLC using the TFS7 method for analysis.

The production of Salinosporamide A, NPI-0047 and NPI-2065 was monitored by Agilent HP1100 HPLC using an ACE C-18 reversed-phase column (4.6×150 mm), and an isocratic solvent system consisting of 67% water (0.01% TFA) and 33% acetonitrile (0.01% TFA). The flow rate was 1.5 mL/min with the detector wavelength set at 210 nm and column temperature 35° C.

TABLE 16

Production of Salinosporamide A, NPI-0047 and NPI-2065 by *Salinispora tropica* NPS021184 grown in production medium containing 0.06 mM sodium ion (calculated value) and 11 mM sodium ion determined by ICP-MS analysis.

| Culture Age (days) | Titers (mg/L) | | |
|---|---|---|---|
| | Salinosporamide A | NPI-0047 | NPI-2065 |
| 3 | 88 | 0.2 | 0.4 |
| 4 | 188 | 0.5 | 2.4 |
| 5 | 211 | 0.7 | 2.8 |
| 6 | 243 | 0.9 | 3.7 |

*Salinispora tropica* NPS21184 can be grown in medium SHY.KCD containing very low concentrations of sodium (9.3 mM by ICP-MS analysis) and medium SHY.KcMC containing very low concentrations of sodium (11 mM by ICP-MS analysis). *Salinispora tropica* NPS21184 grown in the above low sodium media supported good production of Salinosporamide A (243 mg/L). The sodium content in SHY.KCD and SHY.KcMC should be very similar with only minor differences in the ICP-MS analysis. This minor difference in the sodium content between SHY.KCD and SHY.KcMC is insignificant.

EXAMPLE 9

ICP-MS Analysis of Trace Elements in Media

Inductively coupled plasma mass spectrometry (ICP-MS) is a powerful tool for detecting and analyzing trace elements. Over the past few years, ICP-MS has become the technique of choice in many analytical laboratories for providing the accurate and precise measurements of trace elements. In ICP-MS, a plasma or gas consisting of ions, electrons and neutral particles, is formed from argon gas, which is then utilized to atomize and ionize the elements in the sample matrix. These resulting ions are the passed through a series of apertures into a high vacuum mass analyzer where the isotopes of the elements are identified by their mass-to-charge ratio. The intensity of a specific peak in the mass spectrum is proportional to the amount of the elemental isotope from the original sample.

All samples for trace element analysis were analyzed by inductively coupled plasma dynamic reaction cell mass spectrometry (ICP-DRC-MS) on a Perkin-Elmer ELAN DRC II. Aliquots of each sample are introduced into a radio frequency (RF) plasma where energy-transfer processes cause desolvation, atomization, and ionization. The ions are extracted from the plasma through a differentially-pumped vacuum interface and travel through a pressurized chamber (DRC) containing a specific reactive gas which preferentially reacts with interfering ions of the same target mass to charge ratios (m/z). A solid-state detector detects ions transmitted through the mass analyzer, on the basis of their mass-to-charge ratio (m/z), and the resulting current is processed by a data handling system.

Different reaction gases and settings are applied depending on the target analyte and projected interference. Comparison of the different isotopes, reaction gases, and reaction gas settings allow for interference monitoring and selection of optimum instrument settings depending on each sample matrix type and element.

Instrument Parameters

Tables 17, 18, and 19 show the ICP-DRC-MS operating conditions for the different elements.

TABLE 17

ICP-DRC-MS Operating Conditions and Parameters

| Parameter | Setting/Type |
|---|---|
| Nebulizer | Meinhard Type A Quartz |
| RF Power | 1200 W |
| Plasma Ar Flow | 15 L/min |
| Nebulizer Ar Flow | 0.87 L/min |
| Injector | 2.0 mm I.D. Quartz |
| Monitored ion (m/z) | $^{23}$NaN$^+$, $^{39}$KN$^+$, $^{24}$Mg$^+$, $^{26}$Mg$^+$, $^{40}$Ca$^+$, $^{43}$Ca$^+$, $^{44}$Ca$^+$, $^{54}$Fe$^+$, $^{56}$Fe$^+$, |
| Reaction Gas | NH$_3$ |
| NH3 Flow | 0.8 mL/min |
| RPq | 0.7 |

TABLE 18

ICP-DRC-MS Operating Conditions and Parameters

| Parameter | Setting/Type |
|---|---|
| Nebulizer | Meinhard Type A Quartz |
| RF Power | 1200 W |
| Plasma Ar Flow | 15 L/min |
| Nebulizer Ar Flow | 0.87 L/min |
| Injector | 2.0 mm I.D. Quartz |
| Monitored ion (m/z) | $^{48}$SO$^+$, $^{50}$SO$^+$ |
| Reaction Gas | NH$_3$ |
| O2 Flow | 0.9 mL/min |
| RPq | 0.7, 0.75, 0.6 |

TABLE 19

ICP-DRC-MS Operating Conditions and Parameters

| Parameter | Setting/Type |
|---|---|
| Nebulizer | Meinhard Type A Quartz |
| RF Power | 1200 W |
| Plasma Ar Flow | 15 L/min |
| Nebulizer Ar Flow | 0.87 L/min |
| Injector | 2.0 mm I.D. Quartz |
| Monitored ion (m/z) | $^{35}$Cl$^+$, $^{37}$Cl$^+$ |
| Reaction Gas | none |
| RPq | 0.25 |

The complex medium components, such as yeast extract and Hy Soy, are known to contain trace elements such as sodium, potassium, magnesium and chloride. Therefore, adding these nutrients into the medium introduces the above trace elements to the growth medium. This phenomenon is known as carryover effect. Therefore, even without addition of the salt of the above elements to the growth medium, the growth medium can contain the above elements contributed from the complex nutrient such as yeast extract and Fly Soy. In order to determine the carryover effect by yeast extract, Hy Soy and the other nutrient components, we use ICP-MS technique to analyze the presence of the trace elements present in the following media:

TABLE 20

Determination of the amount of Particular ions (mM) in Media and seawater by ICP-MS analysis

| Media | [Na] | [Cl] | [K] | [Mg] | [Co] | [Si] | [Ca] | [Fe] |
|---|---|---|---|---|---|---|---|---|
| 4 g/L Yeast Extract (USB 23547, lot # 117942) in deionized water | 1.8 | ND | 3.4 | 0.10 | $6 \times 10^{-5}$ | 2.5 | NT | NT |
| 4 g/L Hy Soy (Kerry Biosciences 5X59089, lot # M031936) in deionized water | 4.9 | ND | 2.8 | 0.34 | $1 \times 10^{-5}$ | 2.1 | NT | NT |
| 4 g/L Yeast Extract (USB 23547, lot # 117942) + 4 g/L Hy Soy (Kerry Biosciences 5X59089, lot # M031936) in deionized water | 8.3 | 3.6 | 8.9 | 0.56 | $7 \times 10^{-5}$ | NT | NT | NT |
| 10 g/L Starch (USB 21695, lot# 118386) + 4 g/L Yeast Extract (USB 23547, lot # 117942) + 4 g/L Hy Soy (Kerry Biosciences 5X59089, lot # M031936) in deionized water | 7.7 | 4.6 | 7.3 | 0.63 | $6 \times 10^{-5}$ | 1.5 | 0.42 | 0.012 |
| Medium SHY.10.4.4* in deionized water | 7.6 | 4.7 | 7.2 | 0.61 | $7 \times 10^{-5}$ | 2.7 | 0.84 | 0.17 |
| Medium SHY.10.4.4* + 24 g/L NaCl in deionized water | 416 | 505 | 7.0 | 0.69 | $7 \times 10^{-5}$ | 3.4 | 1.2 | 0.17 |
| Medium SHY.10.4.4* + In house salt formulation I (production)** | 426 | 507 | 15 | 0.64 | 0.45 | 3.3 | 1.2 | 0.17 |
| Instant Ocean (30 g/L) | 424 | 542 | 8.6 | 47 | ND | 31 | NT | NT |
| A1*** in deionized water | 5.2 | ND | 4.2 | 0.19 | $6 \times 10^{-5}$ | 0.39 | 0.08 | 0.008 |
| Seawater**** | 487 | 530 | 10 | 61 | $5 \times 10^{-5}$ | 32 | 11 | $2 \times 10^{-4}$ |

NT = Not Tested
ND = Not Detected (below detection limit)
  *Medium SHY.10.4.4
10 g/L Starch (USB 21695)
4 g/L Hy Soy (Kerry Biosciences M031936)
4 g/L Yeast Extract (USB 23547)
40 mg/L Ferric sulfate
100 mg/L KBr
1 g/L Calcium carbonate
  **In-house salt formulation I (Production)
24 g/L NaCl
686.8 mg/L KCl
429.3 mg/L CaCl$_2$•2H$_2$O
15.5 mg/L SrCl$_2$
21.5 mg/L H$_3$BO$_3$
2.6 mg/L NaF
  ***Medium A1
10 g/L Starch (USB 21695)
2 g/L Peptone (USB 20048)
4 g/L Yeast extract (USB 23547)
****Seawater from the Pier of University of California at San Diego, La Jolla, California.

It is clear from the above ICP-MS analysis that the medium components from SHY.10-4-4 in deionized water, and a combination of starch, Hy Soy and yeast extract, the medium components contribute 7.6 to 8.3 mM of sodium to the growth medium without addition of any sodium salt to the growth medium. The major source of carryover of sodium is Hy Soy. A 4 g/L solution of this media component contained 4.9 mM of sodium. The carryover of chloride from the medium components is about 3.6 to 4.7 mM. For the A1 medium in deionized water, the carryover of sodium is about 5.2 mM. The sodium content of the seawater collected at the Pier of the University of California at San Diego, La Jolla, Calif. is 487 mM by ICP-MS analysis.

EXAMPLE 10

Preparation of Low Sodium Frozen Vegetative Stock *Salinispora tropica* CNB440, CNB476 and NPS021184 in Seed Medium Containing Trace Amount of Sodium Ion (0.06 mM Calculated Value; ~9-10 mM Determined by ICP-MS Analysis)

To prepare the Low Sodium Frozen Stock, the first seed culture was prepared by inoculating two frozen stock vials of each strain of *Salinipora tropica* CNB3440, CNB476 and NPS021184 (previously prepared in 2.4% NaCl medium or 3% INSTANT OCEAN® commercial salt formulation medium) into seed medium consisting of the following per liter of DI H$_2$O: 10 g Starch, 4 g Fly Soy, 4 g Yeast Extract, 40 mg Fe$_2$(SO$_4$)$_3$. This seed medium was then supplemented with a chemically defined salt formulation. The chemically defined salt formulation included. The seed medium with this salt supplement is the SHY.B4C medium.

| Salt component | Per liter of DI H$_2$O |
|---|---|
| NaCl | 24 g |
| KCl | 0.69 g |
| MgSO$_4$•7H$_2$O | 4.29 g |
| CaCl$_2$•2H$_2$O | 0.43 g |
| SrCl$_2$ | 15 5 mg |
| H$_3$BO$_3$ | 21.5 mg |
| NaF | 2.6 mg |
| CoCl$_2$•6H$_2$O | 208 μg |

The first seed culture (100 mL medium) in a 500-mL Erlenmeyer flask was incubated for 72 hours at 250 rpm and 28° C. 45 mL each of the first seed cultures was transferred to a sterile 50-mL centrifuge tube. The centrifuge tubes were centrifuged at 3,500 rpm for 10 min. The supernatant was discarded and 40 ml of the wash medium was added to each centrifuge tube. The Wash Medium consisted of the following per liter of DI $H_2O$: 10 g Starch, 4 g Hy Soy, 4 g Yeast Extract, 40 mgFe$_2$(SO$_4$)$_3$, 30 g KCl. The centrifuge tubes were gently reverted several times to reused the pellet into the Wash Medium and the centrifuge tubes were centrifuged at 3,500 rpm for 10 min. The supernatant was discarded and the centrifuge wash protocol was repeated with fresh Wash Medium. After discarding the supernatant at the end of the second wash, 45 mL of fresh Wash Medium was added to each centrifuge tube to re-suspend the culture before transferring together to a sterile 500 mL Erlenmeyer flask. Five mL of Wash Medium was used to rinse each centrifuge tube and the rinses were added to the cell suspension in the 500-mL Erlenmeyer flask (total volume of the cell suspension was ~100 mL). The washing procedure served to remove the sodium chloride, more specifically, the sodium ion, that was present in the first seed medium. Five mL of each of the washed cultures was inoculated into a second stage seed flask containing medium with the following composition per liter of D.I. water, two flasks were prepared for each strain: 10 g Starch, 4 g Hy Soy, 4 g Yeast Extract, 1 g CaCO$_3$, and 40 mg Fe$_2$(SO$_4$)$_3$. The two second seed media were then supplemented with a chemically defined salt formulation containing very low concentration of 0.06 mM sodium ion derived from NaF. The chemically defined salt formulation included (per liter of DI $H_2O$):

| SHY.KCA | SHY.KCD |
|---|---|
| 30 g KCl | 30 g KCl |
| 4.29 g MgSO$_4$•7H$_2$O | 4.29 g MgSO$_4$•7H$_2$O |
| | 0.43 g CaCl$_2$•2H$_2$O |
| | 15.5 mg SrCl$_2$ |
| | 21.5 mg H$_3$BO$_3$ |
| | 2.6 mg NaF |
| | 208 µg CoCl$_2$•6H$_2$O |

The second seed cultures were incubated for 24 to 96 hours at 250 rpm and 28° C. to achieve the following dry cell weights:

TABLE 21

Dry cell weight of *Salinispora tropica* CNB440, CNB476 and NPS21184 grown in Media SHY.KCA and SHY.KCD

| | | Dry Cell Weight (mg/mL) | | | |
|---|---|---|---|---|---|
| Strain | Medium | 24 h | 48 h | 72 h | 96 h |
| CNB440 | SHY.KCA | 1.39 | 1.36 | 1.57 | 1.56 |
| | SHY.KCD | 2.55 | 1.99 | 2.55 | 2.68 |
| CNB476 | SHY.KCA | 1.43 | 1.15 | 1.18 | 1.52 |
| | SHY.KCD | 2.17 | 2.19 | 2.07 | 2.35 |
| NPS21184 | SHY.KCA | 0.73 | 3.51 | 5.50 | 3.41 |
| | SHY.KCD | 2.60 | 3.27 | 5.39 | 4.13 |

Strains CNB440 and CNB476 grew better in the SHY.KCD medium than in the SHY.KCA medium. SHY.KCD medium has more ion supplements than SHY.KCA. These ion supplements are responsible for supporting better grow of strains CNB440 and CNB476. The initial growth rate of strain NPS21184 was faster in the SHY.KCD medium than in the SHY.KCA medium. The growth yield of strain NPS21184 is similar in SHY.KCA and SHY.KCD media. Strain. NPS21184 has better growth rate and yield than strains CNB440 and CNB476. After 48 hours of incubation, 5 mL each of the second seed cultures of NPS21184 were inoculated into the corresponding third seed media SHY.KCA and SHY.KCD, with the same composition as the second seed media. Since the growth of strains CNB440 and CNB476 in medium SHY.KCA was poor, the cultures growing in medium SHY.KCA were not moved forward for preparation of freeze stock. In order to compensate the lower in growth yield of strains CNB440 and CNB476 in SHY.KCD medium, 45 mL each of the 96-hour seed cultures were centrifuged in a sterile 50-mL centrifuge tube. 35 mL of the supernatant was withdrawn from the centrifuge tube to concentrate the culture by 4.5 fold (from 45 mL to 10 mL culture). 5 mL each of the concentrated cultures of CNB440 and CNB476 in KCD was used to inoculate into the third seed medium SHY.KCD. The third seed cultures (100 mL medium in a 500-mL Erlenmeyer flask) were incubated for 24 hours to 120 hours at 250 rpm and 28° C. to achieve the following dry cell weight.

TABLE 22

Dry cell weight of *Salinispora tropica* CNB440, CNB476 and NPS21184 grown in Media SHY.KCA and SHY.KCD

| | | Dry Cell Weight (mg/mL) | | | | |
|---|---|---|---|---|---|---|
| Strain | Medium | 24 h | 48 h | 72 h | 96 h | 120 h |
| CNB440 | SHY.KCD | 1.63 | 2.10 | 2.58 | 2.79 | 2.73 |
| CNB476 | SHY.KCD | 1.78 | 1.68 | 1.23 | 1.98 | 2.77 |
| NPS21184 | SHY.KCA | 2.10 | 3.87 | 0.0 | 0.07 | ND* |
| | SHY.KCD | 1.91 | 6.16 | 6.57 | 7.77 | 6.03 |

*ND = Not Determined

Strain NPS21184 grew very well in SHY.KCD medium with the majority of the growth completed at 48 hours (6.16 mg/L dry cell weight) and yielding the highest growth yield of 7.77 mg/L dry cell weight. Since good growth rate of NPS21.184 in SHY.KCD medium was observed, 8 mL each of the 48-hour third seed culture was added to a sterile 50-mL culture tube (25×150 mm) containing 2 mL of 50% glycerol. The culture tubes were incubated for one hour at 250 rpm and 28° C. 1.5-mL portions of the culture were transferred to sterile cryovials (1.8 mL capacity). The freeze stock is stored at −80° C. freezer until use. Alternatively, the culture tube containing the culture in 10% glycerol is stored at −80° C. freezer until use. We have successfully prepared the frozen freeze stock of strain NPS21184 in SHY.KCD medium that contains very low sodium content (9.3 mM sodium by ICP-MS analysis, see table below).

Strain NPS21184 grew well in SHY.KCA medium, which has the same sodium concentration as the SHY.KCD medium (see table below) for the first 48 hours incubation yielding a dry cell weight of 3.87 mg/L. However, the culture lost viability with further incubation in SHY.KCA medium, indicating again that the importance of the additional ion supplements, besides potassium and magnesium, in SHY.KCD medium for supporting growth of *Salinispora tropica* in low sodium medium. No frozen stock of strain NPS21184 in SHY.KCA medium was prepared.

To prepare freeze stocks of strains CNB440 and CNB476 in KCD medium, the 120-hour cultures were first concentrated 2.3-3.9 fold to compensate for the low cell yield. Four×35 mL cultures each of strains CNB440 and CNB476 in 50-mL centrifuge tubes were centrifuged at 3,000 rpm for 15 min. Twenty mL supernatant from each tube of strain. CNB440 was withdrawn and the concentrated cultures were combined to yield ~45 mL of concentrated cultures ~2.3 fold concentrate). Twenty-six mL supernatant from each tube of strain CNB476 was withdrawn and the concentrated cultures were combined to yield ~36 mL of concentrated cultures In order to confirm the growth and the productivity of the Low Sodium Frozen Stock of NPS21184 prepared in the low sodium medium SHY.KCD, the frozen stock prepared in Example 10 was used to inoculate 10 mL each of the following seed media (per liter of DI $H_2O$) in a 50-mL culture tube (25×150 mm):

| SHY.B4C | SHY.KCA | SHY.KCD |
|---|---|---|
| 10 g Starch | 10 g Starch | 10 g Starch |
| 4 g Hy Soy | 4 g Hy Soy | 4 g Hy Soy |
| 4 g Yeast Extract | 4 g Yeast Extract | 4 g Yeast Extract |
| 40 mg $Fe_2(SO_4)_3$ | 40 mg $Fe_2(SO_4)_3$ | 40 mg $Fe_2(SO_4)_3$ |
| 24 g NaCl | 30 g KCl | 30 g KCl |
| 0.69 g KCl | 4.29 g $MgSO_4 \cdot 7H_2O$ | 4.29 g $MgSO_4 \cdot 7H_2O$ |
| 4.29 g $MgSO_4 \cdot 7H_2O$ | 1 g $CaCO_3$ | 0.43 g $CaCl_2 \cdot 2H_2O$ |
| 0.43 g $CaCl_2 \cdot 2H_2O$ | — | 15.5 mg $SrCl_2$ |
| 15.5 mg $SrCl_2$ | — | 21.5 mg $H_3BO_3$ |
| 21.5 mg $H_3BO_3$ | — | 2.6 mg NaF |
| 2.6 mg NaF | — | 208 µg $CoCl_2 \cdot 6H_2O$ |
| 208 µg $CoCl_2 \cdot 6H_2O$ | — | 1 g $CaCO_3$ |

(~3.9 fold concentrate). Eight mL each of the concentrated 120-hour third seed culture was added to a sterile 50-mL culture tube (25×150 mm) containing 2 mL of 50% glycerol. The culture tubes were incubated for one hour at 250 rpm and 28° C. 1.5-mL portions of the culture were transferred to sterile cryovials (1.8 mL capacity). The freeze stock was stored at −80° C. freezer until use. Alternatively, the culture tube containing the culture in 10% glycerol is stored at −80° C. freezer until use. Low Sodium Frozen Stocks of strains NPS429 and NPS465 in SHY.KCD medium have been prepared which contain very low sodium content (9 to 10 mM sodium by ICP-MS analysis, see Table below).

TABLE 23

Determination of the amount of Particular ions (mM) present in the media by ICP-MS analysis

| Media | [Na] | [Cl] | [K] | [Mg] | [Co] | [S] | [Ca] | [Fe] |
|---|---|---|---|---|---|---|---|---|
| $1^{st}$ Seed Medium (SHY.B4C) | 413 | 493 | 6.1 | 21 | $1 \times 10^{-3}$ | 23 | 3.9 | 0.17 |
| Wash Medium | 7.1 | 494 | 434 | 0.62 | $7 \times 10^{-5}$ | 3.8 | 1.4 | 0.17 |
| SHY.KCA | 10 | 487 | 499 | 22 | $7 \times 10^{-5}$ | 22 | 1.1 | 0.14 |
| SHY.KCD | 9.3 | 463 | 498 | 20 | $1 \times 10^{-3}$ | 22 | 3.6 | 0.12 |

Even though the only sodium salt added to the Wash Medium SHY.KCA and SHY.CKD is sodium fluoride, which supplies 0.06 mM sodium to the above media, ICP-MS analysis of these media showed that the sodium concentration in these media were 9 to 10 mM. The majority of the sodium (~8 mM) in these media was derived from yeast extract and Hy Soy (see Table 20 in Example 9).

Media containing low sodium (9 to 10 mM, ~2% of the sodium content of seawater) were developed to support the growth of *Salinispora tropica* CNB440, CNB476 and NPS21184 for the preparation of low sodium vegetative frozen stock of these *Salinispora tropica* strains.

EXAMPLE 11

Growth of *Salinispora tropica* NPS021184 and Production of Salinosporamide A in Seed and Production Media Containing Trace Amount of Sodium Ion (0.06 mM, Calculated Value; 9 to 10 mM by ICP-MS Analysis) Using Low Sodium Frozen Stock While the amount of known sodium salt, sodium fluoride, added to the media SHY.KCA and SHY.KCD was 2.6 mg/L (0.06 mM sodium), ICP-MS analysis demonstrated that the sodium concentration in KCA and KCD were 9 and 10 mM, respectively (see table 23 of Example 10). The sodium content in Medium SHY.B4C was 413 mM, by ICP-MS analysis. Media SHY.KCA and SHY.KCD contained very low concentration of sodium, about 40-fold less than Medium SHY.B4C.

1.8 mL of the frozen stock each was used to inoculate 10.2 mL first seed medium SHY.B4C and medium SHY.KCA. (total volume: 12 mL) to yield an inoculum size of 15%. 1.2 mL, 2.4 mL and 3.6 mL of the frozen stock were inoculated into 10.8 mL, 9.6 mL and 8.4 mL of first seed medium SHY.KCD (total volume: 12 mL) to yield inoculums size of 10%, 20% and 30%, respectively. 1.8-mL of frozen stock of NPS21184 (i.e., prepared in 24 g/L NaCl medium or 30 g/L INSTANT OCEAN® commercial salt medium) was also used to inoculate 10.2 mL first seed medium SHY.B4C as a control condition of high sodium medium (saline fermentation condition). The first seed cultures were incubated for 72 hours at 250 rpm and 28° C. yielding the following dry cell weight data.

TABLE 24

Dry cell weight of first seed cultures (72 hours)

| [Sodium] in Freeze Preparation* | % Inoculum | [Sodium] in Medium* | Dry Cell Weight (mg/mL) |
|---|---|---|---|
| A) 426 mM** | 15% | SHY.B4C (413 mM) | 4.2 |
| B) 9.3 mM | 15% | SHY.B4C (413 mM) | 4.4 |
| C) 9.3 mM | 15% | SHY.KCA (10 mM) | 2 |
| D) 9.3 mM | 10% | SHY.KCD (9.3 mM) | 4.4 |
| E) 9.3 mM | 20% | SHY.KCD (9.3 mM) | 4.6 |
| F) 9.3 mM | 30% | SHY.KCD (9.3 mM) | 4.6 |

*Sodium concentration of SHY.B4C, SHY.KCA and SHY.KCD was determined by ICP-MS analysis (Table 23 of Example 10)
**Sodium concentration was estimated from the condition of Medium SHY.10.4.4 + 24 g/L NaCl in deionized water in Table 20 of Example 9

It is clear from the dry cell weight data that the freeze preparation of NPS21184 in the low sodium medium can support the good growth yield in Medium SHY.KCD, a low sodium medium that is supplemented with trace metal ions other than sodium. Without the addition of other ions in Medium. SHY.KCA with similar sodium concentration as medium SHY.KCD, the growth yield was significantly reduced by more than 50%. It is also important to observe that the Low Sodium Frozen Stock prepared in the low sodium medium. SHY.KCD (9.3 mM) has the same growth yield as the frozen stock prepared in the high sodium medium (426 mM in NaCl based medium).

After incubating the above first seed cultures for 72 hours at 250 rpm and 28° C., 0.5 mL of each culture was inoculated into 10 mL of the second seed medium (in 50-mL culture tubes) having the same composition as the first seed medium. The second seed cultures were incubated for 72 to 96 hours and yielding the following daily dry cell weight data:

TABLE 25

Dry cell weight data for second seed cultures

| [Sodium] in Freeze Preparation* | Medium | % Inoculum | | Dry cell weight (mg/mL) | | | |
|---|---|---|---|---|---|---|---|
| | | $1^{st}$ seed | $2^{nd}$ seed | 24 h | 48 h | 72 h | 96 h |
| A) 426 mM** | SHY.B4C | 15% | 5% | 2.6 | 3.6 | 4.4 | 4.2 |
| B) 9.3 mM | SHY.B4C | 15% | 5% | 1.8 | 2.8 | 3.9 | 4.8 |
| C) 9.3 mM | SHY.KCA | 15% | 5% | 0.49 | 1.0 | 0.65 | ND |
| D) 9.3 mM | SHY.KCD | 10% | 5% | 1.4 | 3.2 | 3.4 | ND |
| E) 9.3 mM | SHY.KCD | 20% | 5% | 1.9 | 2.9 | 3.9 | 4.2 |
| F) 9.3 mM | SHY.KCD | 30% | 5% | 1.1 | 3.6 | 3.2 | 4.4 |

*Sodium content determined by ICP-MS analysis
**Sodium concentration estimated from the condition of Medium SHY.10.4.4 + 24 g/L NaCl in deionized water in Table 20 of Example 9
ND = Not determined The dry cell weight data from the second seed cultures again support the finding that the Low Sodium Frozen Stock preparation of NPS21184 can support good cell growth in low sodium medium (Medium SHY.KCD) which includes trace metal ions other than sodium. The Low Sodium Frozen Stock has the same growth yield as the frozen stock prepared in a high sodium medium. The importance of the metal ions present in Medium SHY.KCD is even more evident in that the second seed culture with Medium SHY.KCA yielded lower dry cell weight than the first seed culture. The dry cell weight of SHY.KCA medium in the second seed culture was only about 25% of the SHY.KCD medium.

To determine the production profile of Low Sodium Frozen Stock of NPS21184 grown up in low sodium medium (Medium SHY.KCD), 0.5 mL of the 48-hour sample of the second seed culture from Condition D in Table 25 ($1^{st}$ seed inoculum: 10%; second seed inoculum: 5%; both in Medium SHY.KCD) was used to inoculate 10 mL of Medium SHY.KCD in 50-mL culture tubes. Five mL of the 48-hour sample of the second seed culture of control Condition A in Table 25 ($1^{st}$ seed inoculum: 15%; $2^{nd}$ seed inoculum: 5%; both in Medium SHY.B4C) was also used to inoculate 10 mL of Medium SHY.B4C in 50-mL culture tubes. The production cultures were incubated at 250 rpm and 28° C.

About 24 hour after inoculation, sterile XAD-7 resin slurry was added to the production cultures in a final concentration of ~30 g/L. The production culture was then further incubated and harvested at various time points to determine productivity.

3.5 mL of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. before HPLC analysis. The dried extract was resuspended in 320 μL DMSO and injected into HPLC using the 00TF14 method for analysis.

The production of Salinosporamide A, NPI-0047 and NPI-2065 was monitored by Agilent HP1100 HPLC using an ACE C-18 reversed-phase column (4.6×150 mm), and solvent system consisting of water (0.01% TFA) as solvent A and acetonitrile (0.01% TFA) as solvent B. The elution was started at 100% solvent A for 1 min, 100% solvent A to 35% solvent A gradient in 7 min, held at 35% solvent A for 11 min, 35% solvent A to 100% solvent B in 8 min and held at 100% solvent B for 9 min at a flow rate of 1.5 mL/min with the detector wavelength set at 210 nm and column temperature 35° C.

TABLE 26

Comparison of production of Salinosporamide A, NPI-0047 and NPI-2065 by *Salinispora tropica* NPS021184 grown in production medium containing high and low sodium concentration.

| [Sodium] in freeze prep* | [Sodium] in seed and production media* | Day 4 Titers (mg/L) | | | Day 5 Titers (mg/L) | | | Day 6 Titers (mg/L) | | |
|---|---|---|---|---|---|---|---|---|---|---|
| | | NPI-0047 | NPI-2065 | Sal A | NPI-0047 | NPI-2065 | Sal A | NPI-0047 | NPI-2065 | Sal A |
| 426 mM | 413 mM | 0.52 | 6.7 | 261 | 0.97 | 8.4 | 324 | 0.73 | 8.2 | 310 |
| 9.3 mM | 9.3 mM | 0.6 | 2.4 | 163 | 0.77 | 3.9 | 242 | 0.50 | 3.6 | 209 |

*Sodium content determined by ICP-MS analysis

The maximum production of Salinosporamide A by NPS21184 in the low sodium medium (9.3 mM sodium, SHY.KCD) was about 75% of the high sodium medium (413 mM sodium, SHY.B4C). The above data demonstrates that strain NPS21184 can be grown in low sodium medium (9.3 mM) with good cell growth and produce substantial quantities of Salinosporamide A. This data showed about 75% of the highest yield of the high sodium (413 mM), saline fermentation condition.

EXAMPLE 12

Comparison of Growth of Low Sodium Frozen Stock of *Salinispora tropica* CNB440, CNB476 and NPS021184 in Low Sodium Medium and Production Profiles of these Strains in Low Sodium Medium Low Sodium Frozen Stocks of *Salinispora tropica* CNB440, CNB476 and NPS021184 prepared in example 10 were used to inoculate 10 mL each of the following seed medium SHY.KCD in a 50-mL culture tube (25×150 mm).

SHY.KCD (per liter of DI $H_2O$)
10 g Starch
4 g lily Soy
4 g Yeast extract
1 g $CaCO_3$
40 mg $Fe_2(SO_4)_3$
0.69 g
4.29 g $MgSO_4.7H_2O$
0.43 g $CaCl_2.2H_2O$
15.5 mg $SrCl_2$
21.5 mg $H_3BO_3$
2.6 mg NO
208 µg $CoCl_2.6H_2O$ 1 mL of the frozen stock each was used to inoculate 10 mL first seed SHY.KCD medium to yield an inoculum size of 10%. After incubating the above first seed cultures of CNB476 and NPS21184 for 72 hours at 250 rpm and 28° C., 5 mL of each culture was inoculated into 100 mL of the second seed medium (in 500-mL Erlenmeyer flask) having the same composition as the first seed medium. For CNB440, the first seed culture was grown for 5 days. 10 mL of the first seed culture was used to inoculate 100 mL of the second seed medium in a 500-mL Erlenmeyer flask. The second seed cultures were incubated for 48 to 96 hours and yielding the following dry cell weight data:

TABLE 27

Dry cell weight of *Salinispora tropica* CNB440, CNB476 and NPS21184 in low sodium (9.3 mM) medium SHY.KCD

| Strain | Dry cell weight (mg/mL) | | |
|---|---|---|---|
| | 48 hours | 72 hours | 96 hours |
| NPS21184 | 5.7 | 4.9 | 5.3 |
| CNB476 | 5.3 | 6.3 | 7.5 |
| CNB440 | 2.3 | 4.0 | 5.2 |

The dry cell weight data from the second seed cultures confirmed the finding that the Low Sodium Frozen Stocks of CNB440, CNB476 and NPS21184 prepared in the low sodium medium (9.3 mM) can support good cell growth in low sodium seed medium that is supplemented with trace metal ions other than sodium. The Low Sodium Frozen Stocks of strains CNB440, CNB476 and NPS21184 grew very well in the low sodium medium (9.3 mM sodium) with dry cell weights of 5.2 to 7.5 mg/mL. While the growth rate of CNB440 is slower in the low sodium medium, it achieved the same dry cell weight as NPS21184 after 96 hours incubation.

To determine the production profile of Low Sodium Frozen Stocks cultures of CNB440, CNB476 and NPS21184 grown up in low sodium production medium, 5 mL each of the 48-hour second seed culture samples of CNB476 and NPS21184 was used to inoculate 100 mL of production medium having the same composition as the seed medium in a 500-mL mL Erlenmeyer flasks. For CNB440, 5 mL of the 72 hour second seed culture sample was used to inoculate 100 mL of production medium having the same composition as the seed medium in a 500-mL Erlenmeyer flasks. The production cultures were incubated at 250 rpm and 28° C.

About 24 hour after inoculation, sterile XAD-7 resin slurry was added to the production cultures in a final concentration of ~20 g/L. The production culture was then further incubated and harvested at various time points to determine productivity.

3.5 mL of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. freezer before HPLC analysis. The dried extract was resuspended in 320 µL DMSO and injected into HPLC using the 00TF14 method for analysis.

The production of Salinosporamide A, NPI-0047 and NPI-2065 was monitored by Agilent HP1100 HPLC using an ACE C-18 reversed-phase column (4.6×150 mm), and solvent system consisting of water (0.01% TFA) as solvent A and acetonitrile (0.01% TFA) as solvent B. The elution was started at 100% solvent A for 1 min, 100% solvent A to 35% solvent A gradient in 7 min, held at 35% solvent A for 11 min, 35% solvent A to 100% solvent B in 8 min and held at 100% solvent B for 9 min at a flow rate of 1.5 mL/min with the detector wavelength set at 210 nm and column temperature 35° C.

TABLE 28

Production of NPI-0052, NPI-0047 and NPI-2065 by *Salinispora tropica* NPS021184 grown in production medium containing low sodium concentration (9.3 mM by ICP-MS analysis).

| | Titers (mg/L) | | | | | | | | | | |
|---|---|---|---|---|---|---|---|---|---|---|---|
| | Day 3 | | | Day 4 | | | Day 5 | | | Day 6 | | |
| Strain | Sal A | NPI-0047 | NPI-2065 | Sal A | NPI-0047 | NPI-2065 | Sal A | NPI-0047 | NPI-2065 | Sal A | NPI-0047 | NPI-2065 |
| 21184 | 97 | 0.14 | 0.79 | 191 | 0.86 | 3.0 | 180 | 0.48 | 2.8 | 201 | 0.62 | 3.4 |

TABLE 29

Production of Salinosporamide A, NPI-0047 and NPI-2065 by
Salinispora tropica NPS465 grown in production medium containing
low sodium concentration (93 mM by ICP-MS analysis).

| | Titers (mg/L) | | | | | | | | | | |
|---|---|---|---|---|---|---|---|---|---|---|---|
| | Day 4 | | | Day 5 | | | Day 6 | | | Day 7 | | |
| Strain | Sal A | NPI-0047 | NPI-2065 | Sal A | NPI-0047 | NPI-2065 | Sal A | NPI-0047 | NPI-2065 | Sal A | NPI-0047 | NPI-2065 |
| 465 | 118 | 3.7 | 0.73 | 128 | 3.5 | 0.90 | 130 | 3.8 | 0.89 | 124 | 3.3 | 0.77 |

TABLE 30

Production of Salinosporamide A, NPI-0047 and NPI-2065 by
Salinispora tropica NPS429 grown in production medium containing
low sodium concentration (9.3 mM by ICP-MS analysis).

| | Titers (mg/L) | | | | | | | | | | |
|---|---|---|---|---|---|---|---|---|---|---|---|
| | Day 4 | | | Day 5 | | | Day 6 | | | Day 7 | | |
| Strain | Sal A | NPI-0047 | NPI-2065 | Sal A | NPI-0047 | NPI-2065 | Sal A | NPI-0047 | NPI-2065 | Sal A | NPI-0047 | NPI-2065 |
| 429 | 109 | 1.8 | 0.35 | 126 | 2.7 | 0.74 | 158 | 2.9 | 1.3 | 156 | 2.9 | 1.3 |

We detected production of Salinosporamide A, NPI-0047 and NPI-2065 in all three *Salinispora tropica* strains grown in low sodium medium with NPS21184 showing the highest concentration of Salinosporamide A at 201 mg/L. The production of NPI-0047 was significantly lower in strain NPS21184 than the other two strains.

EXAMPLE 13

Growth of Low Sodium Frozen Stocks of *Salinispora tropica* CNB440, CNB476 and NPS21184 on Agar Medium Containing Low Concentration of Sodium (9.3 mM by ICP-MS Analysis)

Low Sodium Frozen Stocks of *Salinispora tropica* CNB440, CNB476 and NPS21184 prepared in Example 10 in low sodium medium containing 9.3 mM sodium (by ICP-MS analysis) were tested for growth on agar media also containing low sodium concentration (SHY.KCX, SHY.KCY and TCG.KCX). Agar plates containing high concentrations of sodium (saline fermentation condition, SHY.IO and TCG.B4C) and agar plates with low sodium (carbon and nitrogen sources provided in DI water; but with no salt supplement or $FeSO_4$ only—SHY.DI and TCG.DI media) were also included in this study for comparison purpose. After thawing the Low Sodium Frozen Stocks at room temperature, 30 μL each of the cultures were spread onto agar plates (60×15 mm, 10 mL agar medium) with the compositions listed in the table below.

| (Per liter of DI water) | | | | | | | |
|---|---|---|---|---|---|---|---|
| | SHY.IO | SHY.KCX | SHY.KCY | SHY.DI | TCG.B4C | TCG.KCX | TCG.DI |
| | 10 g Starch | 10 g Starch | 10 g Starch | 10 g Starch | 10 g Starch | 4 g Glucose | 4 g Glucose |
| | 4 g Hy Soy | 4 g Hy Soy | 4 g Hy Soy | 4 g Hy Soy | 4 g Hy Soy | 3 g Tryptone | 3 g Tryptone |
| | 4 g Yeast Extract | 4 g Yeast Extract | 4 g Yeast Extract | 4 g Yeast Extract | 4 g Yeast Extract | 5 g Casitone | 5 g Casitone |
| | 40 mg $Fe_2(SO_4)_3$ | 40 mg $Fe_2(SO_4)_3$ | 40 mg $Fe_2(SO_4)_3$ | 40 mg $Fe_2(SO_4)_3$ | 40 mg $Fe_2(SO_4)$ | 30 g KCl | 17 g Agar |
| | 30 g Instant Ocean | 30 g KCl | 30 g KCl | 17 g Agar | 24 g NaCl | 4.29 g $MgSO_4 \cdot 7H_2O$ | |
| | 17 g Agar | 4.29 g $MgSO_4 \cdot 7H_2O$ | 0.43 g $CaCl_2 \cdot 2H_2O$ | | 4.29 g $MgSO_4 \cdot 7H_2O$ | 0.43 g $CaCl_2 \cdot 2H_2O$ | |
| | | 0.43 g $CaCl_2 \cdot 2H_2O$ | 15.5 mg $SrCl_2$ | | 0.43 g $CaCl_2 \cdot 2H_2O$ | 15.5 mg $SrCl_2$ | |
| | | 15.5 mg $SrCl_2$ | 21.5 mg $H_3BO_3$ | | 15.5 mg $SrCl_2$ | 21.5 mg $H_3BO_3$ | |
| | | 21.5 mg $H_3BO_3$ | 2.6 mg NaF | | 21.5 mg $H_3BO_3$ | 2.6 mg NaF | |
| | | 2.6 mg NaF | 208 μg $CoCl_2 \cdot 6H_2O$ | | 2.6 mg NaF | 208 μg $CoCl_2 \cdot H_2O$ | |
| | | 208 μg $CoCl_2 \cdot 6H_2O$ | 17 g Agar | | 208 μg $CoCl_2 \cdot 6H_2O$ | 17 g Agar | |
| | | 17 g Agar | | | 17 g Agar | | |

The sodium content of the above agar media was determined by ICP-MS analysis:

TABLE 31

Sodium content determined by ICP-MS analysis (without the agar)

| | SHY.IO | SHY.KCX | SHY.DI | TCG.B4C | TCG.KCX | TCG.DI |
|---|---|---|---|---|---|---|
| [Na] | 452 mM | 10 mM | 7.6 mM | ND | 11 mM | 11 mM |

No ICP-MS analysis of SHY.KCY sample but the sodium content should be the same as SHY.KCX.
ND = Not Determined After inoculation, the edges of the agar plates were wrapped with parafilm to avoid evaporation and the plates were incubated at 28° C. for 4 weeks. The growth of *Salinispora tropica* CNB440, CNB476 and NPS21184 on the agar plates are summarized below:

TABLE 32

*Salinispora tropica* CNB440, 1st streak

| | SHY.IO | SHY.KCX | SHY.KCY | SHY.DI | TCG.B4C | TCG.KCX | TCG.DI |
|---|---|---|---|---|---|---|---|
| Wk 1 | + | − | − | − | + | −/+ | − |
| Wk 2 | ++ | −/+ | − | − | ++ | ++ | − |
| Wk 3 | +++ | −/+ | − | − | +++ | +++ | − |
| Wk 4 | +++ | + | −/+ | − | +++ | +++ | − |

Key: − no growth; −/+ poor growth; + fair growth; ++ good growth; +++ very good growth

TABLE 33

*Salinispora tropica* CNB476, 1st streak

| | SHY.IO | SHY.KCX | SHY.KCY | SHY.DI | TCG.B4C | TCG.KCX | TCG.DI |
|---|---|---|---|---|---|---|---|
| Wk 1 | ++ | −/+ | − | − | ++ | + | − |
| Wk 2 | +++ | −/+ | −/+ | − | +++ | +++ | − |
| Wk 3 | +++ | −/+ | −/+ | − | +++ | +++ | − |
| Wk 4 | +++ | + | −/+ | − | +++ | +++ | − |

Key: − no growth; −/+ poor growth; + fair growth; ++ good growth; +++ very good growth

TABLE 34

*Salinispora tropica* NPS21184, 1st streak

| | SHY.IO | SHY.KCX | SHY.KCY | SHY.DI | TCG.B4C | TCG.KCX | TCG.DI |
|---|---|---|---|---|---|---|---|
| Wk 1 | ++ | + | −/+ | − | ++ | + | − |
| Wk 2 | +++ | + | −/+ | − | +++ | ++ | − |
| Wk 3 | +++ | + | −/+ | − | +++ | +++ | − |
| Wk 4 | +++ | + | −/+ | − | +++ | +++ | − |

Key: − no growth; −/+ poor growth; + fair growth; ++ good growth; +++ very good growth Good growth was observed for all three strains growing on agar media containing high sodium (saline fermentation conditions with sodium concentration of 452 mM:: SHY.IO and TCG.B4C). No growth was observed for any strain on low sodium media (SHY.DI and TCG.DI). The sodium content in these media is very low, at 7.6 mM (SHY.DI) to 11 mM (TCG.DI) by ICP-MS analysis. We observed growth of all three *Salinispora tropica* strains on agar media containing low level of sodium but supplemented with 30 g/L KCl and other ions (SHY.KCX and TCG.KCX). The SHY.KCX and TCG.KCX media contain similar sodium content as the SHY.DI and TCG.DI, about 9 to 11 mM. This demonstrates the importance of adding KCl and other ions to the medium for supporting the growth of *Salinispora tropica*. The growth of all three *Salinispora tropica* strains on the TCG.KCX agar is significantly better than the SHY.KCX agar even though the sodium and other ion contents in these agar media are very similar. This also demonstrates the importance of the proper composition of agar medium in supporting the growth of *Salinispora tropica* strains. This observation is also substantiated by the observation of good growth of *Salinispora tropica* NPS021184 on A1.Kc4C agar medium in Example 7. A1 based agar medium is as good as TCG-based agar medium in supporting the growth of *Salinispora tropica* NPS21184 under low sodium condition. We also observed that the growth in SHY.KCX medium is better than the growth in the SHY.KCY medium without addition of magnesium. This indicated the importance of magnesium in supporting the growth of *Salinispora tropica*. We demonstrate here that *Salinispora tropica* can be grown in agar media containing low levels of sodium (10 to 11 mM) and supplemented with KCl and other ions (non-saline condition) shown in the table above.

To confirm the growth of *Salinispora tropica* strains in media containing low level of sodium (non-saline condition), two-week old agar cultures growing on SHY.KCX and TCG.KCX media were re-streaked onto the corresponding agar media by the sterile inoculation loops. The two-week old agar cultures growing on high sodium condition (SHY.IO and TCG.B4C) were also re-streaked onto the corresponding agar media for comparison purpose. After inoculation, the edges of the agar plates were wrapped with parafilm to avoid evaporation and the plates were incubated at 28° C. for 4 weeks. The growth of *Salinispora tropica* CNB440, CNB476 and NPS21184 on the agar cultures are summarized below:

TABLE 35

Salinispora tropica CNB440, 2$^{nd}$ streak

| | SHY.IO | SHY.KCX | TCG.KCX | TCG.B4C |
|---|---|---|---|---|
| Week 1 | +++ | −/+ | ++ | ++ |
| Week 2 | +++ | ++ | +++ | +++ |
| Week 3 | +++ | ++ | +++ | +++ |
| Week 4 | +++ | ++ | +++ | +++ |

Key:
− no growth;
−/+ poor growth;
+ fair growth;
++ good growth;
+++ very good growth

TABLE 36

Salinispora tropica CNB476, 2$^{nd}$ streak

| | SHY.IO | SHY.KCX | TCG.KCX | TCG.B4C |
|---|---|---|---|---|
| Week 1 | +++ | −/+ | ++ | ++ |
| Week 2 | +++ | −/+ | +++ | +++ |
| Week 3 | +++ | ++ | +++ | +++ |
| Week 4 | +++ | ++ | +++ | +++ |

Key:
− no growth;
−/+ poor growth;
+ fair growth;
++ good growth;
+++ very good growth

TABLE 37

Salinispora tropica NPS21184, 2$^{nd}$ streak

| | SHY.IO | SHY.KCX | TCG.KCY | TCG.B4C |
|---|---|---|---|---|
| Week 1 | +++ | + | ++ | ++ |
| Week 2 | +++ | ++ | +++ | +++ |
| Week 3 | +++ | ++ | +++ | +++ |
| Week 4 | +++ | ++ | +++ | +++ |

Key:
− no growth;
−/+ poor growth;
+ fair growth;
++ good growth;
+++ very good growth Good growth of all three *Salinispora tropica* strains was observed on TCG.KCX agar media after only one week of incubation. The growth rate of three *Salinispora tropica* strains on the low sodium (11 mM), non-saline TCG.KCX agar medium was similar to the high sodium (452 mM), saline agar media (SHY.IO and TCG.B4C) at the second streak. Growth of the *Salinispora tropica* strains was also observed in the other low sodium, non-saline SHY.KCX agar but the growth yield was not as good as the TCG.KCX agar medium.

EXAMPLE 14

Effect of Vitamin $B_{12}$ on Production of Salinosporamide A, NPI-0047 and NPI-2065 by *Salinispora tropica* NPS21184 in the INSTANT OCEAN® Commercial Salt Formulation Seed cultures were prepared by inoculating frozen stock of *Salinispora tropica* NPS021184 into four different seed media (Instant Ocean® based) with the following compositions (per liter of DI $H_2O$).

| Medium Components | 0x Vitamin $B_{12}$ | 1x Vitamin $B_{12}$ | 4x Vitamin $B_{12}$ | 10x Vitamin $B_{12}$ |
|---|---|---|---|---|
| Starch | 10 g | 10 g | 10 g | 10 g |
| Hy Soy | 4 g | 4 g | 4 g | 4 g |
| Yeast Extract | 4 g | 4 g | 4 g | 4 g |
| KBr | 100 mg | 100 mg | 100 mg | 100 mg |
| $Fe_2SO_4$ | 40 mg | 40 mg | 40 mg | 40 mg |
| $CaCO_3$ | 100 mg | 100 mg | 100 mg | 100 mg |
| INSTANT OCEAN® | 30 g | 30 g | 30 g | 30 g |
| Vitamin $B_{12}$ | 0 | 0.296 mg (0.22 μM) | 1.185 mg (0.88 μM) | 2.96 mg (2.2 μM) |

After incubating the above first seed cultures (10 ml medium in a 50-ml tube) for 72 hours at 250 rpm and 28° C., 5 mL of each first seed culture was inoculated into 100 mL of the second seed medium (in 500-mL Erlenmeyer flask) having the same composition as the first seed medium. The second seed cultures were incubated at 250 rpm and 28° C. for 48 hours. 5 mL of each of the second seed cultures was inoculated into 100 mL of the production medium (in 500 mL Erlenmeyer flask) containing the same composition as the seed medium. The 0x Vitamin $B_{12}$ second seed culture (no vitamin $B_{12}$ in seed medium) was also inoculated into additional production medium containing 0.296 mg/L Vitamin $B_{12}$ (1x vitamin $B_{12}$P).

About 24 hour after inoculation, sterile XAD-7 resin slurry was added to the production cultures in a final concentration of ~20 g/L. The production culture was then further incubated and harvested at various time points to determine productivity.

3.5 mL of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. freezer before HPLC analysis. The dried extract was resuspended in 320 μL DMSO and injected into HPLC using the TFS7 method for analysis.

The production of Salinosporamide A, NPI-0047 and NPI-2065 was monitored by Agilent HP1100 HPLC using an ACE C-18 reversed-phase column (4.6×150 mm), and an isocratic solvent system consisting of 67% water (0.01% TEA) and 33% acetonitrile (0.01% TFA). The flow rate was 1.5 mL/min for 15 min with the detector wavelength set at 210 nm and column temperature 35° C.

TABLE 38

Maximum production of Salinosporamide A, NPI-0047 and NPI-2065 by *Salinispora tropica* NPS21184 in production media (Instant Ocean ® based) supplemented with vitamin $B_{12}$

| Media conditions | [Vitamin $B_{12}$] in Seed Medium | [Vitamin $B_{12}$] in Production Medium | Maximum Titer (mg/L) | | |
|---|---|---|---|---|---|
| | | | Salinosporamide A | NPI-0047 | NPI-2065 |
| 0x Vitamin $B_{12}$ | 0 | 0 | 252 | 11.1 | 6.3 |
| 1x vitamin $B_{12}$P | 0 | 0.296 mg/L (0.22 µM) | 231 | 2.9 | 4.4 |
| 1x Vitamin $B_{12}$ | 0.296 mg/L (0.22 µM) | 0.296 mg/L (0.22 µM) | 266 | 2.8 | 4.9 |
| 4x Vitamin $B_{12}$ | 1.185 mg/L (0.88 µM) | 1.185 mg/L (0.88 µM) | 266 | 2.8 | 5.4 |
| 10x Vitamin $B_{12}$ | 2.96 mg/L (2.2 µM) | 2.96 mg/L (2.2 µM) | 247 | 2.5 | 4.9 |

Vitamin $B_{12}$, like cobalt, significantly reduced the concentration of NPI-0047 in the fermentation. Adding 0.22 mM of vitamin $B_{12}$ to the production medium (Instant Ocean®) based) effectively reduced the concentration of NPI-0047 by 74%. Including vitamin $B_{12}$ in the seed medium or increasing the vitamin $B_1$7 concentration in both seed and production media by 10 fold (2.2 µM) further reduced the concentration of NPI-0047 only slightly. Vitamin $B_{12}$ also reduced the concentration of NPI-2065 by 30% in the Instant Ocean® based medium.

EXAMPLE 15

Effect of Vitamin $B_{12}$ and Cobalt on Production of Salinosporamide A, NPI-0047 and NPI-2065 by *Salinispora tropica* NPS21184 in the Salt Formulation Based Medium Seed cultures were prepared by inoculating frozen stock of *Salinispora tropica* NPS021184 into three different seed media of varying salt content with the following compositions (per liter of DI $H_2O$).

| Medium Components | Control | 1xVitamin $B_{12}$ | 1x $CoCl_2•6H_2O$ |
|---|---|---|---|
| Starch | 10 g | 10 g | 10 g |
| Hy Soy | 4 g | 4 g | 4 g |
| Yeast Extract | 4 g | 4 g | 4 g |
| KBr | 100 mg | 100 mg | 100 mg |
| $Fe_2SO_4$ | 40 mg | 40 mg | 40 mg |
| $CaCO_3$ | 100 mg | 100 mg | 100 mg |
| Vitamin $B_{12}$ | 0 | 0.296 mg (0.22 µM) | 0 |
| $CoCl_2•6H_2O$ | 0 | 0 | 52 µg (0.22 µM) |

The seed medium was then supplemented with a chemically defined salt formulation. The chemically defined salt formulation was:

| Salt component | Per liter of DI $H_2O$ |
|---|---|
| NaCl | 24 g |
| KCl | 0.69 g |
| $MgSO_4•7H_2O$ | 4.29 g |
| $CaCl_2•2H_2O$ | 0.43 g |
| $SrCl_2$ | 15 5 mg |
| $H_3BO_3$ | 21.5 mg |
| NaF | 2.6 mg |

After incubating the above first seed cultures (10 ml medium in a 50-ml tube) for 72 hours at 250 rpm and 28° C., 5 mL of each first seed culture was inoculated into 100 mL of the second seed medium (in 500-mL Erlenmeyer flask) having the same composition as the first seed medium. The second seed cultures were incubated at 250 rpm and 28° C. for 48 hours. 5 mL of each of the second seed cultures was inoculated into 100 mL of the production medium (in 500 ml. Erlenmeyer flask) containing the same composition as the seed medium.

About 24 hour after inoculation, sterile XAD-7 resin slurry was added to the production cultures in a final concentration of ~20 g/L. The production culture was then further incubated and harvested at various time points to determine productivity.

Three and one-half (3.5) mL of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. freezer before HPLC analysis. The dried extract was resuspended in 320 µL DMSO and injected into HPLC using the 00TF14 method for analysis.

The production of Salinosporamide A, NPI-0047 and NPI-2065 was monitored by Agilent HP1100 HPLC using an ACE C-18 reversed-phase column (4.6×150 mm), and solvent system consisting of water (0.01% TFA) as solvent A and acetonitrile (0.01% TFA) as solvent B. The elution was started at 100% solvent A for 1 min, 100% solvent A to 35% solvent A gradient in 7 min, held at 35% solvent A for 11 min, 35% solvent A to 100% solvent B in 8 min and held at 100% solvent B for 9 min at a flow rate of 1.5 mL/min with the detector wavelength set at 210 nm and column temperature 35° C.

TABLE 39

Maximum production of Salinosporamide A, NPI-0047 and NPI-2065 by
Salinispora tropica NPS21184 in production media (defined salt formulation based)
supplemented with cobalt or vitamin $B_{12}$

| Media conditions | Seed Medium | Production Medium | Maximum Titer (mg/L) | | |
|---|---|---|---|---|---|
| | | | Salinosporamide A | NPI-0047 | NPI-2065 |
| Control | No vitamin $B_{12}$ or cobalt supplement | No vitamin $B_{12}$ or cobalt supplement | 277 | 4.7 | 5.6 |
| 1x vitamin $B_{12}$ | 0.296 mg/L (0.22 µM) Vitamin $B_{12}$ | 0.296 mg/L (0.22 µM) Vitamin $B_{12}$ | 304 | 1.1 | 7.2 |
| 1x $CoCl_2 \cdot 6H_2O$ | 52 µg/L (0.22 µM) $CoCl_2 \cdot 6H_2O$ | 52 µg/L (0.22 µM) $CoCl_2 \cdot 6H_2O$ | 297 | 1.4 | 6.6 |

Vitamin $B_{12}$ and $CoCl_2.6H_2O$, at equal concentration (0.22 µM), have the same effect in reducing the concentration of NPI-0047 by 70 to 77% in the salt formulation based medium. There is no reduction in concentration of NPI-2065 from Vitamin $B_{12}$ or $CoCl_2.6H_2O$ in the salt formulation based medium

EXAMPLE 16

Production of NPI-0052 in Low Chloride (19 Sodium Sulfate Based-Medium in Fermentor Culture Seed cultures were prepared by inoculating frozen stock of Salinispora tropica NPS021184 into seed medium consisting the following per liter of DI $H_2O$:

| 10 g | Starch |
|---|---|
| 4 g | Hy Soy |
| 4 g | Yeast Extract |
| 1 g | $CaCO_3$ |
| 100 mg | KBr |
| 40 mg | $Fe_2(SO_4)_3$ |

The seed medium was then supplemented with a chemically defined salt formulation. The chemically defined salt formulation included:

| Salt component | Per liter of DI $H_2O$ |
|---|---|
| $Na_2SO_4$ | 40 g |
| KCl | 0.69 g |
| $MgSO_4 \cdot 7H_2O$ | 4.29 g |
| $CaCl_2 \cdot 2H_2O$ | 0.43 g |
| $SrCl_2$ | 15 5 mg |
| $H_3BO_3$ | 21.5 mg |
| NaF | 2.6 mg |
| $CoCl_2 \cdot 6H_2O$ | 208 µg |

The first seed culture (100 mL medium) in a 500-mL Erlenmeyer flask was incubated at 250 rpm and 28° C. for 72 hours. 20 mL of the first seed culture was inoculated into second seed culture (400 ml medium) in a 2.8 L Fernbach flask with the same medium as the first seed culture. The second seed culture was incubated at 250 rpm and 28° C. for 48 hours. 200 mL of the third seed culture was inoculated into a B. Braun B-Plus 5 L fermentor containing 4 L third seed medium with the same composition as the first and second seed medium. The thirds seed fermentor culture was incubated at 300 rpm and 28° C. with the airflow rate of 2 L/min for 36 hours. 1.5 L of the third seed culture was inoculated into 26 L production medium in a 42 L B. Braun Biostat-C fermentor.

Per liter of DI $H_2O$, the production medium consisted of:

| 10 g | Starch |
|---|---|
| 4 g | Hy Soy |
| 4 g | Yeast Extract |
| 1 g | $CaCO_3$ |
| 100 mg | KBr |
| 40 mg | $Fe_2(SO_4)_3$ |

The production medium was then supplemented with a chemically defined salt formulation consisted of:

| Salt component | Per liter of DI $H_2O$ |
|---|---|
| $Na_2SO_4$ | 20 g |
| KCl | 0.69 g |
| $CaCl_2 \cdot 2H_2O$ | 0.43 g |
| $SrCl_2$ | 15 5 mg |
| $H_3BO_3$ | 21.5 mg |
| NaF | 2.6 mg |
| $CoCl_2 \cdot 6H_2O$ | 208 µg |

The ion content of the production medium was analyzed by ICP-MS analysis and found to have the following composition:

TABLE 40

| ICP-MS analysis of ions (mM) present in the medium | | | | | | | |
|---|---|---|---|---|---|---|---|
| [Na] | [Cl] | [K] | [Mg] | [Co] | [S] | [Ca] | [Fe] |
| 284 | 19 | 14 | 0.56 | $1.1 \times 10^{-3}$ | 159 | 3.8 | 0.16 |

The chloride content in the production medium is 19 mM, which is significantly lower than the chloride content in the INSTANT OCEAN® based medium (424 mM) and the defined salt formulation based medium (426 mM) (Table 20 of Example 9). The production fermentor culture was operated at 200 rpm and 28° C. with the airflow rate of 13 L/min. About 39 hours after inoculation, sterile XAD-7 resin slurry was added to the production culture in a final concentration of 20 g/L. The production culture was then further incubated and harvested at various time points to determine productivity.

3.5 of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. freezer before HPLC analysis. The dried extract was resuspended in 320 μL DMSO and injected into HPLC using the 00TF14 method for analysis.

The production of Salinosporamide A, NPI-0047 and NPI-2065 was monitored by Agilent HP1100 HPLC using an ACE C-18 reversed-phase column (4.6×150 mm), and solvent system consisting of water (0.01% TFA) as solvent A and acetonitrile (0.01% TFA) as solvent B. The elution was started at 100% solvent A for 1 min, 100% solvent A to 35% solvent A gradient in 7 min, held at 35% solvent A for 11 min, 35% solvent A to 100% solvent B in 8 min and held at 100% solvent B for 9 min at a flow rate of 1.5 mL/min with the detector wavelength set at 210 nm and column temperature 35° C.

TABLE 41

The production time course of NPI-0052, NPI-0047 and NPI-2065 in the low chloride medium by *Salinispora tropica* NPS21184 in the 42 L fermentor

| | Titers (mg/L) | | |
|---|---|---|---|
| Culture Age (hours) | Salinosporamide A | NPI-0047 | NPI-2065 |
| 74 | 77 | 3.7 | 2.4 |
| 83 | 85 | 3.6 | 2.6 |
| 98 | 164 | 7.7 | 4.6 |
| 106 | 198 | 12.1 | 5.2 |
| 123 | 225 | 15.5 | 6.1 |
| 130 | 229 | 15.6 | 6.4 |

Sodium sulfate effectively replaced sodium chloride in supporting the production of NPI-0052 in fermentor culture. The sulfate medium contains 19 mM chloride concentration that supported the production of 229 mg/L NPI-0052 in fermentor culture. The major chloride in the medium was derived from KCl, $CaCl_2$ and carried over from Hy Soy and Yeast Extract.

EXAMPLE 17

Comparison of Growth of Low Sodium Frozen Stocks of *Salinispora tropica* CNB440, CNB476 and NPS021184 Grown in Low Sodium Medium with Omission of NaF (No Discrete Sodium Salt Added)

Low Sodium Frozen Stocks of *Salinispora tropica* CNB440, CNB476 and NPS021184 prepared in Example 10 were used to inoculate 10 mL aliquots of the SHY.KCK seed medium in 50-mL culture tubes (25×150 mm)
SHY.KCK. (per liter of DI $H_2O$)
10 g Starch
4 g Hy Soy
4 g Yeast Extract
40 mg $Fe_2(SO_4)_3$
30 g KCl
4.29 g $MgSO_4.7H_2O$
0.43 g $CaCl_2.2H_2O$
15.5 mg $SrCl_2$
21.5 mg $H_3BO_3$
2.6 mg/L KF
208 μg $CoCl_2.6H_2O$ No discrete sodium salt was included in or added to Medium SHY.KCK, SHY.KCK differs from SHY.KCD in the omission of 2.6 mg/L NaF and 1 g/L $CaCO_3$ from SHY.KCD and the addition of 2.6 mg/L of KF in the medium. Therefore, Medium SHY.KCK contains no known addition of sodium salt. The sodium present in the medium is derived from other medium components. The ion content of Medium SHY.KCK was analyzed by ICP-MS analysis and found to have the following composition:

TABLE 42

ICP-MS analysis of ions (mM) present in the medium

| [Na] | [Cl] | [K] | [Mg] | [Co] | [S] | [Ca] | [Fe] |
|---|---|---|---|---|---|---|---|
| 10 | 482 | 407 | 1 24 | $1.2 \times 10^{-3}$ | 22 | 3.7 | 0.17 |

1 mL of the frozen stock each was used to inoculate 10 mL first seed SHY.KCK medium to yield an inoculum size of 10%. After incubating the above first seed cultures of CNB476 and NPS21184 for 48 hours at 250 rpm and 28° C., 5 mL of each culture was inoculated into 100 mL of the second seed medium (in 500-mL Erlenmeyer flask) having the same composition as the first seed medium. For CNB440, the first seed culture was grown for 5 days. 10 mL of the first seed culture was used to inoculate 100 mL of the second seed medium in a 500-mL Erlenmeyer flask. The dry cell weights of the first seed cultures at the time of inoculation to the second seed medium are shown in the following table:

TABLE 43

The dry cell weight of the first seed cultures of strains CNB440, CNB476 and NPS21184 grown in Medium SHY.KCK

| Strain | Culture age (hours) | Dry cell weight (mg/mL) |
|---|---|---|
| CNB440 | 120 | 1.9 |
| CN476 | 48 | 3.8 |
| NPS21184 | 48 | 4.5 |

Good cell growth of strains CNB476 and NPS21184 was observed after 48 hours incubation in the first seed culture in medium SHY.KCK. The growth rate and cell yield of strain. CNB440 are lower than strains CNB476 and NPS21184, yielding a dry cell weight of 1.9 mg/L after 120 hour incubation in first seed culture growing in Medium SHY-.KCK. The second seed cultures were incubated for 24 to 120 hours and yielded the following dry cell weight data:

TABLE 44

The dry cell weight of the first seed cultures of strains CNB440, CNB476 and NPS21184 grown in Medium SHY.KCK

| | Dry cell weight (mg/mL) | | | | |
|---|---|---|---|---|---|
| Strain | 24 hours | 48 hours | 72 hours | 96 hours | 120 hours |
| CNB440 | ND | 0.92 | 2.1 | 3.1 | 3.3 |
| CNB476 | 0.48 | 2.8 | 3.4 | 3.5 | 3.8 |
| NPS21184 | 0.97 | 2.4 | 3.1 | 3.3 | 3.8 |

ND = Not determined

The dry cell weight data from the second seed cultures confirmed the finding that the Low Sodium Frozen Stocks of CNB440, CNB476 and NPS21184 prepared in the low sodium medium (9.3 mM) can support good cell growth in low sodium Medium SHY.KCK which includes added trace metal ions other than sodium. The Low Sodium Frozen of strains CNB440, CNB476 and NPS21184 grew very well in the low sodium medium (10 mM sodium) with dry cell weights of 3.3 to 3.8 mg/mL. While the growth rate of CNB440 is slower in the low sodium medium, it achieved the same dry cell weight as NPS21184 after 96 hours incubation. Since Medium SHY.KCK contains 2.6 mg/L of KF or fluoride ion may play a role in supporting the growth of *Salinispora tropica* CNB440, CNB476 and NPS21184.

EXAMPLE 18

Growth of *Salinispora tropica* CNB440 and CNB476 and Production of Salinosporamide A in Non-Saline, Low Sodium Seed and Production Media Containing Trace Amount of Sodium Ion (Calculated Value: 0.06 mM; ICP-MS Analysis: 11 mM)

The first seed cultures were prepared by inoculating two frozen stocks each of *Salinispora tropica* CNB440 and CNB476 into first seed medium containing INSTANT OCEAN® commercial salt formulation to obtain good growth of the culture. The first seed culture was centrifuged and washed with Wash Media containing no addition of sodium salt to remove the sodium ion present in the first seed culture prior to inoculation into the second seed stage containing medium with only trace amounts of sodium ion (calculated value of sodium derived from 2.6 mg/L NO: 0.06 mM, while no ICP-MS analysis was performed, it is estimated that the sodium content is ~5.7 mM based on ICP-MS analysis of a similar medium A1.Ks4C, Table 14A of Example 7). The third seed culture was then inoculated into the production medium SHY.KcMC containing trace amount of sodium ion (calculated value of sodium derived from 2.6 mg/L NaF: 0.06 mM; ICP-MS analysis: 11 mM, Table 15 of Example 8). This process significantly reduced the carried over of sodium ion from the seed cultures to the production culture.

The first seed medium consisted of glucose, Hy Soy, and yeast extract at concentrations of 8 g/L, 6 g/L, and 6 g/L, respectively. The seed medium was then supplemented with 30 g/L INSTANT OCEAN® commercial salt formulation.

The first seed culture (100 ml medium containing ~424 mM sodium ion from Instant Ocean) in a 500-mL Erlenmeyer flask was incubated at 28° C. and 250 rpm for 72 hours. 10 mL of the first seed culture was transferred to a sterile 15-mL centrifuge tube and centrifuged at 3,000 rpm for 15 min. The packed cell volume observed was 5% for both strain 429 and strain 465. The supernatant was decanted and 10 mL of Wash Medium (10 g/L starch, 2 g/L peptone, 4 g/L yeast extract, and 30 g/L KCl in D.I. water) was added to the centrifuge tube. The centrifuge tube was mixed and then centrifuged at 3000 rpm for 15 min. The supernatant was decanted and the cell culture was washed again by re-suspending in Wash Media and centrifuging and decanting as before. Then 10 mL of the second seed medium (containing 0.06 mM sodium ion from NaF) was added to the centrifuge tube. The second seed medium consisted of starch (USB, catalog #21695), peptone (USB, catalog #20048), and yeast extract (USB, catalog #23547) at concentrations of 10 g/L, 2 g/L, and 4 g/L, respectively. The seed medium was also supplemented with a chemically defined salt formulation. This supplemented medium is referred to as A1Kc4C. The chemically defined salt formulation consisted of:

| Salt component | Per liter of DI H$_2$O |
|---|---|
| KCl | 30 g |
| MgSO$_4$•7H$_2$O | 4.29 g |
| KBr | 85.9 mg |

-continued

| Salt component | Per liter of DI H$_2$O |
|---|---|
| CaCO$_3$ | 0.43 g |
| CaCl$_2$•2H$_2$O | 0.43 g |
| SrCl$_2$ | 15 5 mg |
| H$_3$BO$_3$ | 21.5 mg |
| NaF | 2.6 mg |
| CoCl$_2$•6H$_2$O | 208 µg |

The centrifuge tube was gently vortexed to mix the cell suspension and 5 mL of the washed cells were inoculated to the second seed culture containing 100 ml medium having the same composition as the second seed medium in a 500-mL Erlenmeyer flask. The sodium concentration in the washed cell inoculum had been reduced down to a calculated level of ~0.11 mM sodium based on 5% packed cell volume, which is double the amount of sodium content in the second seed medium (0.06 mM from 2.6 mg/L. NaF). The second seed culture was incubated for 6 days before inoculating 5 mL of the second seed culture into the third seed culture containing the same medium as the second seed stage. With further dilution of the second seed inoculum by the medium of the third seed stage, the sodium content in the third seed culture is essentially calculated as ~0.06 mM (contributed by 2.6 mg/L NaF). The third seed cultures of CNB440 and CNB476 were incubated for 5 days and 3 days, respectively, before inoculating 5 ml of the third seed culture into the production medium (100 ml in a 500-ml Erlenmeyer flask) with the same composition of the defined salt supplemented-production medium, SHY.KcMC, in Example 5.

Per liter of DI H$_2$O the production medium. SHY.KcMC consisted of 10 g Starch 4 g Hy Soy 4 g Yeast Extract 1 g CaCO$_3$ 1.00 mg KBr The production medium was then supplemented with a chemically defined salt formulation. The chemically defined salt formulation consisted of:

| Salt component | Per liter of DI H$_2$O |
|---|---|
| KCl | 30 g |
| CaCl$_2$•2H$_2$O | 0.43 g |
| SrCl$_2$ | 15.5 mg |
| H$_3$BO$_3$ | 21.5 mg |
| NaF | 2.6 mg |
| CoCl$_2$•6H$_2$O | 52 µg |

About 24 after inoculation, sterile XAD-7 resin slurry was added to the production cultures in a final concentration of 20 g/L. The production culture was then further incubated and harvested at various time points to determine productivity 3.5 mL of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. freezer before HPLC analysis. The dried extract was resuspended in 320 µL DMSO and injected into HPLC using the TFS7 method for analysis.

The production of Salinosporamide A, NPI-0047 and NPI-2065 was monitored by Agilent HP1100 HPLC using an ACE C-18 reversed-phase column (4.6×150 mm), and an isocratic solvent system consisting of 67% water (0.01% TFA) and 33% acetonitrile (0.01% TFA). The flow rate was 1.5 mL/min for 15 min with the detector wavelength set at 210 nm and column temperature 35° C.

TABLE 45

Production of Salinosporamide A, NPI-0047 and NPI-2065 by *Salinispora tropica* CNB440 grown in production medium containing 0.06 mM sodium ion based on NaF present in medium and 11 mM sodium ion based on ICP-MS analysis.

| Culture Age (days) | Titer (mg/L) | | |
|---|---|---|---|
| | Salinosporamide A | NPI-0047 | NPI-2065 |
| 3 | 0 | 0 | 0 |
| 4 | 0 | 0 | 0 |
| 5 | 28 | 0.4 | 0.3 |
| 6 | 67 | 0.6 | 0.6 |

TABLE 46

Production of Salinosporamide A, NPI-0047 and NPI-2065 by *Salinispora tropica* CNB476 grown in production medium containing 0.06 mM sodium ion based on NaF present in medium and 11 mM sodium ion based on ICP-MS analysis.

| Culture Age (days) | Titers (mg/L) | | |
|---|---|---|---|
| | Salinosporamide A | NPI-0047 | NPI-2065 |
| 3 | 0 | 0 | 0 |
| 4 | 64 | 0.2 | 1.0 |
| 5 | 107 | 0.8 | 0.3 |
| 6 | 147 | 0.1 | 1.0 |

*Salinispora tropica* CNB440 and CNB476 can be grown in production medium with a low sodium ion concentration of 11 mM, which is about 2% of the sodium content in sea water (487 mM sodium, see Table 20 of Example 9). In this low sodium production medium, *Salinispora tropica* CNB440 and *Salinispora tropica* CNB476 produced 67 mg/L and 147 mg/L of Salinosporamide A, respectively. Since *Salinispora tropica* CNB440 and *Salinispora tropica* CNB476 can be grown in the A1.Kc4C seed media with sodium content estimated at 5.7 mM by ICP-MS analysis, this demonstrated that *Salinispora tropica* CNB440 and *Salinispora tropica* CNB476 can be grown in medium with sodium content at least as low as 1% of seawater.

EXAMPLE 19

Growth of *Salinispora tropica* CNB440 and CNB476 in Agar Media Containing (a) Low Sodium and (b) Low Sodium and Low Chloride The first seed culture was prepared by inoculating two frozen stocks each of *Salinispora tropica* CNB440 and CNB476 into first seed medium consisted of glucose, Soy, and yeast extract at concentrations of 8 g/L, 6 g/L, and 6 g/L, respectively. The seed medium was then supplemented with 30 g/L INSTANT OCEAN® commercial salt formulation.

The first seed culture (100 mL medium containing ~424 mM sodium ion from INSTANT OCEAN®) in a 500-mL Erlenmeyer flask was incubated at 28° C. and 250 rpm for 72 hours. 1.5 mL of the first seed culture each was transferred to two sterile 15-mL centrifuge tubes and centrifuged at 3,000 rpm for 15 min. The supernatant from each tube was decanted. 10 mL of Wash Medium A was added to one tube while 10 mL of Wash Medium B was added to the other tube. Both wash media consisted of 10 g/L starch, 2 g/L peptone, 4 g/L yeast extract and either 30 g/L KCl (Wash Media A) or 48 g/L $K_2SO_4$ (Wash Media B). The centrifuge tubes were mixed and then centrifuged at 3000 rpm for 15 min. The supernatant was decanted and the cells were resuspended in the same medium and centrifuged again. After the final centrifuging, a pipette was used to remove most of the supernatant and allow enough remaining medium to yield a 2 ml cell suspension in the tube. These cell suspensions were used as the inoculum for the agar cultures. Four agar media were used and all consisted of starch, peptone, yeast extract, and agar (Difco, catalog #214530) at concentrations of 10 g/L, 2 g/L, 4 g/L and 17 g/L, respectively, plus a salt supplement. Agar Medium A used the following chemically defined salt supplement. This supplemented medium is referred to as A1.Kc4C

| Agar Medium A - Salt Supplement | |
|---|---|
| Salt component | Per liter of DI $H_2O$ |
| KCl | 30 g |
| $MgSO_4 \cdot 7H_2O$ | 4.29 g |
| KBr | 85.9 mg |
| $CaCO_3$ | 0.43 g |
| $CaCl_2 \cdot 2H_2O$ | 429.3 mg |
| $SrCl_2$ | 15 5 mg |
| $H_3BO_3$ | 21.5 mg |
| NaF | 2.6 mg |
| $CoCl_2 \cdot 6H_2O$ | 208 μg |

In order to test the significance of the ion supplements other than potassium, Agar Medium A-1 used only 30 g/L KCl as the salt supplement. That is, to examine if simple replacement of NaCl by KCl in the agar medium can support the growth of *Salinispora tropica* CNB440 and CNB476.

The Agar Medium B used the following chemically defined salt supplement. This supplemented medium is referred to as A1.Ks4C.

| Agar Medium B - Salt Supplement | |
|---|---|
| Salt component | Per liter of DI $H_2O$ |
| $K_2SO_4$ | 48 g |
| $MgSO_4 \cdot 7H_2O$ | 4.29 g |
| KBr | 85.9 mg |
| $CaCO_3$ | 0.43 g |
| $CaCl_2 \cdot 2H_2O$ | 429.3 mg |
| $SrCl_2$ | 15 5 mg |
| $H_3BO_3$ | 21.5 mg |
| NaF | 2.6 mg |
| $CoCl_2 \cdot 6H_2O$ | 208 μg |

In order to test the significance of the ion supplements other than potassium, Agar Medium B-1 used only 48 g/L $K_2SO_4$ as its supplement. That is, to examine if simple replacement of NaCl by $K_2SO_4$ in the agar medium can support the growth of *Salinispora tropica* CNB440 and CNB476. Particular ion concentration of Agar Medium B with the complete salt supplements (Medium A1.Ks4C) were determined by ICP-MS (Table 14A, Example 7).

Sterile inoculation loops were used to transfer cells from Wash Medium A to agar plates containing 20 mL of Agar Medium A (calculated sodium content: 0.06 mM; calculated chloride content: 415 mM) and 20 mL of Agar Medium A-1

(calculated sodium content: 0.06 mM; calculated chloride content: 403 mM), Sterile inoculation loops were used to transfer cells from Wash Medium B to agar plates containing 20 mL of Agar. Medium B (calculated sodium content: 0.06 mM; calculated chloride content: 12 mM; ICP-MS analysis: sodium content: 5.7 mM; chloride content: 14 mM) and 20 mL of Agar Medium B-1 (calculated sodium content: 0.06 mM; calculated chloride content: ~0). After inoculation, the edges of the agar plates were wrapped with parafilm to avoid evaporation. The agar plates were incubated at 28° C. for 2-4 weeks to observe good growth. No growth was observed in Agar Medium A-1 or Agar Medium B-1 after 4 weeks incubation. Good growth was observed in Agar Medium A and Medium B after two weeks of incubation. After two weeks of incubation, the growth from Agar Medium A and Agar Medium B were transferred to fresh Agar Medium A and Agar Medium B plates, respectively. The re-streaked agar plates were again incubated at 28° C. to observe growth. The observation of growth of *Salinispora tropica* CNB440 and *Salinispora tropica* CNB476 on these re-streaked agar plates were summarized in the following tables.

TABLE 47

Observation of growth of *Salinispora tropica* CNB440 grown on agar medium A1.Kc4C and A1.Ks4c (second streaked)

| Agar Medium | Week 1 | Week 2 | Week 3 | Week 4 |
|---|---|---|---|---|
| A (A1.Kc4C) | ++ | ++ | +++ | +++ |
| B (A1.Ks4C) | +++ | +++ | +++ | +++ |

Key:
− no growth;
−/+ poor growth;
+ fair growth;
++ growth;
+++ very good growth

TABLE 48

Observation of growth of *Salinispora tropica* CNB476 grown on agar medium A1.Kc4C and A1.Ks4C (second streaked)

| Agar Medium | Week 1 | Week 2 | Week 3 | Week 4 |
|---|---|---|---|---|
| A (A1.Kc4C) | +++ | +++ | +++ | +++ |
| B (A1.Ks4C) | ++ | ++ | +++ | +++ |

Key:
− no growth;
−/+ poor growth;
+ fair growth;
++ growth;
+++ very good growth Both *Salinispora tropica* strains CNB440 and CNB476 can be grown in agar media containing either low sodium (5.7 mM) and low chloride (14 mM), providing that the agar media is also supplemented with other ions such as $MgSO_4$, KBr, $CaCO_3$, $CaCl_2$, $SrCl_2$, $H_3BO_3$, NaF and $CoCl_2$. Substitution of KCl or $K_2SO_4$ for NaCl alone cannot support the growth of *Salinispora tropica* strains NFS429 and NFS465 in agar media.

EXAMPLE 20

The Effect of Sodium Chloride in the Production Medium on the Production of Salinosporamide A, NPI-0047 and NPI-2065 by *Salinispora tropica* CNB440, CNB476 and NPS21184

Seed cultures were prepared by inoculating frozen stocks of *Salinispora tropica* CNB440, CNB476 and NPS21184 into seed medium.

The seed medium consisted of glucose, Hy Soy, and yeast extract at concentrations of 8 g/L, 6 g/L, and 6 g/L, respectively. The seed medium was then supplemented with a chemically defined salt formulation consisted of:

| Salt component | Per liter of DI $H_2O$ |
|---|---|
| NaCl | 24 g |
| KCl | 0.69 g |
| $MgSO_4 \cdot 7H_2O$ | 4.29 g |
| KBr | 85.9 mg |
| $CaCO_3$ | 0.43 g |
| $CaCl_2 \cdot 2H_2O$ | 0.43 g |
| $SrCl_2$ | 15 5 mg |
| $H_3BO_3$ | 21.5 mg |
| NaF | 2.6 mg |
| $CoCl_2 \cdot 6H_2O$ | 208 µg |

The first seed cultures (100 mL medium) in 500-mL Erlenmeyer flasks were incubated for 96 hours before inoculating 5 mL of the first seed culture into the second seed medium with the same composition as the first seed medium. The second seed cultures (100 mL medium in 500-mL Erlenmeyer flask) were incubated for 48 hours before inoculating 5 mL of the second seed culture into the production medium (100 mL in a 500-mL Erlenmeyer flask).

Per liter of DI 1-120, the production medium consisted of:10 g Starch, 4 g Hy Soy, 4 g Yeast Extract, 1 g $CaCO_3$, 40 mg $Fe_2(SO_4)_3$, and 100 mg KBr. The production medium was then supplemented with a chemically defined salt formulation consisted of the following common salt components along with different levels of NaCl:

| Salt component | Per liter of DI $H_2O$ |
|---|---|
| KCl | 0.69 g |
| $CaCl_2 \cdot 2H_2O$ | 0.43 g |
| $SrCl_2$ | 15 5 mg |
| $H_3BO_3$ | 21.5 mg |
| NaF | 2.6 mg |
| $CoCl_2 \cdot 6H_2O$ | 52 µg |

The NaCl levels used were 0, 5, 10, 15, 20, 24 and 30 g/L. About 24 after inoculation, sterile XAD-7 resin slurry was added to the production cultures in a final concentration of 20 g/L. The production culture was then further incubated and harvested at various time points to determine productivity.

Three and one-half (3.5) mL of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. freezer before HPLC analysis. The dried extract was resuspended in 320 µL DMSO and injected into HPLC using the TFS7 method for analysis.

The production of Salinosporamide A, NPI-0047 and NPI-2065 was monitored by Agilent HP1100 HPLC using an ACE C-18 reversed-phase column (4.6×150 mm), and an isocratic solvent system consisting of 67% water (0.01% TFA) and 33% acetonitrile (0.01% TFA). The flow rate was 1.5 mL/min with the detector wavelength set at 210 nm and column temperature 35° C.

TABLE 49

Production of Salinosporamide A by *Salinispora tropica* CNB440, CNB476, and NPS021184 grown in production medium containing salt formulation with different concentrations of NaCl.

| NaCl Concentration (g/L) | Titer (mg/L) | | |
|---|---|---|---|
| | CNB440 | CNB476 | NPS21184 |
| 0 | 0 | 0 | 0 |
| 5 | 19 | 0 | 5.4 |
| 10 | 55 | 72 | 235 |
| 15 | 63 | 96 | 288 |
| 20 | 83 | 111 | 286 |
| 24 | 84 | 116 | 295 |
| 30 | 97 | 115 | 223 |

TABLE 50

Production of NPI-0047 by *Salinispora tropica* CNB440, CNB476, and NPS021184 grown in production medium containing salt formulation with different concentrations of NaCl.

| NaCl Concentration (g/L) | Titer (mg/L) | | |
|---|---|---|---|
| | CNB440 | CNB476 | NPS21184 |
| 0 | 0 | 0 | 0 |
| 5 | 0.8 | 0 | 0.5 |
| 10 | 4.6 | 4.9 | 14 |
| 15 | 4.5 | 5.4 | 6.4 |
| 20 | 5.2 | 3.2 | 1.2 |
| 24 | 4.8 | 2.9 | 2.1 |
| 30 | 3.2 | 1.3 | 1.4 |

TABLE 51

Production of NPI-2065 by *Salinispora tropica* CNB440, CNB476, and NPS021184 grown in production medium containing salt formulation with different concentrations of NaCl.

| NaCl Concentration (g/L) | Titer (mg/L) | | |
|---|---|---|---|
| | CNB440 | CNB476 | NPS21184 |
| 0 | 0 | 0 | 0 |
| 5 | 0.4 | 0 | 0 |
| 10 | 0.9 | 1.0 | 3.9 |
| 15 | 0.9 | 0.5 | 6.2 |
| 20 | 0.4 | 1.1 | 6.2 |
| 24 | 0.5 | 1.1 | 6.2 |
| 30 | 0.6 | 1.1 | 4.2 |

The growth yield of the day 6 production cultures of *Salinispora tropica* CNB440, CNB476, and NPS021184 grown in production medium containing salt formulation with different concentrations of NaCl was determined by packed cell volume and is shown the following table.

TABLE 52

The growth yield of the day 6 production cultures of *Salinispora tropica* CNB440, CNB476, and NPS021184 grown in production medium containing salt formulation with different concentrations of NaCl.

| NaCl Concentration (g/L) | Packed Cell Volume (%) | | |
|---|---|---|---|
| | CNB440 | CNB476 | NPS21184 |
| 0 | 0 | 0 | 0 |
| 5 | 5 | 2 | 6 |
| 10 | 5 | 5 | 6 |
| 15 | 4 | 5 | 6 |
| 20 | 5 | 6 | 5 |
| 24 | 5 | 6 | 5 |
| 30 | 5 | 6 | 5 |

No growth was observed for any of the three strains when the above production medium was not supplemented with NaCl. Both *Salinispora tropica* CNB440 and NPS21184 achieved good cell yield when the above production medium was supplemented with 5 g/L NaCl. There was no difference in the cell yield with further increase in the concentration of NaCl from 10 g/L to 30 g/L. *Salinispora tropica* CNB476 required higher concentration of NaCl, 10 g/L, for achieving good growth yield.

The production of NPI-0052 was detected, at low concentration, in both *Salinispora tropica* CNB440 (19 mg/L) and NPS21184 (5.4 mg/L) in the medium supplemented with 5 g/L NaCl. No NPI-0052 was detected in *Salinispora tropica* CNB476 grown in 5 g/L NaCl and this may be related to the poor cell yield. *Salinispora tropica* NPS21184 is clearly the best NPI-0052-producer among the three strains with the maximum titer of 295 mg/L detected at 24 g/L NaCl while *Salinispora tropica* CNB440 and CNB476 had maximum titers of 97 mg/L and 116 mg/L, respectively.

For the production of NPI-0074, there is a trend of decreasing concentration of NPI-0047 with increasing concentration of NaCl in the production medium. The production of NPI-0047 is the lowest in *Salinispora tropica* NPS21184, among the three strains tested. The production of NPI-2065 is the highest in *Salinispora tropica* NPS21184, among the three strains tested.

EXAMPLE 21

Compare the Effect of Cobalt on the Production of Salinosporamide A, NPI-0047 and NPI-2065 by *Salinispora tropica* CNB440, CNB476 and NPS21184

Seed cultures were prepared by inoculating frozen stocks of *Salinispora tropica* CNB440, CNB476 and NPS21184 into two different seed media.

Both seed media consisted of glucose, Hy Soy, and yeast extract at concentrations of 8 g/L, 6 g/L, and 6 g/L, respectively. The seed media were then supplemented with a chemically defined salt formulation consisting of:

| Salt component | Per liter of DI $H_2O$ |
|---|---|
| NaCl | 24 g |
| KCl | 0.69 g |
| $MgSO_4 \cdot 7H_2O$ | 4.29 g |
| KBr | 85.9 mg |
| $CaCO_3$ | 0.43 g |
| $CaCl_2 \cdot 2H_2O$ | 0.43 g |
| $SrCl_2$ | 15 5 mg |
| $H_3BO_3$ | 21.5 mg |
| NaF | 2.6 mg |

One seed medium was further supplemented with 208 µg/L $CoCl_2 \cdot 6H_2O$. The first seed cultures (100 mL medium) in 500-mL Erlenmeyer flasks were incubated for 72 hours before inoculating 5 mL of the first seed culture into the second seed medium with the same composition as the first seed medium. The second seed cultures (100 mL medium in 500-mL Erlenmeyer flask) were incubated for 48 hours before inoculating 5 mL of the second seed culture into the production media (100 mL in a 500-mL Erlenmeyer flask) containing the following common ingredient, per liter of DI $H_2O$: 10 g Starch, 4 g Hy Soy, 4 g Yeast Extract, 1 g $CaCO_3$, 40 mg $Fe_2(SO_4)_3$, and 100 mg KBr. The production media was then supplemented with a chemically defined salt formulation consisting of the following common salt components:

| Salt component | Per liter of DI $H_2O$ |
| --- | --- |
| NaCl | 24 g/L |
| KCl | 0.69 g |
| $CaCl_2 \cdot 2H_2O$ | 0.43 g |
| $SrCl_2$ | 15 5 mg |
| $H_3BO_3$ | 21.5 mg |
| NaF | 2.6 mg |

One production medium was also supplemented with 52 μg/L $CoCl_2.6H_2O$. The seed culture with no cobalt was inoculated into the production medium with no added cobalt. The seed culture containing 208 μg/L $CaCl_2.6H_2O$ was inoculated into production medium with 52 μg/L $CoCl_2.6H_2O$. After about 24 hour incubation into the production culture, sterile XAD-7 resin slurry was added to the production cultures in a final concentration of 20 g/L. The production culture was then further incubated and harvested at various time points to determine productivity.

Three and one-half (3.5) mL of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. freezer before HPLC analysis. The dried extract was resuspended in 320 μL DMSO and injected into HPLC using the TFS7 method for analysis.

The production of Salinosporamide A, NPI-0047 and NPI-2065 was monitored by Agilent HP1100 HPLC using an ACE C-18 reversed-phase column (4.6×150 mm), and an isocratic solvent system consisting of 67% water (0.01% TFA) and 33% acetonitrile (0.01% TFA). The flow rate was 1.5 mL/min with the detector wavelength set at 210 nm and column temperature 35° C.

TABLE 53

Production of Salinosporamide A by *Salinispora tropica* CNB440, CNB476, and NPS021184 grown in seed and production medium containing different concentrations of cobalt.

| [$CoCl_2 \cdot 6H_2O$] in seed medium | [$CoCl_2 \cdot 6H_2O$] in production medium | Titer (mg/L) | | |
| --- | --- | --- | --- | --- |
| | | CNB440 | CNB476 | NPS21184 |
| 0 | 0 | 100 | 111 | 258 |
| 208 μg/L | 52 μg/L | 84 | 111 | 292 |

TABLE 54

Production of NPI-0047 by *Salinispora tropica* CNB440, CNB476, and NPS021184 grown in seed and production medium containing different concentrations of cobalt.

| [$CoCl_2 \cdot 6H_2O$] in seed medium | [$CoCl_2 \cdot 6H_2O$] in production medium | Titer (mg/L) | | |
| --- | --- | --- | --- | --- |
| | | CNB440 | CNB476 | NPS21184 |
| 0 | 0 | 13 | 17 | 13 |
| 208 μg/L | 52 μg/L | 6.8 | 8.1 | 1.2 |

TABLE 55

Production of NPI-2065 by *Salinispora tropica* CNB440, CNB476, and NPS021184 grown in seed and production medium containing different concentrations of cobalt.

| [$CoCl_2 \cdot 6H_2O$] in seed medium | [$CoCl_2 \cdot 6H_2O$] in production medium | Titer (mg/L) | | |
| --- | --- | --- | --- | --- |
| | | CNB440 | CNB476 | NPS21184 |
| 0 | 0 | 0.78 | 1.3 | 6.5 |
| 208 μg/L | 52 μg/L | 0.69 | 0.88 | 5.4 |

This example supports the theory that the addition of cobalt to the seed and production media reduced the production of NPI-0047 in all three *Salinispora tropica* strains. However, the three *Salinispora tropica* strains have different degree of reduction of NPI-0047 by cobalt. *Salinispora tropica* NPS21184 shows the highest percentage (91%) of reduction of NPI-0047 by cobalt. Cobalt reduced the production of NPI-0047 by *Salinispora tropica* CNB440 and CNB476 by 48% and 52%, respectively.

EXAMPLE 22

Examination of the Effect of Cobalt in INSTANT OCEAN® Commercial Salt Formulation-Based Seed and Production Media on the Production of Salinosporamide A, NPI-0047 and NPI-0065 b *Salinispora tropica* NPS21184

Seed cultures were prepared by inoculating frozen stocks of *Salinispora tropica* NPS21184 into seed medium. The seed medium consisted of glucose, Hy Soy, yeast extract and INSTANT OCEAN® at concentrations of 8 g/L, 6 g/L, 6 g/L, and 30 g/L, respectively. The seed media were supplemented with 0, 52 μg/L or 208 μg/L of $CoCl_2.6H_2O$. The first seed cultures (100 mL medium in 500-mL Erlenmeyer flask) were incubated for 3 days before inoculating into the second seed media with the same composition of the first media. The second seed cultures (100 mL medium in 500-mL Erlenmeyer flask) were incubated for 2 days before inoculating into the production media (100 mL in 500-mL Erlenmeyer flask).

Per liter of DI $H_2O$, the production media consisted of: 10 g Starch, 4 g Hy Soy, 4 g Yeast Extract, 1 g $CaCO_3$, 40 mg $Fe_2(SO_4)_3$, 100 mg KBr, and 30 g INSTANT OCEAN® The production media were supplemented with 0, 13 μg/L, 52 μg/L or 208 μg/L of $CoCl_2.6H_2O$. The following table summarizes the conditions used for this study

| Condition | Seed medium | Production medium |
| --- | --- | --- |
| 1 (Control) | No cobalt addition | No cobalt addition |
| 2 | No cobalt addition | +13 μg/L $CoCl_2 \cdot 6H_2O$ |
| 3 | No cobalt addition | +52 μg/L $CoCl_2 \cdot 6H_2O$ |

-continued

| Condition | Seed medium | Production medium |
|---|---|---|
| 4 | No cobalt addition | +208 µg/L CoCl$_2$•6H$_2$O |
| 5 | +52 µg/L CoCl$_2$•6H$_2$O | No cobalt addition |
| 6 | +52 µg/L CoCl$_2$•6H$_2$O | +13 µg/L CoCl$_2$•6H$_2$O |
| 7 | +52 µg/L CoCl$_2$•6H$_2$O | +52 µg/L CoCl$_2$•6H$_2$O |
| 8 | +52 µg/L CoCl$_2$•6H$_2$O | +208 µg/L CoCl$_2$•6H$_2$O |
| 9 | +208 µg/L CoCl$_2$•6H$_2$O | No cobalt addition |
| 10 | +208 µg/L CoCl$_2$•6H$_2$O | +13 µg/L CoCl$_2$•6H$_2$O |

-continued

| Condition | Seed medium | Production medium |
|---|---|---|
| 11 | +208 µg/L CoCl$_2$•6H$_2$O | +52 µg/L CoCl$_2$•6H$_2$O |
| 12 | +208 µg/L CoCl$_2$•6H$_2$O | +208 µg/L CoCl$_2$•6H$_2$O |

After 24 hours of inoculation into the production media, sterile XAD-7 resin slurry was added to the production cultures in a final concentration of 20 g/L. The production cultures were then further incubated and harvested at various time points to determine productivity.

3.5 mL of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. freezer before HPLC analysis. The dried extract was resuspended in 320 µL DMSO and injected into HPLC using the 00TF14 method for analysis.

The production of Salinosporamide A, NPI-0047 and NPI-2065 was monitored by Agilent HP1100 HPLC using an ACE C-18 reversed-phase column (4.6×150 mm), and solvent system consisting of water (0.01% TFA) as solvent A and acetonitrile (0.01% TFA) as solvent B. The elution was started at 100% solvent A for 1 min, 100% solvent A to 35% solvent A gradient in 7 min, held at 35% solvent A for 11 min, 35% solvent A to 100% solvent B in 8 min and held at 100% solvent B for 9 min at a flow rate of 1.5 mL/min with the detector wavelength set at 210 nm and column temperature 35° C.

The highest Salinosporamide A titer was detected at day 4 of the production cycle. The titers of Salinosporamide A, NPI-0047 and NPI-2065 at day 4 of the production cycle are summarized in the following table.

TABLE 56

Production of Salinosporamide A, NPI-0047 and NPI-2065 in INSTANT OCEAN ®-based seed and production media supplemented with various concentrations of cobalt

| Conditions | Seed medium | Production medium | Titers (mg/L) | | |
|---|---|---|---|---|---|
| | | | Salinosporamide A | NPI-0047 | NPI-2065 |
| 1 (Control) | No cobalt addition | No cobalt addition | 275 | 15 | 7.3 |
| 2 | No cobalt addition | +13 µg/L CoCl$_2$•6H$_2$O | 275 | 7.4 | 6.9 |
| 3 | No cobalt addition | +52 µg/L CoCl$_2$•6H$_2$O | 244 | 5.6 | 5.7 |
| 4 | No cobalt addition | +208 µg/L CoCl$_2$•6H$_2$O | 244 | 5.5 | 6.0 |
| 5 | +52 µg/L CoCl$_2$•6H$_2$O | No cobalt addition | 281 | 11.8 | 6.2 |
| 6 | +52 µg/L CoCl$_2$•6H$_2$O | +13 µg/L CoCl$_2$•6H$_2$O | 261 | 8.9 | 5.8 |
| 7 | +52 µg/L CoCl$_2$•6H$_2$O | +52 µg/L CoCl$_2$•6H$_2$O | 252 | 7.8 | 5.7 |
| 8 | +52 µg/L CoCl$_2$•6H$_2$O | +208 µg/L CoCl$_2$•6H$_2$O | 256 | 7.0 | 5.9 |
| 9 | +208 µg/L CoCl$_2$•6H$_2$O | No cobalt addition | 257 | 7.9 | 6.4 |
| 10 | +208 µg/L CoCl$_2$•6H$_2$O | +13 µg/L CoCl$_2$•6H$_2$O | 256 | 5.7 | 6.1 |
| 11 | +208 µg/L CoCl$_2$•6H$_2$O | +52 µg/L CoCl$_2$•6H$_2$O | 265 | 6.4 | 6.5 |
| 12 | +208 µg/L CoCl$_2$•6H$_2$O | +208 µg/L CoCl$_2$•6H$_2$O | 246 | 5.1 | 6.1 |

The above data again supported the role of cobalt in reducing the production of NPI-0047 in *Salinispora tropica*. The above data suggested that cobalt present in the production media has a more significant effect in reducing the production of NPI-0047.

EXAMPLE 23

Improved the Production of NPI-2080 by *Salinispora tropica* NPS21184 in a Non-Saline, Low Chloride Medium In U.S. patent application Ser. No. 11/517,899, entitled "Biosyntheses of Salinosporamide A and its Analogs and Related Methods of Making Salinosporamide A and its Analogs," filed Sep. 8, 2006, which is incorporated herein by reference in its entirety, production of NPI-2080 (II-30), a minor salinosporamide analog present in the saline fermentation of *Salinispora tropica* NPS21184, by feeding the culture with valeric acid in instant Ocean® based medium (Example 64, Table 25) was reported. By feeding the culture of *Salinispora tropica* NPS21184 with 0.1% valeric acid, the concentration of NPI-2080 was increased from 0.90 mg/L in the control (no valeric acid addition) to 109.21 mg/L in the valeric acid-fed culture. While the concentration of Salinosporamide A (II-16) was decreased in the valeric acid-fed culture, it was still the major salinosporamide metabolite present in the saline fermentation, with a peak titer at 156.88 mg/L. It is desirable to perform the precursor-directed or precursor analog-directed biosynthetic studies for the production of desired analogs in a medium with decreased concentration of the major metabolite. In order to investigate the application of non-saline, low chloride media in the precursor-directed biosynthetic study, two seed media and two production media prepared with the following ingredients, per liter of DI $H_2O$:

|  | BAS.Sd | LoCl.Sd | BAS.Pd | LoCl.Pd |
|---|---|---|---|---|
| Media components |  |  |  |  |
| Starch | 10 g | 10 g | 10 g | 10 g |
| Hy Soy | 4 g | 4 g | 4 g | 4 g |
| Yeast Extract | 4 g | 4 g | 4 g | 4 g |
| Salt supplements |  |  |  |  |
| NaCl | 24 g | 0 | 24 g | 0 |
| $Na_2SO_4$ | 0 | 40 g | 0 | 20 g |
| KCl | 0.69 g | 0 | 0.69 g | 0 |
| $K_2SO_4$ | 0 | 1 g | 0 | 1 g |
| $CaCO_3$ | 0.43 g | 0.43 g | 1 g | 1 g |
| $MgSO_4 \cdot 7H_2O$ | 4.29 g | 4.29 g | 0 | 0 |
| $CaCl_2 \cdot 2H_2O$ | 0.43 g | 0.43 g | 0.43 g | 0 |
| $Fe_2(SO_4)_3$ | 40 mg | 40 mg | 40 mg | 40 mg |
| $SrCl_2$ | 15.5 mg | 15.5 mg | 15.5 mg | 15.5 mg |
| $H_3BO_3$ | 21.5 mg | 21.5 mg | 21.5 mg | 21.5 mg |
| NaF | 2.6 mg | 2.6 mg | 2.6 mg | 2.6 mg |

Seed Medium BAS.SD and Production Medium BAS.SD are saline fermentation media containing 24 g/L NaCl and other ion supplements. Seed Medium LoCl.SD and Production Medium LoCl.PD are low chloride, sodium sulfate-based media. Production Medium LoCl.PD contains extremely low levels of chloride ion, with the known chloride ion derived from 15.5 mg/L $SrCl_2$ and carryover chloride ion from Hy Soy and yeast extract.

Seed cultures were prepared by inoculating frozen stocks of *Salinispora tropica* NPS21184 into two different seed media, BAS.SD and LoCl,SD. The first seed cultures (10 mL medium) in 50-mL culture tubes were incubated for 3 days before inoculating 5 mL of the first seed culture into the second seed medium with the same composition as the first seed medium. The second seed cultures (100 mL medium in 500-mL Erlenmeyer flask) were incubated for 2 days before inoculating 5 mL of the second seed culture into the production media (100 mL in a 500-mL Erlenmeyer flask). BAS.SD seed culture was inoculated into BAS.PD production medium while LoCl.SD seed culture was inoculated into LoCl.PD production medium.

At about 46 hour after inoculation, valeric acid was added to the production cultures, except for the control production cultures (no valeric acid) at a final concentration of 0.1%. The production cultures were incubated for 2 hours before sterile XAD-7 resin slurry was added to the production cultures in a final concentration of 20 g/L. The production culture was then further incubated and harvested at various time points to determine productivity.

3.5 mL of the fermentation culture was mixed with equal volume of EtOAc in an extraction tube to extract the various metabolites from the production culture. The mixture was shaken on the shaker for 1 hr. An aliquot of the extract (1 mL) was removed and dried under a stream of nitrogen. The dried extract was stored at −20° C. freezer before HPLC analysis. The dried extract was resuspended in 320 µL DMSO and injected into HPLC using the 00TF14 method for analysis.

The concentration of Salinosporamide A (II-16), NPI-0047 (II-17), NPI-2065 (II-26) and NPI-2080 (II-30) was monitored by Agilent HP1100 HPLC using an ACE C-18 reversed-phase column (4.6×150 mm), and solvent system consisting of water (0.01% TF A) as solvent A and acetonitrile (0.01% UFA) as solvent B. The elution was started at 100% solvent A for 1 min, 100% solvent A to 35% solvent A gradient in 7 min, held at 35% solvent A for 11 min, 35% solvent A to 100% solvent B in 8 min and held at 100% solvent B for 9 min at a flow rate of 1.5 mL/min with the detector wavelength set at 210 nm and column temperature 35° C.

The maximum concentrations of Salinosporamide A, NPI-0047, NPI-2065 and NPI-2080 are summarized in the Table below.

TABLE 57

Effect of valeric acid on the production of Salinosporamide A, NPI-0047, NPI-2065 and NPI-2080 in saline and low chloride media

| Media conditions | Titers (mg/L) | | | |
|---|---|---|---|---|
|  | Salinosporamide A (II-16) | NPI-0047 (II-17) | NPI-2065 (II-26) | NPI-2080 (II-30) |
| BAS.PD | 274 | 6.6 | 5.5 | 0.70 |
| BAS.PD + 0.1% Valeric acid | 131 | 0.45 | 2.9 | 121 |
| LoCl.PD | 96 | 25 | 0.99 | 1.1 |
| LoCl.PD + 0.1% Valeric acid | 45 | 8.3 | 1.5 | 145 |

The concentration of Salinosporamide A in the sodium sulfate based with extremely low chloride medium was significantly lower than the saline fermentation condition. The concentration of Salinosporamide A in the low chloride medium (LoCl.PD) was 96 mg/L, about 35% of the saline fermentation condition. This may due to the lack of the substrate chlorine for the production of Salinosporamide A. By feeding valeric acid to the low chloride medium LoCl.PD, NPI-2080 was the major salinosporamide metabolite in the fermentation at a concentration of 145 mg/L, a 130-fold increase in production as compared with the control LoC.PD medium with no valeric acid. In the saline fermentation medium with valeric acid, Salinosporamide A was still the major salinosporamide metabolite. The low chloride medium (LoCl.PD) is therefore a good medium for the precursor directed and precursor-analog directed biosynthetic study for production of desired salinosporamide analogs.

EXAMPLE 24

Seed and Production Media Compositions for Fermentation of *Salinispora tropica* Organism

TABLE 58

Seed Medium - Defined Salt Composition

| Component | per liter of DI $H_2O$ |
|---|---|
| Glucose | 8 |
| Hy Soy (Kerry Bio-Science, cat. no. 5X59089) | 6 |
| Yeast Extract (USB Corp. cat. no. 23547) | 6 |
| NaCl | 24.04 g |
| $MgSO_4 \cdot 7H_2O$ | 4.29 g |

TABLE 58-continued

Seed Medium - Defined Salt Composition

| Component | per liter of DI $H_2O$ |
|---|---|
| KBr | 85.9 mg |
| KCl | 686.8 mg |
| $CaCO_3$ | 429.3 mg |
| $CaCl_2 \cdot 2H_2O$ | 429.3 mg |
| $SrCl_2$ | 15.5 mg |
| $H_3BO_3$ | 21.5 mg |
| NaF | 2.6 mg |
| $NiSO_4$ | 57.7 µg |
| $CoCl_2 \cdot 6H_2O$ | 207.9 µg |

TABLE 59

Seed Medium - "Instant Ocean"

| Component | per liter of DI $H_2O$ |
|---|---|
| Glucose | 8 g |
| Hy Soy (Kerry Bio-Science, cat. no. 5X59089) | 6 g |
| Yeast Extract (USB Corp. cat. no. 23547) | 6 g |
| Salt Mixture (Aquarium Systems, "Instant Ocean") | 30 g |

TABLE 60

Production Medium - Defined Salt Medium

| Component | per liter of DI $H_2O$ |
|---|---|
| Soluble Starch (USB Corp. No 21695) | 10 g |
| Hy Soy (Kerry Bio-Science, No. 5X59089) | 4 g |
| Yeast Extract (USB Corp. No. 23547) | 4 g |
| $CaCO_3$ | 1 g |
| $Fe_2(SO_4)_3$ | 40 mg |
| KBr | 100 mg |
| NaCl | 24.04 g |
| KCl | 686.8 mg |
| $CaCl_2 \cdot 2H_2O$ | 429.3 mg |
| $SrCl_2$ | 15.5 mg |
| $H_3BO_3$ | 21.5 mg |
| NaF | 2.6 mg |
| $CoCl_2 \cdot 6H_2O$ | 52 µg |
| NaCl | 24 g |

TABLE 61

Production Medium - "Instant Ocean"

| Component | per liter of DI $H_2O$ |
|---|---|
| Soluble Starch (USB Corp. No 21695) | 10 g |
| Hy Soy (Kerry Bio-Science, No. 5X59089) | 4 g |
| Yeast Extract (USB Corp. No. 23547) | 4 g |
| $CaCO_3$ | 1 g |
| $Fe_2(SO_4)_3$ | 40 mg |
| KBr | 100 mg |
| Salt Mixture (Aquarium Systems, "Instant Ocean") | 30 g |

EXAMPLE 25

Medium Preparation Procedure

For one liter of medium (seed or production), 500 mL deionized water is added to a 1 L beaker with a stir bar. The ingredients are added one by one to the beaker of stirring water. After all ingredients are added to the beaker, an additional 500 mL deionized water is added to the beaker. When all the ingredients are dissolved (no heat is applied in this protocol), 100-mL portions of the medium are pipetted into 500 mL Erlenmeyer flasks. The flasks are capped with a piece of cheesecloth followed by a piece of Bioshield sterile wrap and secured with a rubber band. The flasks are autoclaved at 121° C. for 30 minutes before used.

EXAMPLE 26

Fermentation of S. tropica Organism

A two stage seed train was used for a portion of this work. For the first seed stage, two frozen stock cultures of S. tropica, Strain NPS021184, ATCC accession number PTA-6685, of 1.5 mL each were transferred to 100 ml of INSTANT OCEAN® seed medium of Example 24 in a 500 ml Erlenmeyer flask. This culture was incubated at 28° C. and 250 rpm on a rotary shaker. After 3 days, a 5-mL aliquot of the first seed culture was inoculated into a 500-mL Erlenmeyer flask containing 100 mL of the same seed medium. This second seed-stage culture was incubated at 28° C. and 250 rpm on a rotary shaker for 2 days. Five-mL of the second seed-stage culture was then transferred to a 500-mL Erlenmeyer flasks containing 100 mL of the INSTANT OCEAN® production medium of Example 24. This production culture was incubated at 28° C. and 250 rpm for 5 days. Samples of the culture were taken at intervals and the dry cell weight was determined as follows: 5 mL of culture broth was centrifuged at 2300 rpm for 20 minutes, decanted retaining the mycelia, and resuspended with 5 mL of DI water with vortexing for 10 seconds; the sides of the centrifuge tube were rinsed with 2 mL of DI water; the suspension was then centrifuged an additional 20 minutes at 2300 rpm, the supernatant was discarded, and the mycelia was dried at 70° C. for at least 72 hours and weighed.

TABLE 62

Growth Profile for Example 26.

| Culture Age (Hours) | Average dry cell weight (mg) per 5 ml culture | Average dry cell weight (mg) per ml culture |
|---|---|---|
| 24 | 17.0 | 3.4 |
| 48 | 30.0 | 6.0 |
| 72 | 33.5 | 6.7 |
| 96 | 34.0 | 6.8 |
| 120 | 34.0 | 6.8 |

Onset of the stationary phase of the fermentation occurred approximately at or before 48 hrs after inoculation of the culture.

EXAMPLE 27

Resin Preparation for Fermentation

Prior to addition to a fermentation culture, the resin, as received, was prepared by washing, drying, re-slurrying, and autoclaving as follows. Washing: for 1 kg of resin, the resin was washed sequentially with 3 liters of DI water, then 1.2 liters of acetone, 1.2 liters of methanol, and 10 liters of DI water. The resin was washed with one liquid and then drained before adding the next liquid by using a Buchner funnel fitted with a vacuum flask (apply vacuum to pull the solvent). Drying: after the final wash step and the resin is drained by applying vacuum to pull the visible residual water from the resin. Re-slurry: 200 g of dried resin is added to 400 ml of DI water in a 1 liter bottle. This bottle with resin is autoclaved at 121° C. for 30 minutes prior to use.

For use, the appropriate amount of sterile resin slurry is transferred to the fermentation vessel at the desired point in the fermentation using appropriate sterile procedures.

EXAMPLE 28

Fermentation Sampling and Determination of Production of Desired Compounds

Sampling: When no resin is present, broth samples are taken for analysis by conventional methods. When resin is present, care must be exercised to obtain a representative ratio of broth to resin: while swirling the fermentation flask sufficiently to mix the resin in the broth, a 10 ml wide-tip pipette is used to extract a 3.5 ml sample of broth. This broth sample is transferred to a 16×100 mm glass extraction tube (12 ml capacity). Ethyl acetate (3.5 ml) is added to the broth and mixed for 1 hour on a Labquake rotisserie shaker. One ml of the ethyl acetate portion of the extract (top layer), is transferred to a 1.8 ml glass HPLC vial and dried under a stream of nitrogen at room temperature. The dried extract is stored at −80° C. prior to analysis.

Analysis: The dried extract is resuspended in 320 μL DMSO and 5 μL is injected into an Agilent HP1100 HPLC fitted with an ACE C-18 reversed-phase column (4.6×150 mm). A step gradient of water with 0.01% trifluoroacetic acid and aetonitrile with 0.01% trifluoroacetic acid is used as the mobile phase. The elution profile of Table 1 used. Column temperature was 35° C.

TABLE 63

HPLC Elution Profile

| Time | Solvent A<br>Water with 0.01%<br>trifluoroacetic acid | Solvent B<br>Acetonitrile with<br>0.01% trifluoroacetic<br>acid | comments |
|---|---|---|---|
| 0-1 min. | 100% | 0% | isocratic |
| 1-8 min. | Start: 100%<br>End: 35% | Start: 0%<br>End: 65% | gradient |
| 8-19 min. | 35% | 65% | Isocratic |
| 19-27 min. | Start: 35%<br>End: 0% | Start: 65%<br>End: 100% | gradient |
| 27-36 min. | 0% | 100% | isocratic |

Detection is with an Agilent photo-diode array variable wavelength UV detector with the wavelength set at 210 nm.

After equilibrating the column with a mobile phase of water with 0.01% trifluoroacetic acid, the sample is injected. The elution is accomplished with 100% Solvent A for 1 minute, then with a gradient over 7 minutes of 100% Solvent A to 35% Solvent A, then with 35% Solvent A for 11 minutes, then with a gradient over 8 minutes of 35% Solvent A to 0% Solvent A (100% Solvent B), then with 100% Solvent B for 9 minutes. The mobile phase flow rate is 1.5 ml/min; the detector wavelength is 210 nm; the column temperature is 35° C.

EXAMPLE 29

Effect of Time of Addition of the XAD-7 Resin to the Fermentation Culture on the Yield of Salinosporamide A A culture of S. tropica NPS21184 was grown using the chemically defined salt seed and production media described in Example 24 and following the procedures described in Examples 25 and 26. To different fermentation flasks, XAD-7 resin was added at 24, 48, 72, and 96 hours after inoculation following the procedure of Example 27. The resin concentration was 20 g/l. A control fermentation had no resin added. The fermentations were sampled every 24 hours for production of Salinosporamide A. The fermentations were terminated at 144 h after the final samples were taken. The results are shown below. Analysis for Salinosporainide A was performed as described in Example 28.

TABLE 64

Salinosporamide Concentration at Different Times in the Fermentation

| Time of resin | Salinosporamide A (mg/L) | | | | | |
|---|---|---|---|---|---|---|
| addition | 24 h | 48 h | 72 h | 96 h | 120 h | 144 h |
| No addition | 0 | 3 | 4 | 2 | 0.1 | 0.1 |
| 24 h | 0 | 62 | 233 | 275 | 245 | 222 |
| 48 h | ND | 3 | 158 | 224 | 219 | 178 |
| 72 h | ND | ND | 4 | 108 | 99 | 92 |
| 96 h | ND | ND | ND | 2 | 15 | 10 |

ND = Not determined

Maximum product concentrations were achieved at 96 hours. Addition of resin at hour 24 resulted in the highest concentration of product. Based on the results of Example 26, addition of the resin at 24 hr would be during the exponential phase, prior to the onset of the stationary phase of growth. Addition at 48 hr would approximately coincide with the onset of the stationary phase. Later additions were likely after the onset of the stationary phase.

TABLE 65

Increase in Maximum Product Titer for Different Resin Addition Times Compared to Control

| Time of resin addition | Maximum titer (mg/L) | Difference in titer as compared to 24 h resin addition (mg/L) | Amount of NPI-0052 synthesized since resin addition at 24 h (mg/L) |
|---|---|---|---|
| 24 h | 275 | — | — |
| 48 h | 224 | 51 | 62 |
| 72 h | 108 | 167 | 158 |

The production with resin added at hour 24 resulted in a 69-fold increase in production over the control condition.

EXAMPLE 30

Effect of the Quantity and Type of Resin Used on the Yield of Salinosporamide A: XAD-2, XAD-4 XAD-7, and XAD-16

A culture of S. tropica NPS21184 was grown using the INSTANT OCEAN® seed and production media described in Example 24 and following the procedures described in Examples 25 and 26. At 24 hours after inoculation, XAD-2, XAD-4, XAD-7 or XAD-16 resin was added to separate flasks at 20, 30 or 40 g/l concentration following the method of Example 27. A control flask had no resin added. The cultures were maintained for another 72 hours. Final samples were taken and analyzed for Salinosporamide A according to Example 28, The results are presented below:

TABLE 66

Salinosporamide A Concentrations for Different Resins and Different Resin Concentrations

| Resin | Final Concentration of resin (g/L) | NPI-0052 titer (mg/L) | Increase in NPI-0052 production as compared to the control |
|---|---|---|---|
| Control (no resin) | 0 | 5.7 | — |
| XAD-2 | 20 | 266 | 47 fold |
|  | 30 | 297 | 52 fold |
|  | 40 | 290 | 51 fold |
| XAD-4 | 20 | 207 | 36 fold |
|  | 30 | 213 | 37 fold |
|  | 40 | 232 | 41 fold |
| XAD-7 | 20 | 278 | 49 fold |
|  | 30 | 345 | 61 fold |
|  | 40 | 316 | 55 fold |
| XAD-16 | 20 | 218 | 38 fold |
|  | 30 | 237 | 42 fold |
|  | 40 | 171 | 30 fold |

The use of acrylic XAD-7 resulted in the highest production of the Salinosporamide A, with up to a 61-fold improvement over the control condition. The SDVB resins also increased the production of NPI-0052 with XAD-2 being the most effective SDVB resin showing up to a 52-fold increase over the control. While not being bound by any particular theory, the higher polarity of the acrylic XAD-7 resin may explain why it was the best resin tested in this study for the increase in production of NPI-0052. Resins with large surface area are less effective in stabilization of NPI-0052 as XAD-4, and XAD-16 are less effective than XAD-2 in increasing the production of NPI-0052.

EXAMPLE 31

Comparison of XAD-7, IRA-67, IRC-50 and IRP-64 on Production of Salinosporamide A A culture of *S. tropica* NPS21184 was grown in the INSTANT OCEAN® seed and production medium of Example 24, following the procedures of Examples 25 and 26. At 24 hours after inoculation, XAD-7, IRA-67, IRC-50 or IRP-64 resin was added to separate flasks at 20, 30 or 40 g/l concentration following the procedure of Example 27. A control flask had no resin added. The cultures were maintained for another 72 hours. Final samples were taken and analyzed for Salinosporamide A according to Example 28. The results are presented below:

TABLE 66

Salinosporamide A Concentrations for Different Resins and Different Resin Concentrations

| Resin | Final Concentration of resin (g/L) | NPI-0052 titer (mg/L) | Increase in NPI-0052 production as compared to the control |
|---|---|---|---|
| Control (no resin) | 0 | 3.9 | — |

TABLE 66-continued

Salinosporamide A Concentrations for Different Resins and Different Resin Concentrations

| Resin | Final Concentration of resin (g/L) | NPI-0052 titer (mg/L) | Increase in NPI-0052 production as compared to the control |
|---|---|---|---|
| XAD-7 | 10 | 190 | 49 fold |
|  | 20 | 272 | 70 fold |
|  | 30 | 309 | 79 fold |
|  | 40 | 321 | 82 fold |
| IRA-67 | 10 | 0.2 | (Decrease) |
|  | 20 | 0 | (Decrease) |
|  | 30 | 0 | (Decrease) |
|  | 40 | 0 | (Decrease) |
| IRC-50 | 10 | 0 | (Decrease) |
|  | 20 | 0 | (Decrease) |
|  | 30 | 0 | (Decrease) |
|  | 40 | 0 | (Decrease) |
| IRP-64 | 10 | 0 | (Decrease) |
|  | 20 | 0 | (Decrease) |
|  | 30 | 0 | (Decrease) |
|  | 40 | 0 | (Decrease) |

Addition of Amberlite IRA-67, Amberlite IRC-50 and Amberlite IRP-64 to the cultures of *S. tropica* inhibited the production of Salinosporamide A. Amberlite XAD-7 enhanced the production of this compound by 82-fold with the highest product concentration when 40 g/l of resin was used.

EXAMPLE 32

Comparison of HP-20, HP-2MG, SP-207 and SP-850 for the Production of Salinosporamide A A culture of *S. tropica* NPS21184 was grown in the INSTANT OCEAN® seed and production medium of Example 24, following the procedures of Examples 25 and 26. At 24 hours after inoculation, HP-20, HP-2MG, SP-207 or SP-850 resin was added to separate flasks at 20, 30 or 40 g/l concentration following the procedure of Example 27. A control flask had no resin added. The cultures were maintained for another 72 hours. Final samples were taken and analyzed for Salinosporamide A according to Example 28. The results are presented below:

TABLE 67

Salinosporamide A Concentrations for Different Resins and Different Resin Concentrations

| Resin | Final Concentration of resin (g/L) | NPI-0052 titer (mg/L) | Increase in NPI-0052 production as compared to the control |
|---|---|---|---|
| Control (no resin) | 0 | 3.7 | — |
| Diaion HP-20 | 10 | 219 | 59 folds |
|  | 20 | 293 | 79 folds |
|  | 30 | 309 | 84 folds |
|  | 40 | 286 | 77 folds |
| Diaion HP-2MG | 10 | 162 | 44 folds |
|  | 20 | 217 | 59 folds |
|  | 30 | 250 | 68 folds |
|  | 40 | 250 | 68 folds |
| Sepabeads SP-207 | 10 | 201 | 54 folds |
|  | 20 | 165 | 45 folds |
|  | 30 | 146 | 40 folds |
|  | 40 | 201 | 54 folds |
| Sepabeads SP-805 | 10 | 208 | 56 folds |
|  | 20 | 246 | 67 folds |

TABLE 67-continued

Salinosporamide A Concentrations for Different Resins and Different Resin Concentrations

| Resin | Final Concentration of resin (g/L) | NPI-0052 titer (mg/L) | Increase in NPI-0052 production as compared to the control |
|---|---|---|---|
| | 30 | 261 | 71 folds |
| | 40 | 225 | 61 folds |

All of these resins enhanced the production of Salinosporamide A. The highest production came from the HP-20 resin with a production increase similar to XAD-7.

EXAMPLE 33

Production of Compounds 1, 5, 6, 7, and 9 from Strain CNB476 with XAD-7 Resin Present Microorganism S. tropica, strain CNB476 (ATCC accession number PTA-5275), was grown in a 500-ml flask containing 100 ml of vegetative medium consisting of the following per liter of deionized water: glucose, 4 g; Bacto tryptone, 3 g; Bacto casitone, 5 g; and synthetic sea salt (Instant Ocean, Aquarium Systems), 30 g. The first seed culture was incubated at 28 degree C. for 3 days on a rotary shaker operating at 250 rpm. Five ml each of the first seed culture was inoculated into three 500-ml flasks containing of 100 ml of the vegetative medium. The second seed cultures were incubated at 28 degree C. and 250 rpm on a rotary shaker for 2 days. Five ml each of the second seed culture was inoculated into thirty-five 500-ml flasks containing of 100 ml of the vegetative medium. The third seed cultures were incubated at 28 degree and 250 rpm on a rotary shaker for 2 days. Five nil each of the third seed culture was inoculated into four hundred 500-ml flasks containing 100 ml of the Production Medium C consisting of the following per liter of deionized water: starch, 10 g; yeast extract, 4 g; Hy-Soy, 4 g; ferric sulfate, 40 mg; potassium bromide, 100 mg; calcium carbonate, 1 g; and synthetic sea salt (INSTANT OCEAN®), 30 g. The production cultures were incubated at 28 degree C. and 250 rpm on rotary shakers for 1 day. Approximately 2 to 3 grams of sterile Amberlite XAD-7 resin were added to the production cultures. The production cultures were further incubated at 28 degree C. and 250 rpm on rotary shakers for 5 days and achieved a titer of Compound 1 of about 200 mg/L. The culture broth was filtered through cheese cloth to recover the Amberlite XAD-7 resin. The resin was extracted 2 times with 6 liters ethyl acetate followed by 1 time with 1.5 liters ethyl acetate. The combined extracts were dried in vacuo. The dried extract, containing 3.8 grams of Compound 1 and lesser quantities of Compounds 5 and 6, was then processed for the recovery of Compounds 1, 3, 5, 6, 7, and 9.

EXAMPLE 34

Production of Compounds 1, 3, 5, 6, 7, and 9 from Strain NPS21184 with XAD-7 Resin Present Microorganism S. tropica, strain NPS21184, was grown in a 500-ml flask containing 100 ml of vegetative medium consisting of the following per liter of deionized water: glucose, 8 g; yeast extract, 6 g; Hy-Soy, 6 g; and synthetic sea salt (INSTANT OCEAN®), 30 g. The first seed culture was incubated at 28 degree C. for 3 days on a rotary shaker operating at 250 rpm. Five ml of the first seed culture was inoculated into 500-ml flask containing of 100 ml of the vegetative medium. The second seed cultures were incubated at 28 degree C. and 250 rpm on a rotary shaker for 2 days. Five ml each of the second seed culture was inoculated into 500-mi flask containing of 100 ml of the vegetative medium. The third seed cultures were incubated at 28 degree and 250 rpm on a rotary shaker for 2 days. Five ml each of the third seed culture was inoculated into 500-ml flask containing 100 ml of Production Medium D consisting of the following per liter of deionized water: starch, 20 g; yeast extract, 4 g; Hy-Soy, 8 g; ferric sulfate, 40 mg; potassium bromide, 100 mg; calcium carbonate, 1 g; and synthetic sea salt (INSTANT OCEAN®), 30 g. The production cultures were incubated at 28 degree C. and 250 rpm on rotary shakers for 1 day. Approximately 2 to 3 grams of sterile Amberlite XAD-7 resin were added to the production culture. The production culture was further incubated at 28 degree C. and 250 rpm on rotary shaker for 4 days and achieved a titer of 350-400 mg/L for Compound 1.

Alternatively, the production of the compounds can be achieved in a 42 L fermentor system using strain NPS21184. Strain NPS21184 was grown in a 500-ml flask containing 100 ml of vegetative medium consisting of the following per liter of deionized water: glucose, 8 g; yeast extract, 6 g; Hy-Soy, 6 g; and synthetic sea salt (INSTANT OCEAN®), 30 g. The first seed culture was incubated at 28 degree C. for 3 days on a rotary shaker operating at 250 rpm. Five ml of the first seed culture was inoculated into 500-ml flask containing of 100 ml of the vegetative medium. The second seed cultures were incubated at 28 degree C. and 250 rpm on a rotary shaker for 2 days. Twenty ml each of the second seed culture was inoculated into 2.8 L Fernbach flask containing 400 ml of the vegetative medium. The third seed cultures were incubated at 28 degree and 250 rpm on a rotary shaker for 2 days. 1.2 L of the third seed culture was inoculated into a 42 L fermentor containing 26 L of Production Medium C. Production Medium D and Production Medium E, with the following composition, can also be used. Production Medium E consisting of the following per liter of deionized water: starch, 15 g; yeast extract 6 g; Fly-Soy, 6 g; ferric sulfate, 40 mg; potassium bromide, 100 mg; calcium carbonate, 1 g; and synthetic sea salt (Instant Ocean, Aquarium Systems), 30 g. The fermentor cultures were operated at the following parameters: temperature, 28 degree C.; agitation, 200 rpm; aeration, 13 L/min and back pressure, 4.5 psi. At 36 to 44 hours of the production cycle, approximately 600 grams of sterile Amberlite XAD-7 resin were added to the fermentor culture. The production culture was further incubated at the above operating parameters until day 4 of the production cycle. The aeration rate was lowered to 8 L/min. At day 5 of the production cycle, the fermentor culture achieved a titer of about 300 mg/L for Salinosporamide A. The culture broth was filtered through cheese cloth to recover the Amberlite XAD-7 resin. The resin was extracted with 2 times 4.5 L liters ethyl acetate followed by 1 time 1.5 liters ethyl acetate. The combined extracts were dried in vacuo. The dried extract was then processed for the recovery of Compounds 1, 2, 3, 5, 6, and 9.

EXAMPLE 35

Purification of Compounds Isolated in Examples 33 and 34

The pure Compounds of 1, 5, 6, 7, and 9 were obtained by flash chromatography followed by HPLC. Eight grams crude extract containing 3.8 grams of Compound 1 and lesser quantities of Compounds 3, 6, 7, and 9 was processed by flash chromatography using Biotage Flash40i system and Flash 40M cartridge (KP-Sil Silica, 32-63 μm, 90 grams). The flash chromatography was developed by the following step gradient:
1. Hexane (1 L)
2. 10% Ethyl acetate in hexane (1 L)
3. 20% Ethyl acetate in hexane, first elution (1 L)
4. 20% Ethyl acetate in hexane, second elution (1 L)
5. 20% Ethyl acetate in hexane, third elution (1 L)
6. 25% Ethyl acetate in hexane (1 L)
7. 50% Ethyl acetate in hexane (1 L)
8. Ethyl acetate (1 L)

Fractions containing Compound 1 in greater or equal to 70% UV purity by HPLC were pooled and subject to HPLC purification, as described below, to obtain Compound 1, along with Compounds 5 and 6, each as pure compounds.

TABLE 68

| Column | Phenomenex Luna 10u Silica |
| --- | --- |
| Dimensions | 25 cm × 21.2 mm ID |
| Flow rate | 25 ml/min |
| Detection | ELSD |
| Solvent | Gradient of 24% EtOAc/hexane for 19 min, 24% EtOAc/hexane to 100% EtOAc in 1 min, then 100% EtOAc for 4 min |

The fraction enriched in Compound 1 (described above; ~70% pure with respect to Compound 1) was dissolved in acetone (60 mg/ml). Aliquots (950 of this solution were injected onto a normal-phase HPLC column using the conditions described above. Compound 1 typically eluted after 14 minutes and Compounds 6 and 7 co-eluted as a single peak at 11 min. When parent samples containing Compounds 2, 5, and 9 were processed, Compound 2 eluted at 22 minutes, while Compounds 5 and 9 co-eluted at 23 minutes during the 100% ethyl acetate wash. Fractions containing Compound 1 and minor analogs were pooled based on composition of compounds present, and evaporated under reduced pressure on a rotary evaporator. This process yielded pure Compound A, as well as separate fractions containing minor Compounds 5, 6, 7, and 9, which were further purified as described below.

Sample containing Compounds 6 and 7 generated from the process described above were further separated using reversed-phase preparative HPLC as follows. The sample containing compound 6 (70 mg) was dissolved in acetonitrile at a concentration of 10 mg/ml, and 500 μl was loaded on an HPLC column of dimensions 21 mm i.d. by 15 cm length containing Eclipse XDB-C18 support. The solvent gradient increased linearly from 15% acetonitrile/85% water to 100% acetonitrile over 23 minutes at a flow rate of 14.5 ml/min. The solvent composition was held at 100% acetonitrile for 3 minutes before returning to the starting solvent mixture. Compound 7 eluted at 17.5 minutes while Compound 6 eluted at 19 minutes under these conditions.

Crystalline Compound 7 was obtained using a vapor diffusion method. Compound 7 (15 mg) was dissolved in 100 of acetone in a 1.5 ml v-bottom HPLC vial. This vial was then placed inside a larger sealed vessel containing 1 ml of pentane. Crystals suitable for X-ray crystallography experiments were observed along the sides and bottom of the inner vial after 48 hours of incubation at 4° C. Crystallography data was collected on a Bruker SMART APEX CCD X-ray diffractonieter (F(000)=2656, Mo$_{K\alpha}$ radiation, $\lambda$=0.71073 Å, μ=0.264 mm$^{-1}$, T=100 K) at the UCSD Crystallography Lab and refinement method used was full-matrix least-squares on F$^2$. Crystal data NPI-2065: C$_{15}$H$_{20}$ClNO$_4$, MW=313.77, tetragonal, space group P4(1)2(1)2, a=b=11.4901(3) Å, c=46.444(2) Å, α=β=γ=90°, vol=6131.6(3) Å$^3$, Z=16, $\rho_{calcd}$=1.360 g cm$^{-3}$, crystal size, 0.30×0.15×0.07 mm$^3$, θ range, 1.75-26.00°, 35367 reflections collected, 6025 independent reflections (R$_{int}$=0.0480), final R indices (I>2σ(l)): R$_1$=0.0369, wR$_2$=0.0764, GOF=1.060.

In order to separate Compounds 9 from 5, a reverse-phase isocratic method was employed. Sample (69.2 mg) containing both compounds was dissolved in acetonitrile to a concentration of 10 mg/ml, and 500 μl was loaded on a reverse-phase HPLC column (ACE 5 C18-HL, 15 cm×21 mm ID) per injection. An isocratic solvent system of 27% acetonitrile/63% water at flow rate of 14.5 ml/min was used to separate compounds II-28 and II-20, which eluted after 14 and 16 minutes, respectively. Fractions containing compounds of interest were immediately evaporated under reduced pressure at room temperature on a rotary evaporator. Samples were then loaded onto a small column of silica and eluted with 10 ml of 70% hexane/30% acetone to remove additional impurities.

Samples generated from the preparative normal-phase HPLC method described above that contained Compound 5, but which were free of Compound 9 could also be triturated with 100% EtOAc to remove minor lipophilic impurities.

Compound 1: UV (Acetonitrile/H$_2$O) $\lambda_{max}$ 225(sh) nm. Low Res. Mass: m/z 314 (M+H), 336 (M+Na).

Compound 5: UV (Acetonitrile/H$_2$O) $\lambda_{max}$ 225(sh) nm. Low Res. Mass: m/z 266 (M+H); FIRMS (ESI), m/z 266.1396 (M+H), $\Delta_{calc}$=1.2 ppm.

Compound 6: UV (Acetonitrile/H$_2$O) $\lambda_{max}$ 225(sh) nm. Low Res. Mass: m/z 328 (M+H), 350 (M+Na); FIRMS (ESI), m/z 328.1309 (M+H), $\alpha_{calc}$=-2.0 ppm, C$_{16}$H$_{23}$NO$_4$Cl.

Compound 7: UV (Acetonitrile/H$_2$O) $\lambda_{max}$ 225(sh) nm; HRMS (ESI), m/z 314.1158 (M+H), $\Delta_{calc}$=-0.4 ppm, C$_{15}$H$_{21}$NO$_4$Cl.

Compound 9: UV (Acetonitrile/H$_2$O) $\lambda_{max}$ 225(sh) nm; FIRMS (ESI), m/z 266.1388 (M+H), $\Delta_{calc}$=-1.8 ppm, C$_{14}$H$_{20}$NO$_4$.

3B: Purification of Compound of Formula 1-7

A Biotage Flash 75Li system with a Flash 75L KP-Sil cartridge was used to process the filtered crude extract (10.0 g), enriched in Compound 1 and containing Compound of Formula 1-7. The crude extract was dissolved to a concentration of 107 mg/ml in acetone and loaded directly onto the cartridge. The following solvent step gradient was then run through the cartridge at a flow rate between 235 ml/min and 250 ml/min
1. 10% EtOAc in n-Heptane (3.2 L)
2. 25% EtOAc in n-Heptane (16 L)
3. 30% EtOAc in n-Heptane (5.4 L)

Fractions enriched in Compound 1 were pooled and concentrated by rotavapor until ~5% of the total pooled volume of solvent remained. The solvent was removed, leaving behind the white solid.

A crystallization was then performed on the solid by dissolving the sample (4.56 g) in 1:1 acetone:n-heptane (910 ml). The solvent was slowly evaporated using a rotary evaporator until the solvent was reduced to about 43% of its original volume. The solution (supernatant) was removed and concentrated (598 mg).

The supernatant was dissolved in acetone (80 mg/ml). Aliquots (500 μl) of this solution were injected onto a normal-phase HPLC column using the conditions described above for normal phase purification of Compounds 1, 6, 7, and 9. Compound 3 eluted at 7.5 minutes as a pure compound.

Compound 3: UV (Acetonitrile/H$_2$O) $\lambda_{max}$ 225(sh) nm. Low Res. Mass: m/z 298 (M+H), 320 (M+Na).

EXAMPLE 36

Fermentation of Compounds 2, 4, and 8

Microorganism *S. tropica*, strain CNB476, was grown in a 500-ml flask containing 100 ml of the first vegetative medium consisting of the following per liter of deionized water: glucose, 4 g; Bacto tryptone, 3 g; Bacto casitone, 5 g; and synthetic sea salt (Instant Ocean, Aquarium Systems), 30 g. The first seed culture was incubated at 28 degree C. for 3 days on a rotary shaker operating at 250 rpm. Five ml of the first seed culture was inoculated into a 500-ml flask containing 100 ml of the second vegetative medium consisting of the following per liter of deionized water: starch, 10 g; yeast extract, 4 g; peptone, 2 g; ferric sulfate, 40 mg; potassium bromide, 100 mg; calcium carbonate, 1 g; and sodium bromide, 30 g. The second seed cultures were incubated at 28° C. for 7 days on a rotary shaker operating at 250 rpm. Approximately 2 to 3 gram of sterile Amberlite XAD-7 resin were added to the second seed culture. The second seed culture was further incubated at 28° C. for 2 days on a rotary shaker operating at 250 rpm. Five ml of the second seed culture was inoculated into a 500-ml flask containing 100 ml of the second vegetative medium. The third seed culture was incubated at 28° C. for 1 day on a rotary shaker operating at 250 rpm. Approximately 2 to 3 gram of sterile Amberlite XAD-7 resin were added to the third seed culture. The third seed culture was further incubated at 28° C. for 2 days on a rotary shaker operating at 250 rpm. Five ml of the third culture was inoculated into a 500-ml flask containing 100 ml of the second vegetative medium. The fourth seed culture was incubated at 28° C. for 1 day on a rotary shaker operating at 250 rpm. Approximately 2 to 3 gram of sterile Amberlite XAD-7 resin were added to the fourth seed culture. The fourth seed culture was further incubated at 28° C. for 1 day on a rotary shaker operating at 250 rpm. Five ml each of the fourth seed culture was inoculated into ten 500-ml flasks containing 100 ml of the second vegetative medium. The fifth seed cultures were incubated at 28° C. for 1 day on a rotary shaker operating at 250 rpm. Approximately 2 to 3 grams of sterile Amberlite XAD-7 resin were added to the fifth seed cultures. The fifth seed cultures were further incubated at 28° C. for 3 days on a rotary shaker operating at 250 rpm. Four ml each of the fifth seed culture was inoculated into one hundred and fifty 500-ml flasks containing 100 ml of the production medium having the same composition as the second vegetative medium. Approximately 2 to 3 grams of sterile Amberlite XAD-7 resin were also added to the production culture. The production cultures were incubated at 28° C. for 6 day on a rotary shaker operating at 250 rpm. The culture broth was filtered through cheese cloth to recover the Amberlite XAD-7 resin. The resin was extracted with 2 times 3 liters ethyl acetate followed by 1 time 1 liter ethyl acetate. The combined extracts were dried in vacuo. The dried extract, containing 0.42 g of the compound Formula II-17 and 0.16 gram the compound of Formula II-18, was then processed for the recovery of the compounds.

EXAMPLE 37

Purification of Compounds 2, 4, and 8

Pure Compounds 2 and 4 were obtained by reversed-phase HPLC as described below:

TABLE 69

| Column | ACE 5 C18-HL |
|---|---|
| Dimensions | 15 cm × 21 mm ID |
| Flow rate | 14.5 ml/min |
| Detection | 214 nm |
| Solvent | Gradient of 35% Acetonitrile/65% H$_2$O to 90% Acetonitrile/10% H$_2$O over 15 min |

Crude extract (100 mg) was dissolved in 15 ml of acetonitrile. Aliquots (900 µl) of this solution were injected onto a reversed-phase HPLC column using the conditions described above. Compounds 2 and 4 eluted at 7.5 and 9 minutes, respectively. Fractions containing the pure compounds were first concentrated using nitrogen to remove organic solvent. The remaining solution was then frozen and lyophilized to dryness.

An alternative purification method for Compounds 2 and 4 was developed for larger scale purification and involved fractionation of the crude extract on a normal phase VLC column. Under these conditions, sufficient amounts of several minor metabolites were identified, including Compound 8. The crude extract (2.4 g) was dissolved in acetone (10 ml) and this solution adsorbed onto silica gel (10 cc) by drying in vacuo. The adsorbed crude extract was loaded on a normal phase silica VLC column (250 cc silica gel, column dimensions 2.5 cm diameter by 15 cm length) and washed with a step gradient of hexane/EtOAc, increasing in the percentage of hexane in steps of 5% (100 ml solvent per step). The majority of compound 1 eluted in the 60% hexane/40% EtOAc wash while the majority of compound 2 eluted in the 50% hexane 50% ethyl acetate wash. Final separation of the compounds was achieved using C18 HPLC chromatography (ACE 5µ C18-HL, 150 mm×21 mm ID) using an isocratic solvent system consisting of 35% ACN/65% H2O. Under these conditions, Compound 8 eluted at 11 minutes, Compound 2 eluted at 12.00 minutes, traces of Compound 1 eluted at 23.5 minutes, and Compound 4 eluted at 25.5 minutes. The resulting samples were dried in vacuo using no heat to remove the aqueous solvent mixture. The spectroscopic data for these samples of Compound 1 and Compound 4 were found to be identical with those of samples prepared from earlier purification methods. The sample of Compound 4 was found to contain 8% of the lactone hydrolysis product and was further purified by washing through a normal phase silica plug (1 cm diameter by 2 cm height) and eluting using a solvent mixture of 20% EtOAc/80% Hexanes (25 ml). The resulting sample was found to contain pure Compound 4.

The fractions containing Compound 8 described above were further purified using normal phase semipreparative HPLC (Phenomenex Luna Si 10µ, 100 Å; 250×10 mm id) using a solvent gradient increasing from 100% hexane to 100% EtOAc over 20 minutes with a flowrate of 4 ml/min. Compound 8 eluted as a pure compound after 11.5 minutes (0.8 mg, 0.03% isolated yield from dried extract weight).

Compound 2: UV (Acetonitrile/H$_2$O) $\lambda_{max}$ 225(sh) nm, High Res. Mass (APCI): m/z 280.156 (M+H), $\Delta_{calc}$=2.2 ppm, C$_{15}$H$_{22}$NO$_4$.

Compound 4: UV (Acetonitrile/H$_2$O) $\lambda_{max}$ 225(sh) nm. High Res. Mass APC D: m/z 358.065 (M+H), $\Delta_{calc}$=−1.9 ppm, C$_{15}$H$_{21}$NO$_4$Br.

Compound 8: UV (Acetonitrile/H$_2$O) $\lambda_{max}$ 225(sh) nm; MS (HR-ESI), m/z 280.1556 (M+H) $\Delta_{calc}$=2.7 ppm (C$_5$H$_{22}$NO$_4$).

What is claimed is:

1. A salt formulation for use in fermenting a marine microorganism, the formulation comprising:
    (a) NaCl in the salt formulation at a mass percent between 92% and 76%;
    (c) KCl in the salt formulation at a mass percent between 5% and 1.50%;
    (d) CaCl$_2$•H$_2$O in the salt formulation at a mass percent between 3% and 1%;
    (e) SrCl$_2$ in the salt formulation at a mass percent between 0.10% and 0.025%;
    (f) H$_3$BO$_3$•7H$_2$O in the salt formulation at a mass percent between 0.20% and 0.04%; and
    (g) NaF in the salt formulation at a mass percent between 0.05% and 0.005%.

2. The salt formulation of claim 1, further comprising CaCO$_3$ at a mass percent between 5% and 1%.

3. The salt formulation of claim 1, further comprising CoCl$_2$•6H$_2$O.

4. The salt formulation of claim 1, further comprising KBr at a mass percent between 3% and 0.10%.

5. The salt formulation of claim 1, further comprising Fe$_2$(SO$_4$)$_3$.

6. A salt formulation for use in fermenting a marine microorganism, the formulation comprising:
    (a) Na$_2$SO$_4$ at a mass percent between 85% and 72%;
    (c) KCl at a mass percent between 5% and 3%;
    (d) CaCl$_2$•H$_2$O at a mass percent between 3% and 1%;
    (e) SrCl$_2$ at a mass percent between 0.15% and 0.05%;
    (f) H$_3$BO$_3$•7H$_2$O at a mass percent between 0.30% and 0.10%; and
    (g) NaF at a mass percent between 0.03% and 0.01%.

7. The salt formulation of claim 6, further comprising CaCO$_3$ at a mass percent between 20% and 0.5%.

8. The salt formulation of claim 6, further comprising CoCl$_2$•6H$_2$O.

9. The salt formulation of claim 6, further comprising KBr at a mass percent between 3% and 0.10%.

10. The salt formulation of claim 6, further comprising Fe$_2$(SO$_4$)$_3$.

11. A salt formulation for use in fermenting a marine microorganism, the formulation comprising:
    (a) KCl at a mass percent between 90% and 75%;
    (b) MgSO$_4$ at a mass percent between 20% and 5%
    (c) CaCl$_2$ at a mass percent between 5% and 3%;
    (d) SrCl$_2$ at a mass percent between 0.3% and 0.03%;
    (e) H$_3$BO$_3$ at a mass percent between 0.4% and 0.04%; and
    (f) NaF at a mass percent between 0.03% and 0.01%.

* * * * *

UNITED STATES PATENT AND TRADEMARK OFFICE
CERTIFICATE OF CORRECTION

| | | |
|---|---|---|
| PATENT NO. | : 10,793,824 B2 | Page 1 of 1 |
| APPLICATION NO. | : 16/000358 | |
| DATED | : October 6, 2020 | |
| INVENTOR(S) | : Kin Sing Lam et al. | |

It is certified that error appears in the above-identified patent and that said Letters Patent is hereby corrected as shown below:

In the Claims

At Column 93, Claim number 1, Line number 14:
"(d) $CaCl_2 \cdot H_2O$ in the salt formulation at a mass percent"
Should read:
-- (d) $CaCl_2 \cdot 2H_2O$ in the salt formulation at a mass percent --

At Column 93, Claim number 3, Line number 25:
"$CoCl_2 \cdot 6H_2O$."
Should read:
-- $CoCl_2 \cdot 6H_2O$. --

At Column 94, Claim number 6, Line number 5:
"(d) $CaCl_2 \cdot H_2O$ at a mass percent between 3% and 1%"
Should read:
-- (d) $CaCl_2 \cdot 2H_2O$ at a mass percent between 3% and 1% --

At Column 94, Claim number 6, Line number 7:
"(f) $H_3BO_3 \cdot 7H_2O$ at a mass percent between 0.30% and"
Should read:
-- (f) $H_3BO_3 \cdot 7H_2O$ at a mass percent between 0.30% and --

At Column 94, Claim number 8, Line number 13:
"$CoCl_2 \cdot 6H_2O$."
Should read:
-- $CoCl_2 \cdot 6H_2O$. --

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*